United States Patent
Bishop et al.

(10) Patent No.: US 8,759,066 B2
(45) Date of Patent: Jun. 24, 2014

(54) THROMBIN ACTIVATOR COMPOSITIONS AND METHODS OF MAKING AND USING THE SAME

(75) Inventors: Paul D. Bishop, Fall City, WA (US); Tracey A. Pownder, Seattle, WA (US); Paul O. Sheppard, Granite Falls, WA (US); Christopher J. Stenland, Stanwood, WA (US)

(73) Assignee: Zymogenetics, Inc., Seattle, WA (US)

( * ) Notice: Subject to any disclaimer, the term of this patent is extended or adjusted under 35 U.S.C. 154(b) by 653 days.

(21) Appl. No.: 12/935,235

(22) PCT Filed: Apr. 7, 2009

(86) PCT No.: PCT/US2009/039757
§ 371 (c)(1),
(2), (4) Date: Feb. 7, 2011

(87) PCT Pub. No.: WO2009/126616
PCT Pub. Date: Oct. 15, 2009

(65) Prior Publication Data
US 2011/0151536 A1 Jun. 23, 2011

Related U.S. Application Data

(60) Provisional application No. 61/043,054, filed on Apr. 7, 2008.

(51) Int. Cl.
*C12N 9/48* (2006.01)
*C12N 15/00* (2006.01)
*C12P 21/06* (2006.01)
*C12P 21/04* (2006.01)
*C07H 21/04* (2006.01)

(52) U.S. Cl.
USPC ......... 435/212; 435/440; 435/69.1; 435/71.1; 536/23.2

(58) Field of Classification Search
None
See application file for complete search history.

(56) References Cited

U.S. PATENT DOCUMENTS

| 5,298,599 A | 3/1994 | Rezaie et al. |
| 6,413,737 B1 * | 7/2002 | Olsen et al. ................. 435/68.1 |
| 2003/0235577 A1 | 12/2003 | Shapiro et al. |
| 2005/0164365 A1 | 7/2005 | Yonemura et al. |

OTHER PUBLICATIONS

Branden et al. Introduction to Protein Structure, Garland Publishing Inc., New York, p. 247, 1991.*
Lenz et al. Matrix Metalloproteinases in Renal Development and Disease. J Am Soc Nephrol. 2000. 11:574-581; p. 574, col. 1. last para; and Fig 1.
Klein et al. The possible role of a matix metalloproteinase (MMP)-2 and MMP-9 in cancer, e.g. acute leukemia. Crit Rev. Oncol Hematol. 2004, 50(2):87-100; p. 89, col. 1, para 3, and col. 2, para 1.
Nishida et al. cDNA cloining and deduced amino acid sequence of prothrombin activator (ecarin) from Kenyan Echis carinatus venom. Biochemistry 1995, 34(5);1771-1778; Abstract.
Lafleur M A et al., "Activation of pro-(matrix metalloproteinase-2) (pro-MMP-2) by thrombin is membrane-type-MMP-dependent in human umbilical vein endothelial cells and generates a distinct 63 kDa active species.", The Biochemical Journal 1, Jul. 2001 LNKD-PUBMED: 11415441, vol. 357, No. Pt 1, Jul. 1, 2001, pp. 107-115, XP002649079, ISSN: 0264-6021, p. 107, right-hand column, paragraph 2—paragraph 3.
Fox Jay W et al., "Insights into and speculations about snake venom metalloproteinase (SVMP) synthesis, folding and disulfide bond formation and their contribution to venom complexity.", The FEBS Journal, vol. 275, No. 12, Jun. 2008, pp. 3016-3030, XP002649080, ISSN: 1742-464X, the whole document, figures 1, 2.
Supplementary European Search Report dated Jul. 14, 2011.

* cited by examiner

*Primary Examiner* — Yong Pak
(74) *Attorney, Agent, or Firm* — Sterne, Kessler, Goldstein & Fox, PLLC

(57) ABSTRACT

Disclosed are compositions for activating thrombin precursors to thrombin. The compositions provided include polypeptide compositions wherein the pre-pro-sequence comprises a thrombin cleavage site. The compositions provided also include polynucleotides encoding said polypeptides and recombinant systems for expressing said polypeptides. This disclosure also relates to methods for producing said compositions, recovering said compositions, activating said compositions purifying said compositions and producing active thrombin molecules using the active form of said compositions.

13 Claims, No Drawings

THROMBIN ACTIVATOR COMPOSITIONS AND METHODS OF MAKING AND USING THE SAME

RELATED APPLICATIONS

This application claims the benefit of U.S. Patent application Ser. No. 61/043,054, filed Apr. 7, 2008, which is incorporated herein by reference.

FIELD OF THE INVENTION

Thrombin activating compositions, and methods of making and using the same are provided herein.

BACKGROUND OF THE INVENTION

The penultimate step of the blood coagulation cascade is the Factor Xa-complex-catalyzed conversion of prothrombin to the active enzyme thrombin. Prothrombin is a single-chain, vitamin K-dependent glycoprotein that is synthesized in the liver. It contains a gla domain, two kringle regions, an A chain, and a serine protease domain (B chain). During conversion thrombin, prothrombin is cleaved in two places, removing the gla domain and kringle regions and cleaving between the A and B chains to produce the active protease, α-thrombin. Thrombin is used therapeutically to promote hemostasis in surgery and as a component of tissue adhesives and sealants. Human and bovine thrombins, both derived from plasma, and recombinant human thrombin, are all currently approved for therapeutic use.

Recombinant thrombin is an alternative to plasma-derived thrombin, thus avoiding the potential for contamination that is inherent in plasma-derived products. Ex vivo, active thrombin is produced from prothrombin or variants thereof (e.g., prethrombin-1) by treatment with any of several activating proteases, including those obtained from snake venom. Hence, because of the utility of snake venom proteases in the production of recombinant human thrombin, there is a need for improved recombinant venom-derived proteases that offer, inter alia, higher yield.

SUMMARY OF THE INVENTION

In one aspect, the present invention provides a recombinant metalloprotease pre-pro-activator comprising, from an amino-terminal position to a carboxyl-terminal position, a pre-pro leader; a thrombin cleavage site consisting of a glycine, a proline, and an arginine; and a mature activator, wherein the pre-pro polypeptide shares at least 60% sequence identity with the pre-pro polypeptide, or a portion thereof, from a wild-type metalloprotease pre-pro-activator, and wherein the mature activator shares at least 60% sequence identity with the mature activator from the wild-type metalloprotease pre-pro-activator. In certain embodiments, the pre-pro polypeptide shares at least 60% sequence identity with amino acid residues x-187 of SEQ ID NO:100, wherein x is an integer from 1 to 153, inclusive; and wherein the mature activator shares at least 60% sequence identity with amino acid residues 191-616 of SEQ ID NO:100. In some variations, the wild-type metalloprotease pre-pro-activator is selected from the group consisting of: ecarin from Kenyan *Echis carinatus*, ecarin from *Echis carinatus leucogaster*, jararhagin from *Bothrops jararaca*; HR1B from *Trimeresrus flavoviridis*; Ht-e from *Crotalus atrox*; protrigramin from *Trimeresurus gramineus*; prorhodostomin from *Calloselasma rhodostoma*; and RVVh from Russell's viper venom.

In particular embodiments, the recombinant metalloprotease pre-pro-activator shares at least 90% or 99% sequence identity with the amino acid sequence shown in residues 1-616 of SEQ ID NO:2. The pre-pro-activator may further comprise an affinity tag (e.g., a histidine tag) positioned carboxyl-terminal to the mature activator. In some embodiments, the recombinant metalloprotease pre-pro-activator consists essentially of the pre-pro leader, the thrombin cleavage site, and the mature activator.

In certain variations of a recombinant metalloprotease pre-pro-activator as above, the pre-pro leader comprises at least thirty-five contiguous amino acid residues from among amino acid residues 1-187 of SEQ ID NO:100. For example, in some embodiments, the leader comprises amino acid residues 153-187 or 1-187 of SEQ ID NO:100.

In a specific variation, the recombinant metalloprotease pre-pro-activator comprises the amino acid sequence shown in residues 1-616 of SEQ ID NO:2.

In another aspect, the present invention provides an isolated polynucleotide encoding a recombinant metalloprotease pre-pro-activator as described above. In particular embodiments, the polynucleotide comprises the nucleotide sequence shown in residues 1-1848 of SEQ ID NO:1 or nucleotides 1-1848 of SEQ ID NO:3. In yet another aspect, the present invention provides an expression vector comprising a polynucleotide encoding a recombinant metalloprotease pre-pro-activator as described above. In some embodiments, the polynucleotide encoding the pre-pro-activator is codon-optimized for expression in a microbial expression system. In specific variations, the polynucleotide comprises the nucleotide sequence shown in nucleotides 1-1848 of SEQ ID NO:1 or nucleotides 1-1848 of SEQ ID NO:3.

In yet another aspect, the present invention provides a method of producing a recombinant metalloprotease pre-pro-activator. The method generally includes transfecting a host cell with an expression vector comprising a polynucleotide sequence encoding a pre-pro-activator as described above, and expressing the encoded pre-pro-activator from the expression vector. The polynucleotide sequence may be codon optimized for expression in a microbial expression system; for example, in a specific embodiment, the polynucleotide comprises the nucleotide sequence 1-1848 of SEQ ID NO:1. Suitable host cells include mammalial cells. In particular variations, the host cell is a hamster cell such as, e.g., a Chinese Hamster Ovary (CHO) cell.

In certain embodiments of a method as above, the method further includes recovering the expressed pre-pro-activator from the host cell or host cell medium. In some such embodiments, the method also includes activating the recovered pre-pro-activator so as to produce a mature activator.

In other embodiments, the method of producing the pre-pro-activator further includes activating the expressed pre-pro-activator so as to produce a mature activator. In some such embodiments, the method also includes recovering mature activator.

Where the method includes an activation step, such activation may be performed using, e.g., thrombin as an activator. In some alternative embodiments, activation is performed using an activator selected from trypsin and heat. In certain variations, the activator is added to a cell culture medium containing the host cell.

In still another aspect, the present invention provides an isolated pre-pro-activator or mature activator polypeptide produced by a method as described above. In particular embodiments, a mature activator produced as above shares at least 90% or at least 99% sequence identity with the amino acid sequence shown in residues 191-616 of SEQ ID NO:2. In more specific variations, a mature activator produced as above comprises amino acid residues 188-616 of SEQ ID NO:2, 189-616 of SEQ ID NO:2, 190-616 of SEQ ID NO:2, or 191-616 of SEQ ID NO:2. In some embodiments, a mature activator produced as above is complexed with a non-zinc transition metal cation; particularly suitable non-zinc transition metal cations include, e.g., $Cu^{2+}$, $Co^{2+}$ and $Ni^{2+}$.

In another aspect, the present invention provide a method of activating a thrombin precursor to thrombin comprising contacting a thrombin precursor (e.g., prothrombin-1) with a mature activator produced by a method as described above, wherein said thrombin precursor is cleaved at the ecarin cleavage site. In particular variations, the mature activator comprises amino acid residues 188-616 of SEQ ID NO:2, 189-616 of SEQ ID NO:2, 190-616 of SEQ ID NO:2, or 191-616 of SEQ ID NO:2. The mature activator may be immobilized to a resin such as, e.g., a cyanogen bromide-activated sepharose beaded resin support. In some embodiments, the mature activator is contacted with a solution containing a non-zinc transition metal cation (e.g., $Cu^{2+}$, $Co^{2+}$, or $Ni^{2+}$), prior to contacting the mature activator with the thrombin precursor.

In yet another aspect, the present invention provides an isolated, zinc metalloprotease complexed with a non-zinc transition metal cation. Particularly suitable non-zinc transition metal cations include, for example, $Cu^{2+}$, $Co^{2+}$ and $Ni^{2+}$. In typical embodiments, the zinc metalloprotease comprises a zinc-binding active site containing the motif $Xaa_1$-His-Glu-$Xaa_2$-$Xaa_3$-His-$Xaa_4$-$Xaa_5$-Gly-$Xaa_6$-$Xaa_7$-His-$Xaa_8$ (SEQ ID NO:102). For example, in certain embodiments, the zinc metalloprotease comprises the zinc-binding active site containing the motif $Xaa_1$-His-Glu-$Xaa_2$-$Xaa_3$-His-$Xaa_4$-$Xaa_5$-Gly-$Xaa_6$-$Xaa_7$-His-$Xaa_8$, wherein $Xaa_1$ is Ala, $Xaa_3$ is Gly, and $Xaa_8$ is Asp (SEQ ID NO:103).

In specific variations, the metalloprotease is selected from the group consisting of Zinc metalloproteinase-disintegrin ecarin precursor (VMECA_ECHCA, designations per Swiss Institute of Bioinformatics, available through the ExPASy organization's web site); Metalloproteinase rhodostoxin/Disintegrin rhodostomin from *Agkistrodon rhodostoma* (DIS-R_AGKRH); Zinc metalloproteinase-disintegrin BITM06A from *Bothrops insularis* (VM6A_BOTIN); Zinc metalloproteinase-disintegrin bothropasin from *Bothrops jararaca* (VMBOP_BOTJA); Zinc metalloproteinase-disintegrin jararhagin/Disintegrin jararhagin-C from *Bothrops jararaca* (VMJAR_BOTJA); Zinc metalloproteinase-disintegrin of *Crotalus durissus durissus* (VM_CRODD); Zinc metalloproteinase-disintegrin berythractivase from *Bothrops erythromelas* (VMBER_BOTER); Zinc metalloproteinase ACLH from *Agkistrodon contortrix laticinctus* (VM-ACH_AGKCL); Zinc metalloproteinase-disintegrin ACLD, also from *Agkistrodon contortrix laticinctus* (VMED_AGKCL); Zinc metalloproteinase-disintegrin/Metalloproteinase Mt-b, from *Agkistrodon halys brevicaudus* (VMMTB_AGKHB); Zinc metalloproteinase Bap1 from *Bothrops aper* (VMBP1_BOTAS); Zinc metalloproteinase-disintegrin Eoc1 from *Echis ocellatus* (VM1_ECHOC); Zinc metalloproteinase-disintegrin bilitoxin-1 from *Agkistrodon bilineatus* (VMBI1_AGKBI); Zinc metalloproteinase neuwiedase from *Bothrops newiedi pauloensis* (VM-NEU_BOTNE); Zinc metalloprotease-disintegrin halysase from *Agkistrodon halys pallas* (VMHA_AGKHP); Zinc metalloproteinase-disintegrin VLAIP-A from *Vipera lebetina* (VMIPA_VIPLE); Zinc metalloproteinase-disintegrin HF3 from *Bothrops jararaca* (VMHF3_BOTJA); Zinc metalloproteinase-disintegrin VLAIP-B from *Vipera lebetina* (VMIPB_VIPLE); A disintegrin and metalloproteinase domain 25/ADAM 25 from *Mus musculus* (ADA25_MOUSE); A disintegrin and metalloproteinase domain 26/ADAM 26A from *Mus musculus* (AD26A_MOUSE); A disintegrin and metalloproteinase domain 9/ADAM 9 from *Homo sapiens* (ADAM9_HUMAN); and A disintegrin and metalloproteinase domain 21/ADAM 21 (ADA21_HUMAN). In some embodiments, the metalloprotease comprises an amino acid sequence having at least 95% sequence identity (e.g., 100% sequence identity) with the amino acid sequence shown in residues 191-616 of SEQ ID NO:100.

These and other aspects of the invention will become evident upon reference to the following detailed description.

DETAILED DESCRIPTION

It should be understood that this invention is not limited to the particular methodology, protocols, and reagents, etc., described herein as such may vary. The terminology used herein is for the purpose of describing particular embodiments only, and is not intended to limit the scope of the present invention.

As used herein and in the claims, the singular forms "a," "an," and "the" include the plural reference unless the context clearly indicates otherwise. Thus, for example, the reference to an antibody is a reference to one or more such antibodies, including equivalents thereof known to those skilled in the art. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described here.

The present invention provides for a new form of recombinant zymogen metalloproteinase in which the zymogen has been molecularly engineered to contain an exogenous cleavage site. When compared with endogenous zymogen with a wild-type cleavage site, the novel engineered zymogen exhibited, surprisingly, improved host cell recovery, improved host cell doubling times and cell viability, and improved specific production of the zymogen. Additionally, the recombinant zymogen may be "charged" with metal ions that increase and prolong its enzymatic activity. The mature recombinant metalloproteinase (mature activator) may be used to activate a thrombin precursor to form active thrombin. In the case of prothrombin, it is brought into contact with the mature activator, which cleaves the prothrombin to yield meizothrombin, which is then autocatalytically processed to form thrombin, particularly α-thrombin.

As used herein, the terms "nucleic acid" or "nucleic acid molecule" refer to a deoxyribonucleotide or ribonucleotide polymer in either single- or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. The nucleotide sequence or molecule may also be referred to as a "probe" or a "primer." Some of the nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al., MOLECULAR CLONING: LAB. MANUAL (2d ed., Cold Spring Harbor Lab. Press, NY, 1989), CURRENT PROTOCOLS MOLECULAR BIO (Ausubel et al., eds., John Wiley & Sons, Inc., NY, 1987), and PCR PROTOCOLS: GUIDE TO METHODS & APPLICATIONS (Innis et al., eds. Academic Press, San Diego, Calif., 1990).

Reference to a nucleic acid molecule also includes its complement as determined by the standard Watson-Crick base-pairing rules, with uracil (U) in RNA replacing thymine (T) in DNA, unless the complement is specifically excluded. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety may be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like.

As described herein, the nucleic acid molecules of the invention include DNA in both single-stranded and double-stranded form, as well as the DNA or RNA complement thereof. DNA includes, for example, DNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art.

As used herein, "wild-type activator gene" or "wild-type activator nucleic acid" refers to a sequence of nucleic acid, corresponding to an activator genetic locus in the genome of an organism, that encodes a gene product having an amino acid sequence, corresponding to the genetic locus, that is most commonly found in the natural population of the species of organism (the "most frequent amino acid sequence corresponding to the genetic locus"). A wild-type activator gene may, for example, comprise any naturally-occurring nucleotide sequence encoding the gene product having the most frequent amino acid sequence corresponding to the genetic locus. In addition, due to the degeneracy of the genetic code, wild-type activator genes may comprise other, non-naturally-occurring nucleotide sequences encoding the most frequent amino acid sequence corresponding to the genetic locus.

The nucleic acids disclosed herein can be used to create other nucleic acids coding for an activator. For example, the invention provides the addition of a thrombin cleavage site to a wild-type activator nucleic acid molecule. For example, the wild-type activator nucleic acid encodes a prothrombin activator from the Viperidae family, such as the viperinae subfamily, the genus *Echis*, such as ecarin from the species *Echis carinitus*. Alternatively, the wild-type activator nucleic acid can encode a prothrombin activator from the subfamily crotilinae. Examples of other metalloproteinases that can have the thrombin cleavage site engineered into their wild-type sequences include jararhagin from *Bothrops jararaca*; HR1B from *Trimeresurus flavoviridis*; Ht-e from *Crotalus atrox*; protrigramin from *Trimeresurus gramineus*; prorhodostomin from *Calloselasma rhodostoma*; and RVVh from Russell's viper venom. See, e.g., Nishida et al., 34(5) Biochem. 1771-78 (1995).

As used herein a "nucleotide probe" or "probe" is defined as an oligonucleotide or polynucleotide capable of binding to a target nucleic acid of complementary sequence through one or more types of chemical bonds, through complementary base pairing, or through hydrogen bond formation. Probes are typically used for identification of target molecules.

As used herein an "oligonucleotide primer pair," "oligonucleotide primer pair member," "oligonucleotide primer member," "oligonucleotide primer," "primer member" or "primer" is defined as an oligonucleotide or polynucleotide capable of binding to a target nucleic acid of complementary sequence through one or more types of chemical bonds, through complementary base pairing, or through hydrogen bond formation. Primers are typically used for amplification of target molecules. It is understood that when discussing oligonucleotide primer pair members in reference to a sequence the primer members are complementary to either the sense or antisense strand, depending on whether the primer member is a 5' (forward) oligonucleotide primer member, or a 3' (reverse) oligonucleotide primer member, respectively. The polynucleotide sequences of oligonucleotide primer members disclosed herein are shown with their sequences reading 5'-3' and thus the 3' primer member is the reverse complement of the actual sequence. Ordinarily skilled artisans in possession of this disclosure will readily design 5' and 3' primer members capable of engineering thrombin cleavage sites into pre-pro-activator molecules.

As used herein, the term "hybridization" or "hybridizes" under certain conditions is intended to describe conditions for hybridization and washes under which nucleotides sharing significantly identical or homologous complementary sequences remain bound to each other. Appropriate hybridization conditions can be selected by those skilled in the art with minimal experimentation as exemplified in Ausubel et al., 1995. Additionally, stringency conditions are described in Sambrook et al., 1989. Variations on the conditions for low, moderate, and high stringency are well known in the art and may be used with the current invention.

A "target nucleic acid" herein refers to a nucleic acid to which a nucleotide primer or probe can specifically hybridize. Probes are designed to determine the presence or absence of the target nucleic acid, and the amount of target nucleic acid. Primers are designed to amplify target nucleic acid sequences. The target nucleic acid has a sequence that is significantly complementary to the nucleic acid sequence of the corresponding probe or primer directed to the target so that the probe or primer and the target nucleic acid can hybridize. Hybridization conditions may be such that hybridization of the probe or primer is specific for the target nucleic acid. As recognized by one of skill in the art, the probe or primer may also contain additional nucleic acids or other moieties, such as labels, which may not specifically hybridize to the target. The term target nucleic acid may refer to the specific nucleotide sequence of a larger nucleic acid to which the probe is directed or to the overall sequence (e.g., gene or mRNA). One skilled in the art will recognize the full utility under various conditions.

A "cloning vector" is a nucleic acid molecule, such as a plasmid, cosmid, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, reference to a nucleic acid "encoding" a protein or polypeptide encompasses not only cDNAs and other intronless nucleic acids, but also DNAs, such as genomic DNA, with introns, on the assumption that the introns included have appropriate splice donor and acceptor sites that will ensure that the introns are spliced out of the corresponding transcript when the transcript is processed in a eukaryotic cell. Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al., 42 Gene 133 (1986); Bauer et al., 37 Gene 73 (1985); Craik, BioTechniques (Jan. 12-19, 1985); Smith et al., GENETIC ENGINEERING: PRINCIPLES & METHODS (Plenum Press, 1981); Kunkel, 82 P.N.A.S. USA 488 (1985); Kunkel et al., 154 Methods in Enzymol. 367 (1987). The present invention thus encompasses any nucleic acid capable of encoding a polypeptide or protein of the current invention.

The current invention provides for isolated polypeptides. As used herein, the term "polypeptides" refers to a genus of polypeptide or peptide fragments that encompass the amino acid sequences identified herein, as well as smaller fragments.

A "protein" is a macromolecule comprising one or more polypeptide chains. A protein may also comprise non-peptidic components, such as carbohydrate groups. Carbohydrates, nucleic acids, and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "wild-type activator polypeptide" or "wild-type activator protein" refers to an activator polypeptide encoded by a wild-type activator gene.

The term "activator" refers to a polypeptide that is capable of cleaving a thrombin precursor molecule to its active thrombin form. Thrombin precursors include, but are not limited to, prothrombin and prethrombin-1 (Foster et al., 26 Biochem. 7003-11 (1987); U.S. Pat. No. 5,476,777). The activator herein may be from the Viperidae family, from the viperinae subfamily, from the genus echis, or may be ecarin from the species *Echis carinitus* (Saw-scaled Viper). Alternatively, the activator is from the subfamily crotilinae. Examples of other metalloprotineases that can have the thrombin cleavage site engineered into their wild type sequences comprise jararhagin from *Bothrops jararaca*; HR1B from *Trimeresurus flavoviridis*; Ht-e from *Crotalus atrox*; protrigramin from *Trimeresurus gramineus*; prorhodostomin from *Calloselasma rhodostoma*; and RVVh from Russell's viper venom. Thus, the term activator further includes the inactive and active forms of the zymogen.

The terms "pre-pro-activator," "inactive activator" or "pro-activator" refer to an activator molecule that includes all or substantially all of the pre-pro leader peptide. Typically, the term pre-pro is used in reference to a zymogen having both a secretion signal and a leader, and the term pro is used when referring to a zymogen having just the leader. For convenience, this distinction is not made herein and the terms may be used interchangeably to refer to the inactive zymogen. Without being bound by theory, it is reported in the literature that ecarin pre-pro- and pro-forms are latent due to the cysteine switch (Van Wart & Birkedal-Hansen, 87 P.N.A.S. USA 5578-82 (1990); Silva et al., 369 Biochem. J. 129-39 (2003)). U.S. Pat. No. 6,413,737 reports an amino acid substitution to eliminate the cysteine switch, thereby making the pre-pro and pro forms active. As the terms pre-pro and pro are used herein, these terms are referring to forms of the zymogen wherein substantially all of the pre-pro polypeptide is present.

The terms "active activator" or "mature activator" refer to an activator molecule that has had all or substantially all of the pre-pro leader peptide(s) removed from the mature sequence, thereby producing a molecule capable of activating other zymogens, such as thrombin precursor zymogens.

The terms "activation site" or "cleavage site" refer to an amino acid sequence of the pre-pro-activator that is typically situated between the pre-pro leader and the mature activator. Activation of the zymogen occurs when substantially all of the pre-pro peptide is removed from the mature activator. Such removal generally takes place by cleavage at the activator site, but cleavage can also occur further upstream (N-terminal of the cleavage site) within the pre-pro-sequence and still produce an active zymogen. For example, in particular embodiments the cleavage site is a thrombin cleavage site; or Gly-Pro-Arg, reading from N-terminus to C-terminus. See e.g., U.S. Pat. No. 5,688,664; WO 03/035861.

The term "heterologous," in particular reference to a polypeptide segment at a modified activation site, means that the polypeptide segment has one or more amino acid substitutions, additions, or deletions relative to the corresponding unmodified activation sequence (i.e., relative to the activator sequence of the wild-type activator polypeptide from which an activator variant is derived).

The term "adjacent," in reference to two linked polypeptide segments, means that the polypeptide segments are non-overlapping and not separated by an intervening segment (e.g., linker).

A polynucleotide or amino acid sequence is "heterologous to" a second sequence if the two sequences are not linked in the same manner as found in naturally-occurring sequences. For example, a promoter operably linked to a heterologous coding sequence refers to a coding sequence which is different from any naturally-occurring allelic variants.

The terms "amino-terminal" (or "N-terminal") and "carboxyl-terminal" (or "C-terminal") are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, a "derivative" is any compound obtained from a known or hypothetical compound and containing essential elements of the parent substance.

As used herein, the term "isolated," in reference to polynucleotides, polypeptides or proteins, means that the polynucleotide, polypeptide or protein is substantially removed from polynucleotides, polypeptides, proteins or other macromolecules with which it, or its analogues, occurs in nature. Although the term "isolated" is not intended to require a specific degree of purity, typically the isolated protein will be at least about 75% pure, at least about 80% pure, at least about 85% pure, at least about 90% pure, at least about 95% pure, or at least about 99% pure.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions. Variants can comprise conservatively substituted sequences, meaning that a given amino acid residue is replaced by a residue having similar physiochemical characteristics. See Zubay, BIOCHEMISTRY (Addison-Wesley Pub. Co., 1983). It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa.

The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments. The effects of such substitutions can be calculated using substitution score matrices such PAM120, PAM-200, and PAM-250 as discussed in Altschul, 219 J. Mol. Biol. 55565 (1991). Other such conservative substitutions, for example, substitutions of entire regions having similar hydrophobicity characteristics, are well known.

Naturally-occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the activator of the invention may be used to attain desired enhancement or reduction in enzymatic activity, modified regiochemistry or stereochemistry, or altered substrate utilization or product distribution. A variant or site directed mutant may be made by any methods known in the art. Variants and derivatives of native polypeptides can be obtained by isolating naturally-occurring variants, or the nucleotide sequence of variants, of other or species, or by artificially programming mutations of nucleotide sequences coding for native activators.

The term "naturally occurring," in the context of activator polypeptides and nucleic acids, means an activator polypeptide or nucleic acid having an amino acid or nucleotide sequence that is found in nature, i.e., an amino acid or nucleotide sequence that can be isolated from a source in nature (an organism) and which has not been intentionally modified by human intervention.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The phrase "substantially identical" means that a relevant sequence is at least 70%, 75%, 80%, 85%, 90%, 92%, 95% 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

"Similarity" or "percent similarity" in the context of two or more polypeptides, refer to two or more amino acid sequences or subsequences that have a specified percentage of amino acid residues that are the same or conservatively substituted when compared and aligned for maximum correspondence. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art.

The term "substantial similarity," in the context of polypeptide sequences, indicates that a polypeptide region has a sequence with at least 70% or at least 75%, typically at least 80% or at least 85%, and more typically at least 85%, at least 90%, or at least 95% sequence similarity to a reference sequence. For example, a polypeptide is substantially similar to a second polypeptide, for example, where the two peptides differ by one or more conservative substitutions.

Numerical ranges recited for purity, similarity and identity are inclusive of all whole (e.g., 70%, 75%, 79%, 87%, 93%, 98%) and partial numbers (e.g., 72.15, 87.27%, 92.83%, 98.11%) embraced within the recited range numbers, therefore forming a part of this description. For example, a polypeptide with 200 residues that share 85% identity with a reference sequence would have 170 identical residues and 30 non-identical residues. Similarly, for example, a polynucleotide with 235 nucleotides may have 200 nucleotide residues that are identical to a reference sequence, thus the polynucleotide will be 85.11% identical to the reference sequence. The terms "at least 80%" and "at least 90%" are also inclusive of all whole or partial numbers within the recited range. For example, at least about 80% pure means that an isolated polypeptide is isolated from other polypeptides, polynucleotides, proteins and macromolecules to a purity of between 80% and 100%, the range being all inclusive of the whole and partial numbers. Thus, 82.5% pure and 91% pure both fall within this purity range. As is used herein, the terms "greater than 95% identical" or "greater than 95% identity" means that a polypeptide, for example, shares 95.01%-100% sequence identity with a reference sequence. This range is all inclusive as described immediately above. Those ordinarily skilled in the art will readily calculate percent purity, percent similarity and percent identity.

The determination of percent identity or percent similarity between two sequences can be accomplished using a mathematical algorithm. A non-limiting example of a mathematical algorithm utilized for the comparison of two sequences is the algorithm of Karlin and Altschul (87 P.N.A.S. USA 2264-68 (1990)), modified as in Karlin and Altschul (90 P.N.A.S. USA 5873-77 (1993)). Such an algorithm is incorporated into the NBLAST and XBLAST programs of Altschul et al. (215 J. Mol. Biol. 403-10 (1990)). BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al. (25 Nucleic Acids Res. 3389-402 (1997)). Alternatively, PSI-Blast can be used to perform an iterated search which detects distant relationships between molecules (id.). When utilizing BLAST, Gapped BLAST, and PSI-Blast programs, the default parameters of the respective programs (e.g., XBLAST and NBLAST) can be used. See, e.g., the National Center for Biotechnology Information (NCBI) website.

Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (10 Comput. Appl. Biosci. 3-5 (1994)); and FASTA described in Pearson and Lipman (85 P.N.A.S. USA 2444-48 (1988)). Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. A further description of FASTA parameters is available on-line thru the Bioweb site. Alternatively, protein sequence alignment may be carried out using the CLUSTAL W algorithm, as described elsewhere. Higgins et al., 266 Methods Enzymol. 383-402 (1996).

Due to the imprecision of standard analytical methods, molecular weights and lengths of polymers are understood to be approximate values. When such a value is expressed as "about" X or "approximately" X, the stated value of X will be understood to be accurate to ±10%. Accordingly, unless indicated to the contrary, the numerical parameters set forth in the specification and claims are approximations that may vary depending upon the desired properties sought to be obtained by the present invention. Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements.

Described herein is a new form of recombinant zymogen metalloproteinase wherein the zymogen has been engineered with an exogenous cleavage site. Host cells transfected with an expression construct encoding the novel engineered zymogen were found, surprisingly, to have improved host cell recovery, improved host cell doubling times and cell viability, and improved specific production of the zymogen, as compared to host cells transfected with an expression construct encoding a corresponding wild-type zymogen with the endogenous cleavage site.

The zymogen metalloproteinase may be obtained from the Viperidae family, from the viperinae subfamily, from the genus *Echis*, such as ecarin from the species *carinitus*. Alternatively, the activator is from the subfamily crotilinae. Examples of other metalloprotineases that can have the thrombin cleavage site engineered into their wild-type sequences comprise jararhagin from *Bothrops jararaca*; HR1B from *Trimeresurus flavoviridis*; Ht-e from *Crotalus atrox*; protrigramin from *Trimeresurus gramineus*; prorhodostomin from *Calloselasma rhodostoma*; and RVVh from Russell's viper venom. Nishida et al., 34(5) Biochem. 1771-78 (1995).

Ecarin is a protease isolated from the venom of the Saw-scaled Viper, *Echis carinatus* (Morita et al., 83 J. Biochem. 559-70, (1978)), which specifically activates prothrombin. The action of ecarin on prothrombin is considered to be independent of calcium, phospholipids, and factorV. The complete amino acid sequence of ecarin was deduced from the nucleotide sequence of a cDNA clone isolated by screening a venomous gland cDNA library of Kenyan *E. carinatus*. The cDNA sequence encodes an open reading frame of 616 amino acids with a remarkable sequence homology to the putative precursor protein of trigramin from *Trimeresurus gramineus* venom (61% identity) and a large hemorrhagin, jararhagin, from the pit viper *Bothrops jararaca* venom (62% identity) (Nishida et al., 1995). Thus, ecarin is translated as a precursor protein, which may be processed post-translationally.

The ecarin proprotein, or zyomogen, has a prosequence domain, a metalloproteinase domain, a disintegrin domain, and a Cys-rich domain (Nishida et al., 1995). The prosequence has a "cysteine switch" motif (-Pro-Lys-Met-Cys-Gly-Val-) (SEQ ID NO:104) similar to that involved in the activation of other matrix metalloproteinase zymogens. The processed mature protein consists of 426 amino acid residues (residues 191-616), showing the strongest sequence similarity with that of Russell's viper venom factor X activator (RVV-X) heavy chain (64% identity). The metalloproteinase domain has a typical zinc-chelating sequence (-His-Glu-Xaa-Xaa-His-Xaa-Xaa-Gly-Xaa-Xaa-His-) (SEQ ID NO:105), as found in crayfish astacin. In the disintegrin domain of ecarin, the Arg-Gly-Asp sequence is Arg-Asp-Asp, which differs from the sequence found in the disintegrin domains of RVV-X heavy chain (Arg-Asp-Glu) and a guinea pig sperm fusion protein, PH-30P (Thr-Asp-Glu). Although there are structural relationships among these proteins, each has a unique functional activity.

When the zymogen metalloproteinase is ecarin, the ecarin may have a polypeptide sequence that is substantially similar to the sequence for ecarin derived from Kenyan *E. carinatus* (GenBank Accession No. Q90495.1, gi:27805465; SEQ ID NO:100). Alternatively, the ecarin can have an amino acid sequence that is substantially similar to the sequence for ecarin derived from *E. carinatus leucogaster* (GenBank Accession No. AAN21193.1, gi:23316547; U.S. Pat. No. 6,413,737).

Applicants have discovered, surprisingly, that host cells transfected with an expression construct encoding a pre-pro-activator with a thrombin cleavage site engineered in between the pre-pro leader and mature activator portions of the pre-pro-activator, express higher levels of the pre-pro-activator, have faster recovery times, faster doubling times, and longer viability than do host cells transfected with a pre-pro-activator having the endogenous cleavage site.

Thus, in one embodiment, the invention relates to expression vectors comprising polynucleotides encoding a pre-pro leader, a thrombin cleavage site, and a mature activator. The thrombin cleavage site is located between the pre-pro leader and the mature activator, with the pre-pro-leader being situated at the N-terminal side of the thrombin cleavage site and the mature activator located at its C-terminal side. For example, the pre-pro leader is adjacent to the N-terminal end of the thrombin cleavage site and the mature activator is adjacent the C-terminal end of the thrombin cleavage site. In reference to SEQ ID NO:100, this thrombin cleavage site is at amino acid residues 188-190, and is engineered into said polypeptide by substituting L189P and I190R.

One embodiment provides for an expression vector comprising a polynucleotide encoding a recombinant metalloprotease pre-pro-activator comprising, from an amino-terminal position to a carboxyl-terminal position, a pre-pro leader; a thrombin cleavage site consisting of a glycine, a proline, and an arginine; and a mature activator, wherein the pre-pro leader shares at least 60% sequence identity with the pre-pro leader, or a fragment thereof, from a wild-type metalloprotease pre-pro-activator, and wherein the mature activator shares at least 60% sequence identity with the mature activator from the wild-type metalloprotease pre-pro-activator. In some embodiments, the pre-pro leader shares at least 80%, at least 85%, at least 90%, at least 95%, or at least 99% sequence identity with the pre-pro leader, or a fragment thereof, from the wild-type metalloprotease pre-pro-activator, and/or the mature activator shares at least 80%, at least 85%, at least 90%, at least 95%, or at least 99% sequence identity with the mature activator from the wild-type metalloprotease pre-pro-activator. In specific variations, the pre-pro leader is 100% identical to the pre-pro leader wild-type metalloprotease pre-pro-activator, and/or the mature activator is 100% identical to the mature activator from the wild-type metalloprotease pre-pro-activator.

In some embodiments, the encoded pre-pro-activator comprises, from an amino-terminal position to a carboxyl-terminal position, a pre-pro-leader sharing at least 60% sequence identity with amino acid residues x-187 of SEQ ID NO:100, wherein x is an integer from 1 to 153, inclusive; a thrombin cleavage site consisting of a Gly, a Pro, and an Arg; and a mature activator sharing at least 60% sequence identity with amino acid residues 191-616 of SEQ ID NO:100.

In certain embodiments, the corresponding wild-type metalloproteinase pre-pro-activator is from the Viperidae family, from the viperinae subfamily, or from the genus *Echis*, such as ecarin from the species *E. carinitus*. Alternatively, the wild-type activator is from the subfamily crotilinae. Examples of other metalloproteinases that can have the thrombin cleavage site engineered into their wild-type genes include jararhagin from *Bothrops jararaca*; HR1B from *Trimeresurus flavoviridis*; Ht-e from *Crotalus atrox*; protrigramin from *Trimeresurus gramineus*; prorhodostomin from *Calloselasma rhodostoma*; and RVVh from Russell's viper venom. Nishida et al., 1995.

Further to this aspect of the invention the expression vector encodes a pre-pro-activator sharing at least 90% sequence identity with SEQ ID NO:100; or sharing at least 99% sequence identity with SEQ ID NO:100. It is understood within this disclosure that although the expression vector may encode a pre-pro-activator with a polypeptide having additions, deletions or substitutions relative to SEQ ID NO:100, any encoded pre-pro-activator as encompassed by the present invention has a thrombin cleavage site between the pre-pro leader and the mature activator. Relative to SEQ ID NO:100, that thrombin cleavage site is defined by a Gly residue at position 188, a Pro at 189, and an Arg at 190. It is further understood that in a pre-pro-activator having additions, deletions or substitutions relative to SEQ ID NO:100 the thrombin cleavage site will not necessarily be at amino acid residues 188-190 of the variant polypeptide. This numbering is by reference to SEQ ID NO:100, and is used as a convenient means for referring to the thrombin cleavage site.

Further in this aspect of the embodiment, the expression vector encodes a pre-pro-activator with a pre-pro leader and a mature activator having primary structure sharing 100% sequence identity with SEQ ID NO:100, and this encoded pre-pro-activator has the amino acid sequence identified in residues 1-616 of SEQ ID NO:2.

In a variation of this aspect of the embodiment the expression vector encodes a pre-pro-activator with a pre-pro leader having a sequence that is at least 80%, at least 85%, at least 90%, at least 95%, or at least 99% identical to residues x-187 of SEQ ID NO:100, wherein x is an integer from 1 to 153, inclusive; and with a mature activator having a sequence that is at least 80%, at least 85%, at least 90%, at least 95%, or at least 99% identical to residues 191-616 of SEQ ID NO:100. In one non-limiting example, the encoded pre-pro-activator of this variant aspect has a pre-pro leader having 80% sequence identity to residues 1-187 SEQ ID NO:100 and a mature activator with 99% sequence identity to residues 191 to 616 of SEQ ID NO:100. In another non-limiting example, the encoded pre-pro-activator of this variant aspect has a pre-pro leader with 90% sequence identity to residues 1 to 187 of SEQ ID NO:100 and a mature activator with 80% sequence identity to residues 191 to 616 of SEQ ID NO:100. Within some variations, the expression vector may encode a pre-pro-activator with a pre-pro leader that is at least thirty-five amino acid residues in length. Thus, the pre-pro-leader may begin at any residue corresponding to residues 1-153 of SEQ ID NO:100. One non-limiting example is an expression vector encoding a pre-pro-activator wherein said pre-pro leader is at least thirty-five contiguous amino acid residues from amino acid residue 1 to amino acid residue 187 of SEQ ID NO:100. Another non-limiting example is an expression vector encoding a pre-pro-activator wherein the pre-pro leader is from amino acid residue 153 to amino acid residue 187 of SEQ ID NO:100. Another non-limiting example is an expression vector encoding a pre-pro-activator wherein said pre-pro leader is from amino acid residue 21 to amino acid residue 187 of SEQ ID NO:100. Another non-limiting example is an expression vector encoding a pre-pro-activator wherein said pre-pro leader is from amino acid residue 1 to amino acid residue 187 of SEQ ID NO:100.

In a further aspect of this embodiment, the expression vector encodes a pre-pro-activator further comprising an affinity tag adjacent to the C-terminal end of the pre-pro-activator. The affinity tag may be a histidine tag. Other tags are also contemplated.

In a further aspect of this embodiment, the expression vector comprises polynucleotides encoding a pre-pro-activator wherein said polynucleotide is codon-optimized for expression in microbial expression systems. SEQ IDs NO:1 and NO:3 are non-limiting examples of polynucleotides that have been partially codon-optimized at the R, I, G codons for microbial expression. The polynucleotide depicted in SEQ ID NO:1 encodes the thrombin activation site, and the polynucleotide depicted in SEQ ID NO:3 encodes the endogenous ecarin activation site. The polynucleotide of SEQ ID NO:99 encodes an ecarin zymogen; however, SEQ ID NO:99 is not codon-optimized. Codon-optimization for microbial expression is well-known in the art, and an ordinarily skilled artisan in possession of this disclosure will readily generate polynucleotide sequences encoding the pre-pro-activators of the current invention. In one non-limiting example, the polynucleotide has the sequence of SEQ ID NO:1. In another non-limiting example, the polynucleotide comprises the sequence of nucleotide residues 1 to 1848 of SEQ ID NO:1. In another non-limiting example, the polynucleotide encoding a pre-pro-activator comprises the sequence of nucleotide residues 1 to 1848 of SEQ ID NO:3.

Another embodiment of the present invention provides for the "charging" or "re-charging" of the metalloprotease activator with metal ions required for activity in situations where the activator is lacking such metal ions or loses metal ions. The recombinant activator is typically produced in culture conditions having $Zn^{2+}$, the native metal for the activator, but this native ion may be lost during purification of the protein (such as, e.g., by cation exchange). In such cases, the activator can be recharged with metal ions, including $Cu^{2+}$, $Co^{2+}$, or $Ni^{2+}$. Generally, this method may be performed with a molar excess of metal ions. Thus, this embodiment provides for the treatment of a thrombin activator, such as recombinant ecarin (rEcarin) in solution or immobilized rEcarin, with transition metal ions to place metal into the active site, thereby generating an active rEcarin species. In general, a solution state rEcarin or immobilized rEcarin may be treated with $Cu^{2+}$, $Co^{2+}$, or $Ni^{2+}$. Treated in this fashion, the thrombin activator retains activity under conditions where metal ions may otherwise be washed away, thus the activator retains activity, sometimes superior activity.

In addition to Ecarin (Zinc metalloproteinase-disintegrin ecarin (VMECA_ECHCA)), there are other Zn metalloproteases that may be complexed with a non-zinc transition metal cation such as $Cu^{2+}$, $Co^{2+}$ or $Ni^{2+}$ to yield or recover active metalloproteases. Indeed, this approach may be extended to a variety of metalloproteases comprising a zinc-binding motif, including wild-type metalloproteases as well as variants thereof, to yield the corresponding active enzymatic forms. Treating solution state or immobilized enzyme with buffered solutions of metal ions such as $Cu^{2+}$, $Co^{2+}$ and $Ni^{2+}$ can replenish or replace the metal ion in the enzyme active site. This technique may be extended to preparing the apo-form during cell culture and later activating the protein by adding $Cu^{2+}$, $Co^{2+}$, $Ni^{2+}$ or other metal ion. Preparing the apo-form may allow for higher productivity of an enzyme that would otherwise not be possible due to bioactivity, which may be manifested as a toxicity to the host cell thereby inhibiting growth, replication and/or production of the enzyme.

Thus, in one aspect, the present invention provides an isolated, zinc metalloprotease complexed with a non-zinc transition metal cation such as, for example, $Cu^{2+}$, $Co^{2+}$ or $Ni^{2+}$. Such complexes may include metal cations and Zinc metalloproteinase-disintegrin ecarin precursor (VMECA_ECHCA, designations per Swiss Institute of Bioinformatics, available through the ExPASy organization's web site); Metalloproteinase rhodostoxin/Disintegrin rhodostomin from *Agkistrodon rhodostoma* (DISR_AGKRH); Zinc metalloproteinase-disintegrin BITM06A from *Bothrops insularis* (VM6A_BOTIN); Zinc metalloproteinase-disintegrin bothropasin from *Bothrops jararaca* (VMBOP_BOTJA); Zinc metalloproteinase-disintegrin jararhagin/Disintegrin jararhagin-C from *Bothrops jararaca* (VMJAR_BOTJA); Zinc metalloproteinase-disintegrin of *Crotalus durissus durissus* (VM_CRODD); Zinc metalloproteinase-disintegrin berythractivase from *Bothrops erythromelas* (VMBER_BOTER); Zinc metalloproteinase ACLH from *Agkistrodon contortrix laticinctus* (VMACH_AGKCL); Zinc metalloproteinase-disintegrin ACLD, also from *Agkistrodon contortrix laticinctus* (VMED_AGKCL); Zinc metalloproteinase-disintegrin/Metalloproteinase Mt-b, from *Agkistrodon halys brevicaudus* (VMMTB_AGKHB); Zinc metalloproteinase Bap1 from *Bothrops aper* (VMBP1_BOTAS); Zinc metalloproteinase-disintegrin Eoc1 from *Echis ocellatus* (VM1_ECHOC); Zinc metalloproteinase-disintegrin bilitoxin-1 from *Agkistrodon bilineatus* (VMBI1_AGKBI); Zinc metalloproteinase neuwiedase from *Bothrops newiedi pauloensis* (VM-NEU_BOTNE); Zinc metalloprotease-disintegrin halysase from *Agkistrodon halys pallas* (VMHA_AGKHP); Zinc metalloproteinase-disintegrin VLAIP-A from *Vipera lebetina* (VMIPA_VIPLE); Zinc metalloproteinase-disintegrin HF3 from *Bothrops jararaca* (VMHF3_BOTJA); Zinc metalloproteinase-disintegrin VLAIP-B from *Vipera lebetina* (VMIPB_VIPLE); A disintegrin and metalloproteinase domain 25/ADAM 25 from *Mus musculus* (ADA25_MOUSE); A disintegrin and metalloproteinase domain 26/ADAM 26A from *Mus musculus* (AD26A_MOUSE); A disintegrin and metalloproteinase domain 9/ADAM 9 from *Homo sapiens* (ADAM9_HUMAN); or A disintegrin and metalloproteinase domain 21/ADAM 21 (ADA21_HUMAN). In some embodiments, the metalloprotease comprises an amino acid sequence having at least 95% sequence identity (e.g., 100% sequence identity) with the amino acid sequence shown in residues 191-616 of SEQ ID NO:100.

In a related aspect, the present invention provides a method for activating a zinc metalloprotease where transition metal ions, such as native Zn cations, have been at least partially depleted from the active site of the enzyme. The method generally includes contacting the zinc metalloprotease with a solution containing a non-zinc transitional metal cation such as, for example, $Cu^{2+}$, $Co^{2+}$, or $Ni^{2+}$. Typically, the zinc metalloprotease comprises a zinc-binding active site containing the motif $Xaa_1$-His-Glu-$Xaa_2$-$Xaa_3$-His-$Xaa_4$-$Xaa_5$-Gly-$Xaa_6$-$Xaa_7$-His-$Xaa_8$ (SEQ ID NO:102). In certain embodiments where the zinc metalloprotease comprises the aforementioned motif, $Xaa_1$ is Ala, $Xaa_3$ is Gly, and $Xaa_8$ is Asp (thereby yielding a zinc-binding motif having the sequence Ala-His-Glu-$Xaa_2$-Gly-His-$Xaa_4$-$Xaa_5$-Gly-$Xaa_6$-$Xaa_7$-His-Asp (SEQ ID NO:103). In specific variations, the metalloprotease is selected from the group consisting of Zinc metalloproteinase-disintegrin ecarin (VMECA_ECHCA); Disintegrin rhodostomin (DISR_AGKRH); Zinc metalloproteinase-disintegrin BITM06A (VM6A_BOTIN); Zinc metalloproteinase-disintegrin bothropasin (VMBOP_BOTJA); Zinc metalloproteinase-disintegrin jararhagin (VMJAR_BOTJA); Zinc metalloproteinase-disintegrin (VM_CRODD); Zinc metalloproteinase-disintegrin berythractivase (VMBER_BOTER); Zinc metalloproteinase ACLH (VMACH_AGKCL); Zinc metalloproteinase-disintegrin ACLD (VMED_AGKCL); Zinc metalloproteinase-disintegrin (VMMTB_AGKHB); Zinc metalloproteinase Bap1 (VMBP1—BOTAS); Zinc metalloproteinase-disintegrin Eoc1 (VM1_ECHOC); Zinc metalloproteinase-disintegrin bilitoxin-1 (VMBI1_AGKBI); Zinc metalloproteinase neuwiedase (VMNEU_BOTNE); Zinc metalloprotease-disintegrin halysase (VMHA_AGKHP); Zinc metalloproteinase-disintegrin VLAIP-A (VMIPA_VIPLE); Zinc metalloproteinase-disintegrin HF3 (VMHF3_BOTJA); Zinc metalloproteinase-disintegrin VLAIP-B (VMIPB_VIPLE); ADAM 25 (ADA25_MOUSE); ADAM 26A (AD26A_MOUSE); ADAM 9 (ADAM9_HUMAN); and ADAM 21 (ADA21_HUMAN). In some embodiments, the metalloprotease comprises an amino acid sequence having at least 95% sequence identity (e.g., 100% sequence identity) with the amino acid sequence shown in residues 191-616 of SEQ ID NO:100.

Another aspect of the present invention provides for an isolated oligonucleotide primer pair member for engineering a thrombin cleavage site into a pre-pro-activator, wherein the oligonucleotides primer pair member contains a sequence complementary to a pre-pro sequence adjacent to a thrombin cleavage site sequence adjacent to a mature activator sequence. In one aspect of this embodiment, the oligonucleotide primer pair member is the 3' member. In another aspect of this embodiment, the oligonucleotide primer pair member is the 5' member. In a further aspect of the embodiment, the oligonucleotide primer pair member is sixty consecutive nucleotides in length. In a still further aspect of this embodiment, the pre-pro and the mature activator oligonucleotide primer pair member is complementary to a pre-pro-activator selected from the group consisting of: ecarin from Kenyan *E. carinatus*, ecarin from *E. carinatus leucogaster*, jararhagin from *B. jararaca*; HR1B from *T. flavoviridis*; Ht-e from *C. atrox*; protrigramin from *T. gramineus*; prorhodostomin from *C. rhodostoma*; and RVVh from Russell's viper venom. The oligonucleotide primer pair member may be complementary to ecarin from Kenyan *E. carinatus*, complementary to a pre-pro-activator with at least 90% sequence identity with SEQ ID NO:99, complementary to SEQ ID NO:99, or the oligonucleotide primer pair member may have the sequence of SEQ ID NO: 97.

Another aspect of this embodiment provides for an isolated oligonucleotide primer pair for engineering a thrombin cleavage site into a pre-pro-activator, wherein one member of said oligonucleotide primer pair comprises a sequence complementary to a pre-pro leader sequence and the second member comprises a sequence complementary to a mature activator, and wherein each primer member has a sequence complementary to a thrombin cleavage site adjacent and in correct orientation to engineer a thrombin cleavage site into a pre-pro-activator. In one non-limiting example, a first primer member of said oligonucleotide primer pair members has a sequence complementary to a pre-pro-leader from a pre-pro-activator with at least 90% sequence identity with SEQ ID NO:99 adjacent to a sequence complementary to a sequence of a thrombin cleavage site, and a second primer member of said oligonucleotide primer pair members has a sequence complementary to a mature activator from a pre-pro-activator with at least 90% sequence identity with SEQ ID NO:99 adjacent to a polynucleotide having sequence complementary to that of a thrombin cleavage site. Each of said first and second primer members independently may comprise all or a portion of a sequence complementary to a thrombin cleavage site. Thus, in another non-limiting example of this aspect, a first primer member of said oligonucleotide primer pair members has a sequence complementary to a pre-pro-leader sequence from a pre-pro-activator with at least 85% sequence identity with SEQ ID NO:99 adjacent to a sequence complementary to six of the nine polynucleotide residues encoding for a thrombin cleavage site, and a second primer member of said oligonucleotide primer pair members comprises a sequence complementary to a mature activator sequence from a pre-pro-activator with at least 85% sequence identity with SEQ ID NO:99 adjacent to a sequence complementary to seven of the nine polynucleotide residues encoding a thrombin cleavage site.

It is understood that when discussing oligonucleotide primer pair members in reference to a sequence, the primer members are complementary to either the sense or antisense strand, depending on whether the primer member is a 5' (forward) oligonucleotide primer member, or a 3' (reverse) oligonucleotide primer member, respectively. Ordinarily skilled artisans in possession of this disclosure will readily design 5' and 3' primer members capable of engineering thrombin cleavage sites into pre-pro-activator molecules.

A further embodiment provides for a method of producing a pre-pro-activator comprising the steps of: (a) transfecting a host cell with an expression vector comprising a polynucleotide encoding a pre-pro-activator, wherein said encoded pre-pro-activator comprises, from an amino-terminal position to a carboxyl-terminal position, a pre-pro-leader sharing at least 60% sequence identity with amino acid residues x-187 of SEQ ID NO:100, wherein x is an integer from 1 to 153, inclusive; a thrombin cleavage site consisting of a Gly, a Pro, and an Arg; and a mature activator sharing at least 60% sequence identity with amino acid residues 191-616 of SEQ ID NO:100; (b) expressing a pre-pro-activator from said expression vector; and (c) recovering expressed pre-pro-activator. The pre-pro-activator may be from the Viperidae family, such as pre-pro-activator ecarin from Kenyan *Echis carinatus*, or the encoded pre-pro-activator shares at least 90% sequence identity with SEQ ID NO:100, or the pre-pro-activator shares at least 99% sequence identity with SEQ ID NO:100. In some variations, the pre-pro leader has the amino acid sequence shown in residues 1-187 of SEQ ID NO:100 and the mature activator has the amino acid sequence shown in residues 191-616 of SEQ ID NO:100. In a specific embodiment, the encoded pre-pro-activator comprises the amino acid sequence shown in residues 1-616 of SEQ ID NO:2.

In certain variations, the expression vector encodes a pre-pro-activator with a pre-pro leader having a sequence that is at least 80%, at least 85%, at least 90%, at least 95%, or at least 99% identical to residues x-187 of SEQ ID NO:100 wherein x is an integer from 1 to 153, inclusive; and with a mature activator sequence that is at least 80%, at least 85%, at least 90%, at least 95%, or at least 99% identical to residues 191-616 of SEQ ID NO:100. One non-limiting example the encoded pre-pro-activator of this variant aspect has a pre-pro leader with 80% sequence identity to residues 1-187 of SEQ ID NO:100 and a mature activator with 99% sequence identity to residues 191-616 of SEQ ID NO:100. Another non-limiting example the encoded pre-pro-activator of this variant aspect has a pre-pro leader with 90% sequence identity to residues 1-187 of SEQ ID NO:100 and a mature activator with 80% sequence identity to residues 191-616 of SEQ ID NO:100. Within some variations, the expression vector may encode a pre-pro-activator with a pre-pro leader that is at least 35 amino acid residues in length. Thus, in such variations, the pre-pro-leader may begin at any residue corresponding to residues 1-153 of SEQ ID NO:100. One non-limiting example is an expression vector encoding a pre-pro-activator wherein the pre-pro leader comprises at least thirty-five contiguous amino acid residues from amino acid residue 1-187 of SEQ ID NO:100. Another non-limiting example is an expression vector encoding a pre-pro-activator wherein said pre-pro leader is from amino acid residue 153-187 of SEQ ID NO:100. Another non-limiting example is an expression vector encoding a pre-pro-activator wherein said pre-pro leader is from amino acid residue 21-187 of SEQ ID NO:100. Another non-limiting example is an expression vector encoding a pre-pro-activator wherein the pre-pro leader is from amino acid residue 1-187 of SEQ ID NO:100.

In a further aspect of this embodiment, the expression vector encodes a pre-pro-activator further comprising an affinity tag adjacent to the C-terminal end of said pre-pro-activator, such as a histidine tag. Other tags are also contemplated.

In a further aspect of this embodiment the expression vector comprises polynucleotide sequence encoding a pre-pro-activator wherein said polynucleotide sequence is codon optimized for expression in microbial expression systems. SEQ ID NO:1 and NO:3 are non-limiting examples polynucleotide sequences that have been codon optimized for microbial expression. SEQ ID NO:1 encodes the thrombin activation site, and SEQ ID NO:3 encodes endogenous ecarin and its activation site. In comparison, the molecule having the sequence of SEQ ID NO:99 is not codon optimized. Codon optimization for microbial expression is well known in the art and an ordinarily skilled artisan in possession of this disclosure will readily generate polynucleotide sequences encoding the pre-pro-activators of this current invention. In one non-limiting example, said polynucleotide sequence comprises nucleotide residues 1-1848 of SEQ ID NO:1. In another non-limiting example, said polynucleotide sequence encoding a pre-pro-activator comprises nucleotide residues 1-1848 of SEQ ID NO:3.

In a further aspect of this embodiment, said host cell may be a mammalian cell line, such as a hamster cell line, e.g., a Chinese Hamster Ovary cell line such as DXB11.

In a variant aspect of this embodiment the method further comprises the step of: (d) activating said recovered pre-pro-activator. The activation step may use heat, small molecule activators, enzyme activation such as trypsin activation or thrombin activation.

Methods steps need not necessarily be performed in the order described herein. For example, and not limitation, the just previously described activation step need not take place following the recovery step, and in fact, the zymogen molecule can be activated before recovery. In such an instance an activator can be included in the culture medium wherein the pre-pro-activator will become activated, followed by a recovery step. Alternatively, activation can take place by co-expression of an activator of the pre-pro-activator by said host cell. The activator can be endogenous to the host cell; such as when the activator is recombinantly expressed by the host cell. For example, in some CHO cell culture there is partial activation of ecarin and ecarin-like zymogens by an endogenous CHO cell protease.

In a further aspect of this embodiment there is provided an isolated pre-pro-activator with a sequence that is at least 90% identical the polypeptide sequence of SEQ ID NO:2, or at least 99% identical the polypeptide sequence of SEQ ID NO:2, or corresponds to amino acid residues 153-616 or 153-622 of SEQ ID NO:2, or has a sequence identical to that of residues 1-616 or 1-622 of SEQ ID NO:2.

In a further aspect of this embodiment there is provided an isolated mature activator polypeptide with a sequence that is at least 90% identical to the mature activator sequence of SEQ ID NO:2, or at least 99% identical to the mature activator shown in SEQ ID NO:2, or corresponds to amino acid residues 118-616 or 188-622 of SEQ ID NO:2, residues 189-622 or 189-622 of SEQ ID NO:2, residues 190-622 of SEQ ID NO:2, or is 100% identical to the mature activator having the sequence of SEQ ID NO:2.

In another embodiment there is provided methods for making mature thrombin, comprising treating a thrombin precursor with mature activator. The thrombin may be treated in vitro with the mature activator or during production by co-expression with the pre-pro-activator. In one aspect, the mature activator is brought into contact with a thrombin precursor molecule under conditions suitable for activation of the thrombin precursor to thrombin by a mature activator. The conditions may allow the mature activator and the thrombin precursor to come in sufficient contact to allow activation of the thrombin precursor. For example, the mature activator may immobilized to a resin and packed into a column and a thrombin precursor is passed through said column for a sufficient amount of time and in a buffer that is suitable to allow the mature activator to cleave the thrombin precursor to thrombin. In one embodiment, said buffer comprise a zinc cofactor, a copper cofactor, a nickel cofactor or combinations thereof. For example, immobilized mature activator can be charged using a transition metal ion such as zinc, nickel and, preferably, copper.

In a further aspect of this embodiment the mature activator sequence may be at least 90% identical to the mature activator having the sequence of SEQ ID NO:2, or may be 100% identical to the mature activator having the sequence of SEQ ID NO:2, or corresponds to amino acid residues 188 to 622 of SEQ ID NO:2, residues 189 to 622 of SEQ ID NO:2, residues 190 to 622 of SEQ ID NO:2, residues 188 to 616 of SEQ ID NO:2, residues 189 to 616 of SEQ ID NO:2, residues 190 to 616 of SEQ ID NO:2, or residues 191 to 616 of SEQ ID NO:2.

In a variant aspect of this embodiment, the invention provides methods of cleaving proteins, such as genetically engineered fusion proteins, containing an ecarin recognition site. The site may be naturally occurring, or the protein may be engineered to contain an ecarin cleavage site.

The new form of these zymogen metalloproteinases replaces the endogenous cleavage site between the pre-pro-activator sequence and the mature activator sequence with a thrombin cleavage site. Referring to the ecarin protein sequence disclosed in SEQ ID NO:100, residues 189 and 190 are substituted to L189P and I190R, thereby engineering in a thrombin cleavage site (Gly Pro Arg) at residues 188-190 as shown in SEQ ID NO:2. Addition of the thrombin cleavage site to the pre-pro-activator is beneficial, as the chimeric molecule is then more highly expressed and the recombinant host cells have increased recovery time, doubling time and overall viability. As a result, these unexpected benefits provide a recombinant cell that on average will produce far more pre-pro-activator molecules in its lifetime than a counterpart cell expressing a zymogen without the thrombin cleavage site.

Pre-pro-activator is preferably produced by recombinant means. Recombinant expression generally involves the creation of an expression vector which contains DNA encoding an activator of the invention, operably linked to other sequences necessary for expression of the pre-pro-activator ("control elements"). Operable linkage between a pre-pro activator gene and a control element requires that the two sequences be in proper orientation and in sufficient proximity for the control sequences to function as intended. The details of an operable linkage between sequence elements will vary according to the exact identity and properties of the sequences, as will be apparent to one of skill in the art. The expression vector is transferred into a host cell, which is cultured and, if necessary, manipulated to induce expression of the pre-pro-activator.

Precise details of the expression vector will vary according to the particular host cell that is to be used as well as to the desired characteristics of the expression system, as is well known in the art. For example, for production in *S. cerevisiae*, the DNA encoding a pre-pro-activator is placed into operable linkage with a promoter that is operable in *S. cerevisiae* and which has the desired characteristics (e.g., inducible/derepressible or constitutive), such as GAL1-10, PHO5, PGK1, GDP1, PMA1, MET3, CUP1, GAP, TPI, MFα1 and MFα2, as well as the hybrid promoters PGK/α2, TPI/α2, GAP/GAL, PGK/GAL, GAP/ADH2, GAP/PHO5, ADH2/PHO5, CYC1/GRE, and PGK/ARE and other promoters known in the art. Where bacterial host cells are utilized, promoters and promoter/operators such as the araB, trp, lac, gal, tac (a hybrid of the trp and lac promoter/operator), T7, and the like are useful. When other eukaryotic cells are the desired host cell, any promoter active in the host cell may be utilized. For example, when the desired host cell is a mammalian cell line, the promoter may be a viral promoter/enhancer (e.g., the herpes virus thymidine kinase (TK) promoter or a simian virus promoter (e.g., the SV40 early or late promoter) or the Adenovirus major late promoter, a long terminal repeat (LTR), such as the LTR from cytomegalovirus-(CMV), Rous sarcoma virus (RSV), chicken .beta.actin promoter or mouse mammary tumor virus (MMTV)) or a mammalian promoter, preferably an inducible promoter such as the metallothionein or glucocorticoid receptor promoters and the like.

Expression vectors may also include other DNA sequences appropriate for the intended host cell. For example, expression vectors for use in higher eukaryotic cell lines (e.g., vertebrate and insect cell lines) will include a poly-adenylation site and may include an intron (including signals for processing the intron), as the presence of an intron appears to increase mRNA export from the nucleus in many systems. Additionally, a secretion signal sequence operable in the host cell is normally included as part of the vector. The secretion signal sequence may be the naturally occurring ecarin signal sequence from *E. carinatus* ecarin, or it may be derived from another gene, such as human serum albumin, human pro-thrombin, human tissue plasminogen activator, or preproinsulin. Where the expression vector is intended for use in a prokaryotic cell, the expression vector may include a signal sequence which directs transport of the synthesized peptide into the periplasmic space or expression may be directed intracellularly.

Preferably, the expression vector will also comprise a means for selecting for host cells which contain the expression vector (a "selectable marker"). Selectable markers are well known in the art. For example, the selectable marker may be a resistance gene, such as a antibiotic resistance gene (e.g., the $neo^R$ gene which confers resistance to the antibiotic gentamycin or the $hyg^R$ gene, which confers resistance to the antibiotic hygromycin), or it may be a gene which complements an auxotrophy of the host cell. If the host cell is a Chinese hamster ovary (CHO) cell which lacks the dihydrofolate reductase (dhfr) gene, for example CHO DXB11 cells, a complementing dhfr gene would be preferred.

If the host cell is a yeast cell, the selectable marker is preferably a gene which complements an auxotrophy of the cell (for example, complementing genes useful in *S. cerevisiae*, *P. pastoris* and *S. pombe* include LEU2, TRP1, TRP1d, URA3, URA3d, HIS3, HIS4, ARG4, LEU2d), although antibiotic resistance markers such as SH BLE, which confers resistance to Zeocin™ (phleomycin, Invitrogen), may also be used. If the host cell is a prokaryotic or higher eukaryotic cell, the selectable marker is preferably an antibiotic resistance marker (e.g., $neo^R$). Alternatively, a separate selectable marker gene is not included in the expression vector, and the host cells are screened for the expression of pre-pro activator (e.g., upon induction or depression for controllable promoters, or after transfection for a constitutive promoter, fluorescence-activated cell sorting, FACS, may be used to select those cells which express the recombinant pre-pro-activator). Preferably, the expression vector comprises a separate selectable marker gene.

The expression vector may also contain sequences which act as an "ARS" (autonomous replicating sequence) which will allow the expression vector to replicate in the host cell without being integrated into the host cell chromosome. Origins of replication for bacterial plasmids are well known. ARS for use in yeast cells are also well known (e.g., the 2μ origin of replication and operative fragments thereof) and ARS which act in higher mammalian cells have been described. See, e.g., Pelletier et al., 66(1) J. Cell. Biochem. 87-97 (1997). Alternately, the expression vector may be integrated into the host cell chromosome. The integration may be by random insertion, or the expression vector may include DNA sequences which will direct or allow the integration of the construct into the host cell chromosome by homologous or site-directed recombination.

Where the host cell is a eukaryotic cell, it may be advantageous for the expression vector to be a "shuttle vector", because manipulation of DNA is substantially more convenient in bacterial cells. A shuttle vector is one which carries the necessary signals for manipulation in bacteria as well as the desired host cell. So, for example, the expression vector may also comprise an ARS ("ori") which acts in prokaryotic cells as well as a selectable marker which is useful for selection of prokaryotic cells.

The host cells for use in the instant invention may be any convenient host cell, including bacterial, yeast, and eukaryotic cells. Higher eukaryotic cells are example host cells. Examples of yeast host cells include, *Saccharomyces cerevisiae, Pichia pastoris, Hansenula polymorpha, Kluyveromyces lactis, Schwanniomyces occidentis, Schizosaccharomyces pombe* and *Yarrowia lipolytica* strains. Of the higher eukaryotic cells include insect cells such as Sf9, and mammalian cell lines such as CHO, COS, 293, 293-EBNA, baby hamster kidney (BHK), HeLa, NIH/3T3, and the like.

The expression vector is introduced into the host cells by any convenient method known to the art. For example, for yeast host cells, the construct may be introduced by electroporation, lithium acetate/PEG and other methods known in the art. Higher eukaryotes may be transformed by electroporation, microprojectile bombardment, calcium phosphate transfection, lipofection, or any other method known to the art. Bacterial host cells may be transfected by electroporation, calcium chloride-mediated transfection, or any other method known in the art. Transfection may be transient or stable. Transient transfection systems include, but are not limited to the T-Rex system (Invitrogen, Cat. #K9000-01; #K1030-02).

After introduction of the expression vector into the host cell, host cells comprising the expression vector are normally selected on the basis of the selectable marker that is included in the expression vector. As will be apparent, the exact details of the selection process will depend on the identity of the selectable marker. If the selectable marker is an antibiotic resistance gene, the transfected host cell population is generally cultured in the presence of an antibiotic to which resistance is conferred by the selectable marker. The antibiotic eliminates those cells which are not resistant (i.e., those cells which do not carry the resistance gene) and allows the propagation of those host cells which carry the resistance gene. If the selectable marker is a gene which complements an auxotrophy of the host cells, then the transfected host cell population is cultured in the absence of the compound for which the host cells are auxotrophic. Those cells which are able to propagate under these conditions carry the complementing gene to supply this compound and thus presumably carry the rest of the expression vector. The selection procedure may use methotrexate to select for host cells transformed with an expression vector in which both the dhfr and the target gene are co-amplified.

Host cells which pass the selection process may be "cloned" according to any method known in the art that is appropriate for the host cell. For microbial host cells such as yeast and bacteria, the selected cells may be plated on solid media under selection conditions, and single clones may be selected for further selection, characterization or use. Higher eukaryotic cells are generally further cloned by limiting dilution (although physical isolation methods such as micromanipulation or "cloning rings" may also be used). This process may be carried out several times to ensure the stability of the expression vector within the host cell.

For production of pre-pro-activator, the recombinant host cells comprising the expression vectors are generally cultured to expand cell numbers. This expansion process may be carried out in any appropriate culturing apparatus known to the art. For yeast and bacterial cells, an apparatus as simple as a shaken culture flask may be used, although large scale culture is generally carried out in a fermenter. For insect cells, the culture is generally carried out in "spinner flasks" (culture vessels comprising a means for stirring the cells suspended in a liquid culture medium). For yeast and bacterial host cells, large scale culture is generally performed in a specially adapted apparatus, a variety of which are known in the art. Mammalian cell lines can be grown in a variety of different culture configurations, ranging from simple culture plates or flasks, to roller bottles, to more sophisticated apparati such as hollow fiber cartridges and suspended microbead systems.

The culture medium used for culture of the recombinant host cells will depend on the identity of the host cell. Culture media for the various host cells used for recombinant culture are well known in the art. The culture medium generally comprises inorganic salts and compounds, amino acids, carbohydrates, vitamins and other compounds which are either necessary for the growth of the host cells or which improve the health and/or growth of the host cells (e.g., protein growth factors and hormones where the host cells are mammalian cell lines). For the culture of mammalian host cell lines, the use of animal products (e.g., serum) is preferably avoided. Semi-defined media and defined media are preferred for use herein.

The recombinant host cells are cultured under conditions appropriate for the expression of the DNA encoding the pre-pro-activator. Constitutive promoters or inducible promoters can be used with the current expression vector. With inducible promoters, the exact method of inducing or depressing the expression of the DNA encoding pre-pro-activator will depend on the properties of the particular expression vector used and the identity of the host cell, as will be apparent to one of skill in the art. If the expression vector utilizes a controllable expression system, the expression of the DNA encoding the ecarin of the invention is induced or depressed, as is appropriate for the particular expression vector. Generally, for inducible promoters, a molecule which induces expression is added to the culture medium. For example, for a mammalian cell line transformed with an expression vector utilizing the metallothionein promoter, a metal, such as zinc, is added to the culture medium. In bacteria utilizing an expression vector with the lac promoter, isopropyl-β-D-thiogalactopyranoside (IPTG) is added to the medium to depress expression. For constitutive promoters, the cells are cultured in a medium providing the appropriate environment and sufficient nutrients to support the survival of the cells.

Recombinantly produced pre-pro-activator may be purified by conventional chromatographic techniques for example using wheat germ lectin SEPHAROSE® (Amersham Pharmacia Biotech, Piscataway, N.J.). The pre-pro-activator bound to the resin may be eluted by exposure to N-acetyl-D-glucosamine. Fortova et al., 260 J. Chrom. 522-26 (1983). Alternatively the pre-pro-activator may be purified by immobilized metal affinity chromatography (the catalytic domain of metalloproteinases contain a metal binding motif, typically the zinc binding motif HEXXHXXGXXH) using resin such as chelate SEPHAROSE® charged with metal ions such as zinc, nickel, cobalt and the like. Other chromatography resins such as ion exchange (Q- and SP-SEPHAROSE®), affinity (Cibacron Blue-SEPHAROSE®), Toyopearl AF-Heparin HC® and various gel filtration resins will also be effective for purifying pre-pro-activator. Rhee et al., 1982; Morita et al., 83 J. Biochem. 559-70 (1978).

Mature activators may be used for proteolytic processing of proteins containing an appropriate recognition site. Preferably, the mature activator is substantially similar to ecarin. The substrate protein's ecarin recognition site may be endogenous, as in the case of thrombin precursor molecules, or it may as a result of genetic engineering (e.g., a recombinant fusion protein which has been engineered to add an ecarin recognition site). The results of proteolytic processing will, of course, depend on the identity and properties of the protein that is processed with the mature activator. When the protein processed by a mature activator is a fusion protein containing an appropriate recognition site at the link between the fusion partners, proteolytic processing results in liberation of the fusion partners from the fusion protein. Such processing may be desirable for the production of recombinant proteins when a fusion partner is necessary for or enhances production of the fusion protein, but is not desired in the final product. In the case of thrombin precursors, processing with ecarin results in the production of thrombin. Activation of a thrombin precursor by ecarin is well characterized, and is even the basis of certain diagnostic assays for tracking anticoagulant therapy. Dyr et al., 30(3) Thromb. Res. 225-34 (1983); Potzsch et al., 86(5) Thromb. Res. 373-83 (1997).

One common method of activating the pre-pro-activators to mature activators is treatment with an organomercurial such as p-aminophenylmercuric acetate (APMA). APMA facilitates the loss of the enzyme propeptide domain through an autolytic cleavage known as the cysteine switch. Other useful agents include, but are not limited to, organomercurials such as o-[(3-hydroxymercuri-2-methoxypropyl)carbamoyl] phenoxyacetic acid (Mersalyl), p-(hydroxymercuric)benzoate (PHMB), phenylmercuric chloride (PMC) and mercuric chloride ($HgCl_2$), as well as oxidized glutathlione/glutatnione disulfide (GSSG), N-ethylmaleimide (NEM), 5,5'-dithiobis(2-nitrobenzoic acid) (DTNB), sodium thiocyanate (NaSCN), and sodium chlorate ($NaClO_3$). In a particular embodiment, the pre-pro-activators described herein are activated by treatment with a protease, such as thrombin or trypsin.

Mature activator may be used to activate a thrombin precursor to form active thrombin. In the case of prothrombin, it is brought into contact with the mature activator, which cleaves the prothrombin to yield meizothrombin, which is then autocatalytically processed to form thrombin, particularly α-thrombin. Reaction conditions for activating prothrombin are well known in the art, and need not be described in detail here.

Proteins are proteolytically processed with mature activator by exposing the protein to be processed to said mature activator under conditions which favor the activity of said mature activator, for example, 20 mM Tris-HCl pH 8.4, 0.1 M NaCl, 0.2% PEG1000. The presence of divalent cations is not required, however the charging or recharging of the mature activator with ions such as $Cu^{2+}$, $Ni^{2+}$, or $Co^{2+}$ have been found to enhance and/or prolong activity. The protein to be processed can be exposed to a mature activator in solution. In this embodiment, the protein to be processed (which may be crude, such as a cell extract, conditioned media, partially pure, or purified) is mixed in solution with a mature activator. The mixture of mature activator and the protein to be processed is incubated for a period of time, and then may be further processed to remove the mature activator and/or purify the processed protein. Alternatively, the protein to be processed is exposed to an immobilized mature activator. Generally, the mature activator is bound to an insoluble support, such as a membrane, particles (e.g., beads), or a vessel wall. Suitable insoluble supports include glass, polystyrene, polypropylene, polyethylene, dextran, nylon, amylase, natural and modified cellulose, polyacrylamide, agarose, modified agarose (e.g., crosslinked) and magnetite. Preferred supports include agarose, modified agarose (e.g., SEPHAROSE®), cellulose and modified cellulose. The mature activator may be immobilized by a covalent linkage, such as by use of an activated support (e.g., CNBr-activated or NHS-activated) or it may be non-covalently associated. Non-covalent association is usually by means of a binding pair. For example, the mature activator may be derivatized with a molecule such as biotin, which is strongly bound by avidin and streptavidin, and so would become non-covalently bound to a support comprising avidin or streptavidin. Fusion proteins which fuse one half of a binding pair to the mature activator are also useful in this embodiment. For example, a poly-histidine "tag" may be fused to the mature activator, and bound to a metal chelating column loaded with a metal such as zinc or nickel. These and other methods for covalently and non-covalently attaching a protein of interest to a support are well known in the art, and are thus not described in detail here. Thrombin precursors or any other protein containing a mature activator recognition site may be exposed to the immobilized mature activator by contacting a solution containing the protein of interest (e.g., prothrombin or a protein containing an ecarin recognition site) with the immobilized mature activator.

EXAMPLES

The following non-limiting examples are useful in describing the compositions and methods of the current invention.

Example 1

Assembly of the Pre-Pro-Activator and Construction of a Vector for its Expression A vector for the expression of the polynucleotide of SEQ ID NO:2 was generated by constructing two precursor plasmids, pTAP488 and pTAP498, in the pZMP31 backbone. Plasmid pZMP31 was constructed from pZMP21 (deposited at the American Type Culture Collection, Manassas, Va., and designated No. PTA-5266) by the removal of the region from the truncated human CD8 alpha cDNA through the SV40 promoter/enhancer, leaving a single dicistronic cassette containing the polylinker followed by polio IRES, DHFR cDNA and SV40 poly A region. Following recombination in yeast, the resulting vector was designated DIRS1 C(FusL) pZMP31 (See, e.g., WO 2005/087810). The cDNA sequences in these plasmids pTAP488 and pTAP498 are illustrated in SEQ ID NO:5 and NO:7, respectively. Briefly, the gene encoding the mature activator was assembled using overlapping oligonucleotides. The resultant construct was named pTAP488 (SEQ ID NO:5 and NO:6). A 6× His tag was then added to the c-terminus end of the activator in pTAP488 resulting in pTAP498 (SEQ ID NO:7 and NO:8). An approximately 570 bp fragment coding for the activator pre-pro leader was added onto the 5' end of the molecule in pTAP498, thereby replacing the existing otpa leader. The approximately 570 bp fragment also contained a 3' polynucleotide sequence encoding a thrombin cleavage site. The resulting plasmid was designated MPET1697 (SEQ ID NO:1 and NO:2). A second plasmid expressing the pre-pro activator an endogenous cleavage site was similarly prepared from pTAP498 by exchanging the otpa sequence with the pre-pro-leader having the endogenous cleavage site at its 3' end. That resulting plasmid was designated MPET1696 (SEQ ID NO:3 and NO:4).

Construction of pTAP488—Gene Synthesis:

The approximately 1300 bp polynucleotide encoding the mature activator was assembled entirely by annealing overlapping oligonucleotide primers and PCR. The mature activator was first constructed in three smaller fragments and the three smaller fragments were then annealed to produce the entire mature activator. Fragment 1 is the N-terminal third of the gene and fragment 3 is the C-terminal third of the gene. The reference DNA sequence used to design the overlapping primers, and construct the mature activator coding sequence came from the published DNA sequence by Nishida (Nishida et al., 34(5) Biochem. 1771-78 (1995) SEQ ID NO:99 and NO:100) except that for the polynucleotide sequence in pTAP488 the Arg, Gly, and Iso codons were optimized for *E. coli* so that the synthesized DNA could be used in both mammalian and microbial expression systems. The oligonucleotides used to synthesize the gene coding for the activator are listed in Table 1. Oligonucleotide primers used to amplify the gene and add ends homologous to the vector backbone are listed in Table 2.

TABLE 1

| | | Synthesis Oligosnucleotides | | |
|---|---|---|---|---|
| 5'/3' | Frag. | Oligo no. | SEQ ID NO. | Sequence |
| 5' | 1 | ZC56869 | 60 | ACTTTGGGGTTAATTGTTCCTCCTCATGAACGAAAATTTGAGAAAA AATTCATTGAGCTTGTCGTAGTTG |
| | 1 | ZC56870 | 61 | CAATGATTCAACTGCTATCCGCACATGGATCTATGAAATGCTCAAC ACTGTAAATGAGATCTACTTACCTTTCAATATTCGTG |
| | 1 | ZC56871 | 62 | GATTAACGTGACATCCACAGCAGATGATACTTTGCACTCATTTGGC GAATGGCGCGCATCAGATTTGCTGAATCG |
| | 1 | ZC56872 | 63 | AACGTGACACTGGATCATTCCACTCTTGGTATCACGTTCGTATATG GCATGTGCAAATCAGATCGTTCTGTAG |
| | 2 | ZC56873 | 64 | CATATATCATTGCCCATGAGATGGGTCATAGTCTGGGCATGTTACA TGACACAAAATTCTGTACTTGTGGGGCTAAAC |
| | 2 | ZC56874 | 65 | CAGCAGTTGTAGTTATGACCAGTATAACAAGTATCTTCTTAAATAT AACCCAAAATGCATTCTTGATCCACCTTTGCGTAAAGATATTGC |
| | 2 | ZC56875 | 66 | GGAGGAAGGTGAAGAATGTGATTGTGGTTCTCCTGCAGATTGTCG CAATCCATGCTGTGATGCTGCAACATGTAAACTG |
| | 2 | ZC56876 | 67 | GTGCAAGATTCGTAAAGCAGGCACAGAATGCCGGCCAGCACGCG ATGACTGTGATGTCGCTGAACACTGCACTGG |
| | 3 | ZC56883 | 68 | GTCAACCATGCCTTAACAACTCTGGTTATTGCTACAATGGGGATTG CCCCATCATGTTAAACCAATGTATTGCTCTCTTTAG |
| | 3 | ZC56884 | 69 | CAGCGTAACTTGCAAGGCAGTTACTATGGCTACTGCACAAAGGAA ATTGGTTACTATGGTAAACGCTTTCCATGTGCACCACAAG |
| | 3 | ZC56885 | 70 | GCAAGAACGACTATTCATACGCGGATGAAAATAAGGGTATCGTTG AACCTGGTACAAAATGTGAAGATGGTAAGGTCTGCATCAACCG |
| 3' | 1 | ZC56896 | 81 | GGATAGCAGTTGAATCATTGTTGTATTTTGTGACCATACTGTGGTC CACAACTACGACAAGCTCAATG |
| | 1 | ZC56895 | 80 | CTGTGGATGTCACGTTAATCAAGTCACCATTGCACCAAAATTCTAG GCCAACCAGTGCTACACGAATATTGAAAGGTAAG |
| | 1 | ZC56894 | 79 | GAATGATCCAGTGTCACGTTCGTGAGTAACTGAGCATGATCATGG CGTTTACGATTCAGCAAATCTGATGCGCGCCAT |
| | 1 | ZC56893 | 78 | CTCATGGGCAATGATATATGCCATATTAAAAGTTATGTTGCTGTAA TCCAGAATAAGTTCTACAGAACGATCTGATTTGC |
| | 2 | ZC56892 | 77 | GGTCATAACTACAACTGCTGAATTCTTTGGGCGGTGGAATGCTTTC TTTGCCAAACATAATGCATGGTTTAGCCCCACAAGTACAG |
| | 2 | ZC56891 | 76 | CAATCACATTCTTCACCTTCCTCCCAAATTTCATTGCCACAAACTG CAGGTGAAGCAATATCTTTACGCAAAGG |
| | 2 | ZC56890 | 75 | CTGCTTTACGAATCTTGCACTTGTCACAACACTCACCATTGCCACA TTCTGCCCCTGGTTTCAGTTTACATGTTGCAGCATC |
| | 2 | ZC56889 | 74 | GTTGTTAAGGCATGGTTGACCATTGCGTTGGAACTCATTACGGGGA CACTCAGCAGATTGGCCAGTGCAGTGTTCAGCGA |
| | 3 | ZC56888 | 73 | CTGCCTTGCAAGTTACGCTGAAAACATGAATCTTGAGCCACAGTT GCACTTGGACTAAAGAGAGCAATACATTGG |
| | 3 | ZC56887 | 72 | CGTATGAATAGTCGTTCTTGCAACGCATATTTTTTTGAATGAATT ATCTAAGCAGTATAAACGGCCACATTTTACATCTTGTGGTGCACAT GGAAAG |
| | 3 | ZC56886 | 71 | TTAGTAGGCTGTATTCACATCAACACACTTGCGGTTGATGCAGACC TTACC |

TABLE 2

Amplification Oligonucleotides

| 5'/3' | Oligo no. | SEQ ID NO. | Sequence |
|---|---|---|---|
| 5' | ZC56902 | 57 | TCTATGTTCGTTTTTTCTATTGCTACAAACGCGT ATGCAGTTCCTCCTCATGAACGAAAA |
|  | ZC57098 | 58 | CAGGAAATCCATGCCGAGTTGAGACGCTTCCGTAGA TCTACTTTGGGGTTAATTGTTCCTC |
|  | ZC58328 | 98 | TCCACAGGTGTCCAGGGAATTCATATAGGCCGGCCA CCATGATCCAGATTCTCTTGGTA |
| 3' | ZC57099 | 59 | ACAACCCCAGAGCTGTTTTAAGGCGCGCCTCTA GATTAGTAGGCTGTATTCACATCAAC |
|  | ZC57640 | 82 | AGGCGCGCCTCTAGATTAGTGATGGTGATGGTGATG GTAGGCTGTATTCACATCAAC |
|  | ZC57641 | 83 | TGGGTACAACCCCAGAGCTGTTTTAAGGCGCGCCTC TAGATTAGTGATGGTGATGGTGATG |
|  | ZC58327 | 97 | TTTTTTCTCAAATTTTCGTTCATGAGGAGGAACTCTT GGCCCCAAAGTCTTTTTGATGGG |
|  | ZC58325 | 101 | CAATGAATTTTTTCTCAAATTTTCGTTCATGAGGAGG AACAATTAACCCCAAAGTCTTTTG |

Each fragment was assembled by PCR using 50 picomoles of the fragment's 5' and 3' outer-most primers, 5 picomoles of the fragment's internal primers, and Platinum Pfx polymerase (Invitrogen, Carlsbad, Calif., Cat. #11708-013). PCR was performed under the following conditions: ten cycles of 94° C. for 30 sec, 55° C. for 30 sec, and 68° C. for 30 sec.

Products from the fragment assembly reactions described above were used as template in a PCR using 20 picomoles of the 5' and 3' outer-most oligonucleotides from the corresponding reactions. An exception was fragment 1. Because these fragments were used to generate multiple constructs, fragment 1 was amplified using oligonucleotide ZC56902 instead of ZC56869 in order to extend the sequence on the 5' end for constructs (e.g., E. coli expression vectors). In either instance, the reaction consisted of thirty cycles of 94° C. for 30 sec, 55° C. for 30 sec, and 68° C. for 30 sec using Platinum Pfx. The PCR fragments were checked for size by electrophoresis on a 1×TBE agarose gel.

For assembly of the entire gene coding for the mature activator, the three fragments were gel purified using a QIAquick Gel Extraction Kit (Qiagen, Valencia, Calif., Cat. #28704). They were used as template in an annealing reaction which consisted of five cycles of 94° C. for 30 sec, 55° C. for 30 sec, and 68° C. for 30 sec using Platinum Pfx. Then 20 picomoles of primers ZC56869 and ZC56886 were added to the reaction, and the PCR continued for twenty-five more cycles but with an extension time of 1.5 minutes at 68° C. The PCR fragment was analyzed on a 1×TBE agarose gel. In order to add DNA with homology to pZMP31 onto the 5' and 3' ends of the gene, another PCR was done under the same conditions using primers ZC57098 and ZC57099 and 1 µl of the fragment generated with primers ZC56869 and ZC56886.

Intermediate vector construction. The full length fragment encoding the mature activator was precipitated with 2× volume 100% ethanol and centrifuged. The pellet was resuspended in 10 µl sterile water. The vector backbone pZMP31 was linearized with BglII (Promega, Madison Wis., Cat. #R6085) using the manufacturer's guidelines. The DNA was gel purified using a QIAquick Gel Extraction Kit and quantitated at an $A_{260}$ measurement.

One µl of linearized backbone and 5 µl to 10 µl of the synthesized gene coding for the activator were recombined via yeast homologous recombination in SF838-9Dα electrocompetent Saccharomyces cerevisiae. The mixture was electroporated with a BioRad Gene Pulser II using the settings 25 µF, infinity ohms, 0.75 kV (5 kV/cm), and rescued in 1.2 M sorbitol. The cells were immediately plated on -URA D agar plates of 5.6% -Ura, -Trp, -Thr dropout powder (0.56 g/L), 2% glucose, 0.67% yeast nitrogen base (6.7 g/L), and 1.8% bacto agar, and incubated at 30° C. for 2 days.

Screening.

The DNA from the yeast cells was isolated by first resuspending the cells on the -URA D plate with water. The cells were transferred to a microfuge tube and briefly centrifuged to collect the cells. The cells were resuspended in yeast lysis buffer containing ZYMOLYASE™ lytic enzyme (Zymo Research Co., Orange, Calif., #E1002). The resuspended cells were incubated for 15 min at 37° C. Half of the mixture was then transferred to a microfuge tube with glass beads and an equal volume of phenol/chloroform/isoamyl alcohol. The tube was vortexed repeatedly and then centrifuged. The aqueous phase was removed, and the DNA was precipitated with 2× volume of 100% ethanol and again centrifuged. The supernatant was removed, and the pellet was resuspended in 100 µl sterile water. One µl was used to transform 50 µl TOP10 electrocompetent E. coli cells (Invitrogen, Cat. #C4040-50). The electroporation settings were 25 µF, 400 ohms, 2.0 kV, and the cells were rescued in an SOC rich broth of 2% bacto tryptone, 0.5% yeast extract, 10 mM NaCl, 2.5 mM KCl, 10 mM $MgCl_2$, 10 mM $MgSO_4$ and 20 mM glucose. The cells were spread on LB+ampicillin agar and incubated overnight at 37° C.

The next day, 20 colonies were screened for the gene coding for the activator by colony PCR. Each colony was put into approximately 100 µl LB broth, and 10 µl of the cell-broth mixture was used as template. Primers ZC57098 and ZC57099 were used with Advantage II polymerase, and the reactions were run for thirty-five cycles of 94° C. for 30 sec, 55° C. for 30 sec, and 72° C. for 1.5 min. PCR fragments were electrophoresed on a 1×TBE agarose gel. For those fragments matching the expected fragment size, the corresponding 100

μl LB and colony culture was streaked onto LB+ampicillin agar plates, and the cultures were incubated overnight at 37° C. Ten colonies were submitted to DNA sequencing for sequence analysis and all were determined to contain a correctly oriented polynucleotide encoding a mature activator.

Final Vector Construction.

Vectors from two of the samples, referenced as pTAP488 sample D and pTAP488 sample J, which were determined to have correct sequences, were each digested using EcoRI according to the manufacturer's directions (Promega, Cat. #R601J). The DNA was electrophoresed on a 1×TBE agarose gel. Bands from these samples were gel purified (QIAquick gel extraction kit) and treated with heat labile alkaline phosphatase (Epicentre, Madison Wis., Cat. #AP49010). The alkaline phosphatase was inactivated and the concentration of the two fragments was determined by measuring the $A_{260}$ on a NanoDrop. These two fragments were then ligated together using T4 DNA ligase (Promega, Cat. #M180A) and 0.1 picomoles of the sample J fragment and 0.15 picomoles of the sample D fragment. The ligation mixture was incubated at room temperature for approximately 30 min and then transformed into TOP10 E. coli electrocompetent cells as previously described.

Twenty transformants were inoculated into Superbroth APS (0.91% w/w, 0.5% glycerol v/w (Difco C/N 212486)) with ampicillin and incubated overnight at 37° C. with agitation. Plasmid DNA from the cultures was isolated using a QIAprep Spin Miniprep Kit (Qiagen, Cat. #27104 and #27106). Plasmid DNA was digested with NaeI (NEB, Ipswich, Mass., Cat. #R019L) and electrophoresed on a 1×TBE agarose gel. Four DNA samples with insert in the correct orientation were submitted for sequence analysis.

The vector pTAP498 was constructed by PCR using pTAP488 as template. The 3' end of the mature activator gene in pTAP488 was extended and a C-terminal 6×His tag was added thereto, using primers ZC57098 and ZC57640. The PCR reaction consisted of five cycles of 94° C. for 30 sec, 52° C. for 30 sec, and 68° C. for 1.5 min using Accuprime Pfx polymerase. A second PCR reaction using 1 μl of the first reaction and primers ZC57098 and ZC57641 extended the 6×His tag and added a 3' sequence homologous to pZMP31 for yeast recombination cloning. The reaction cycled for twenty-five cycles of 94° C. for 30 sec, 52° C. for 30 sec, and 68° C. for 1.5 min using Accuprime Pfx polymerase. The amplified fragment was precipitated with 2× volume 100% ethanol, the supernatant was discarded, and the pellet was resuspended in 10 μl of sterile water.

Assembly.

Three μl of the His-tagged mature activator gene were recombined with 1 .micro.l of BglII cut pZMP31 in SF838-9Dα. The mixture of recombinant vector and cells was electroporated under the following conditions: 25 μF, infinity ohms, 0.75 kV and rescued in 1.2M sorbitol. The cells were immediately plated onto -URA D agar plates.

Screening.

The DNA from the yeast cells was isolated and transferred to E. coli as described above. The E. coli transformants were screened by PCR for the gene coding for activator using ZC57642, ZC57641 primers, and Accuprime Pfx polymerase. Conditions consisted of 35 cycles of 94° C. for 30 sec, 52° C. for 30 sec, and 68° C. for 60 sec. Colonies containing the gene were streaked onto LB+ampicillin agar plates, incubated overnight at 37° C., and submitted to sequencing.

Construction of MPET1697:

MPET1697 is a 9237 bp mammalian expression vector containing a polynucleotide encoding a pre-pro activator polypeptide. The encoded activator is, from N-terminus to C-terminus, a pre-pro leader, a thrombin cleavage site and a mature activator sequence. The thrombin site is situated after the C-terminus of the pre-pro leader and before the mature N-terminus of the activator. Thus, MPET 1697 expresses an activator precursor that is cleavable at the thrombin cleavage site to release the active (mature) form of the activator.

The pre-pro leader was assembled as one fragment by annealing overlapping oligonucleotides followed by a subsequent PCR amplification step. The oligonucleotides for the pre-pro region of the gene coding for activator are listed in Table 3. Primer member ZC58327 is used to engineer the thrombin cleavage site into the prepro activator fragment at its 3' end.

TABLE 3

| | | | |
|---|---|---|---|
| Pre-Pro Oligonucleotides | | | |
| 5'/3' | Oligo number | SEQ ID NO. | Sequence |
| 5' | ZC58220 | 84 | GCTTAGCAGTTTTTCCATATCAAGGTTGCTCTATAATCCTGGGATCTGGGAATGTTAATG |
| | ZC58221 | 85 | GTATCCACAAAAAGTCACTGCATTGCCCAAAGGAGCAGTTCAGCAGCCTGAG |
| | ZC58222 | 86 | GAAGGGAGAGCCAGTGGTCCTTCACCTAGAAAAAAATAAAGAACTTTTTTCAGAAGATTACAGTGAGACTCATTATTCG |
| | ZC58223 | 87 | GAGAAATTACAACAAACCCTTCAGTTGAGGATCACTGCTATTATCATGGACGGATCCAGAATGATGCTGAGTC |
| | ZC58224 | 88 | GAAAGGACATTTCAAGCTTCGAGGGGAGACGTACTTTATTGAACCCTTGAAGATTCCCGACAGTGAAG |
| | ZC58225 | 89 | GATGAAGCCCCCAAAATGTGTGGGGTAACCCAGGATAATTGGGAATCAGATGAACCCATCAAAAAGACTTTGG |
| 3' | ZC58226 | 90 | GATATGGAAAAACTGCTAAGCATATAATTACCAAGAGAATCTGGATCATTTTGGAGGCTGAATTTGGCTTGAAGAC |
| | ZC58227 | 91 | GCAGTGACTTTTTGTGGATACACTACTTCATAATCATTAACATTCCCAGATCCCAG |

TABLE 3 -continued

Pre-Pro Oligonucleotides

| 5'/3' | Oligo number | SEQ ID NO. | Sequence |
|---|---|---|---|
| | ZC58228 | 92 | GGACCACTGGCTCTCCCTTCACTTCAAATTCATATTGCAT GGCATCTTCATACTTTTGCTCAGGCTGCTGAACTGCTC |
| 3' | ZC58229 | 93 | *CTGAAGGGTTTGTTGTAATTTCTCTGTCATCAGACGAATAATG AGTCTCACTGTAATC* |
| | ZC58242 | 94 | GAAGCTTGAAATGTCCTTTCAAACCATTGCATGCACTGA TGCTTGCAGTTGACTCAGCATCATTCTGGATCC |
| | ZC58243 | 95 | CACATTTTGGGGGCTTCATCCTCATTTTCTATGTTTTCAT ATTTGTAGACTGCATGGGCTTCACTGTCGGGAATCTTC |
| | ZC58244 | 96 | GAATTTTTTCTCAAATTTTCGTTCATGAGGAGGAACAATT AACCCCAAAGTCTTTTTGATGGGTTC |

Approximately 50 picomoles of the zc58220 and zc58226 primers and approximately 5 picomoles of each of the remaining primers in Table 3 were used in an annealing reaction with Expand polymerase (Roche Molecular Diag., Indianapolis, Ind., Cat. #1759028). The cycling conditions consisted of ten cycles of 94° C. for 60 sec, 58° C. for 2 min, and 68° C. for 3 min followed by one cycle of 68° C. for 6 min and a 4° C. hold. One µl of the product from the annealing reaction was used as template in a second PCR using 20 picomoles of primers zc58220 and zc58226. PCR conditions were thirty cycles of 94° C. for 60 sec, 58° C. for 2 min, and 68° C. for 3 min followed by one cycle of 68° C. for 6 min and a 4° C. hold. The PCR product was gel purified from a 1×TAE using a QIAQuick Gel Extraction Kit. The gel purified fragment was used in a third PCR with primers zc58328 and zc58327 at thirty cycles of 94° C. for 60 sec, 58° C. for 2 min, and 68° C. for 3 min followed by one cycle of 68° C. for 6 min and a 4° C. hold. This third PCR product was then gel purified.

Assembly.

The plasmid pTAP498 was cut with NarI (NEB, Cat. #R0191S) according to the manufacturer's directions and gel purified. One hundred µl of electrocompetent SF838-9Dα cells were mixed with 10 µl of the gel purified DNA from the third PCR reaction and 100 ng of Nan cut pTAP498 vector. The DNA-cell mixture was electroporated and plated as described above. The recombinant plasmid contains an orotidine-5'-phosphate decarboxylase (URA3) sequence, allowing for transformant selection. After about 72 hr, the Ura+ yeast transformants from a single plate were resuspended in 1 ml H$_2$O and spun briefly to pellet the yeast cells. The cell pellet was resuspended by vortexing in 0.1 ml of yeast lysis buffer and 0.1 ml of buffer P1 from a QIAprep Spin Miniprep Kit, in the presence of 10 units of Zymolyase. The yeast suspension was incubated for 10 min in a 37° C. waterbath. The standard QIAprep Spin Miniprep Kit protocol was followed starting at the step of adding buffer P2.

Five µl of plasmid DNA were transferred by electroporation into 50 µl DH12S electrocompetent *E. coli* (Invitrogen, Cat. #18312-017) using the settings 2.0 kV, 25 µF, and 400 ohms. Following electroporation, 1 ml SOC was added to the samples, and the cells were plated in a 50 µl and 200 µl aliquot onto two LB+ampicillin agar plates and incubated overnight at 37° C.

Random *E. coli* transformants were picked and individually scraped onto an LB+ampicillin agar plate using a pipette tip. Residual bacteria from the tip were scraped into a PCR tube. Twenty picomoles of oligonucleotide primers ZC58328 and ZC58327 were mixed with 50 µl of Platinum PCR Supermix, High Fidelity (Invitrogen, #12532-016). Fifty µl of the Supermix-oligonucleotide mixture was used to amplify the region coding for the prepro leader from the selected colonies. Reaction conditions were thirty cycles of 94° C. for 60 sec, 58° C. for 2 min, and 68° C. for 3 min followed by one cycle of 68° C. for 6 min and a 4° C. hold. PCR fragments were analyzed by 1×TAE agarose gel electrophoresis. Clones containing the prepro leader were submitted for DNA sequence analysis.

Construction of MPET1696:

MPET1696 was derived from pTAP498 similarly to what is described above for MPET1697. The primary difference between MPET1696 and MPET1697, though, is that MPET1696 is not engineered to include the thrombin cleavage site between the prepro sequence and the mature activator sequence. (SEQ ID NO:3 and NO:4). During gene assembly of the three short fragments primer zc58327 was substituted with primer zc58325, resulting in no thrombin cleavage site between the prepro secretion leader sequence and the mature activator sequence.

Example 2

Transfection and Preparation of Mammalian Cell Lines

Stable Transfections, Generation of Amplified Pools and Clone Selection.

Vectors MPET 1696, MPET 1697, pTAP 488 and pTAP 498 were each stably transfected into DXB11 (ATCC, Manassas, Va., Cat #CRL-11397) and DG44 (Chasin et al., 12 Som. Cell. Molec. Genet. 555 (1986)), CHO cell lines. For the MPET 1696 and MPET 1697 transfections a low DNA copy, high capacitance electroporation protocol was followed. Two electroporations were performed per construct. In the case of first electroporation, 25 µg of enzyme-digested DNA were combined with 20 million cells resuspended in non-selective PFCHO medium (SAFC BioScience, St. Louis, Mo., Cat. #14340C) (containing hypoxanthine and thymidine in the absence of methotrexate "MTX") supplemented with 1.25% DMSO. Cells were subjected to an electrical pulse at the electroporator setting of 200V and 3275 µF capacitance. Following electroporation, cells were transferred into non-selective PFCHO medium supplemented with 1.25% DMSO in a T-75 flask (Invitrogen, Cat. #11067-030). After a three-day incubation period in a 37° C., 5% CO$_2$ incubator (no agitation), cells were subjected to selective pressure to generate a stable 0 nM MTX pool (discussed below). A second electroporation was performed as described; with the exception that no DMSO was used at any point during the transfection. The cells transfected without DMSO were subjected to stringent selection to generate a 200 nM stable pool (discussed below).

For the pTAP488 and pTAP498 transfections a high DNA copy, low capacitance protocol was followed. Separately, pTAP488 and pTAP498 vector DNA was enzyme digested, precipitated and resuspended in non-selective PFCHO. A ratio of 200 μg of enzyme-digested vector DNA was combined with 10 million cells and exposed to an electrical pulse at the electroporator setting of 300V and 950 μF capacitance. Following electroporation, cells were transferred into a 125 ml shake flask containing non-selective PFCHO medium (supplemented with hypoxanthine and thymidine in the absence of methotrexate). The shake flask was left in a 37° C., 5% $CO_2$, 120 rpm incubator for 48 hr, after which time the cells were subjected to selective pressure to generate stable pools.

Methotrexate ("MTX") amplified pools were then generated from the CHO transfectants. The pools included a 0 nM MTX pool (not an amplified pool), a 200 nM MTX pool, a 500 nM MTX pool, a 500-0 nM MTX pool and a 1000 nM MTX pool, as described below.

DXB11/MPET1696, DXB11/MPET1697, DG44/MPET1696 and DG44/MPET1697 0 nM Non-Amplified Pools: Cells that had been electroporated in the presence of DMSO (as described above) were exposed to PFCHO selective medium (PFCHO without hypoxanthine and thymidine) to generate 0 nM MTX stable pools. After eight passages in selective medium (about 2.5-3 weeks), both the DXB11/MPET1696 and the DXB11/MPET1697 transfectants were fully recovered (viability>90%). DG44 host cells had similar viability but had a slightly longer recovery time than did the DXB11 transfectants.

DXB11/MPET1696, DXB11/MPET1697, DG44/MPET1696 and DG44/MPET1697 200 nM Pools: Cells that had been electroporated in the absence of DMSO (as described above) were exposed to PFCHO selective medium (PFCHO without hypoxanthine and thymidine) supplemented with 200 nM MTX to generate stable 200 nM pools. DG44/MPET1697 and DG44/MPET1696 transfectants fully recovered (viability>90%) after ten and twelve passages (about 5.5-7.5 weeks), respectively. Specific production for DG44 cells was comparatively lower than for the DXB11 cells (between about 5-10 fold lower for DG44 cells), thus the DG44 cells were not taken forward. DXB11/MPET1697 and DXB11/MPET1696 transfectants recovered after 19 and 22 passages (about 7-9 weeks), respectively. Recovery was substantially improved for the cells expressing the 1697 construct compared to the 1696 construct. As is seen in Table 4, the cells expressing 1697 had a faster doubling time, which is a surprising benefit of the 1697 construct transformed cells. Additionally, Table 4 indicates that the 1697 host cell had a higher viable cell density and a higher specific productivity than did the 1696 host cell. Because cells transfected with the MPET1697 construct have improved recovery, growth, viability and protein production compared to those transfected with the MPET1696 construct, the DXB11/MPET1697 transfected cells were used in further amplification and cloning steps (e.g., generation of 1000 nM, 500 nM & 500-0 nM pools and dilution cloning to isolate high expressing clones from the DXB11/MPET1697 500 nM, 500-0 nM and 1000 nM pools).

TABLE 4

Production Assay Results

| Sample | Doubling Time in PFCHO (hr)* | Final Viable Cell Density in ZF1 ($e^5$ c/ml) | Conc. (ng/ml) | Weeks until Full Recovery | Specific Productivity (pg/c/d) |
|---|---|---|---|---|---|
| DXB11/MPET1696 0 nM | 23.3 | 40.53 | 1600 | 2.5 | 0.11 |
| DXB11 MPET1697 0 nM | 22.3 | 27.76 | 1700 | 2.5 | 0.16 |
| DXB11 MPET1696 200 nM | 42.9 | 26.95 | 2235 | 22 | 0.2 |
| DXB11 MPET1697 200 nM | 32.7 | 28.78 | 2777 | 19 | 0.24 |

*Column 2 is doubling time in regular passaging.

DXB11/MPET1697 500 nM, 500-0 nM & 1000 nM Pools: A fully recovered DXB11/MPET1697 200 nM stable pool was exposed to PFCHO selective medium supplemented with 500 nM MTX. The 500-0 nM pool was made from splitting a portion of DXB11/MPET1697 500 nM pool cells into selective PFCHO medium containing no methotrexate, (0 nM pool). The 1000 nM pool was made from a portion of the 500 nM pool cells split into selective PFCHO medium containing 1000 nM methotrexate. During amplification cell viability never dropped below about 90%. Cells had immediate recovery.

Dilution cloning to isolate high expressing clones from the DXB11/MPET1697 500 nM, 500-0 nM and 1000 nM pools were cloned via limited dilution plating. For each pool, a first plate was generated containing a theoretical calculation of 0.5 cells per well in selective PFCHO medium supplemented with 3% fetal bovine serum (HyClone, Logan, Utah, Cat. #SH30406) and with the corresponding amount of MTX. A second plate was generated theoretically containing 0.75 cells per well in selective PFCHO medium corresponding amount of MTX and 3% FBS. Ninety wells from the ten 96-well plates were confluent after 3 to 4 weeks. The cells from these 90 wells were assayed for production during an initial screen and twenty-three clones were transferred to shake flasks for production assay screening from which four clones were selected based on production assay and growth data. These four clones were bulked up in selective PFCHO medium with 500 nM MTX, and then pelleted and resuspended in selective 0 nM MPFCHO medium supplemented with 10% DMSO. Aliquots containing 20 million cells were generated and stored for subsequent use.

Example 3

Purification of Activator

Cell culture supernatant from Example 3 containing the recombinant pre-pro-activator was then concentrated and purified. Concentration of the cell culture supernatant was performed by ultrafiltration (UF) using a 30 kD polyethersulfone ("PES") membrane (Millipore, Billerica, Mass., Cat. #P2B030A01), for example. Other concentration systems are known to those ordinarily skilled in the art, and are applicable here. Other membrane types and molecular weight cut-offs can also be used with ultrafiltration to concentrate the expressed pre-pro-activator. Final volume following ultrafiltration was small enough to make loading onto the IMAC column convenient. UF was followed by diafiltration (DF) into a suitable buffer, e.g., one suitable buffer comprised 25 mM HEPES and 150-250 mM NaCl at pH 7.0 to pH 7.5.

As mentioned, the recombinant activator was expressed and purified as a pre-pro-activator. The pre-pro-activator was then itself activated. One suitable activation technique uses heat activation. Briefly, the UF/DF retentate was incubated overnight at 37° C. In an alternative approach, the pre-pro-activator was activated before the UF/DF and/or was activated by one or more of enzymes, salt combinations, various metals, pH shifts and buffers. Enzyme activations included using a protease such as thrombin. In this alternative embodiment, between 10 μg/mL and 100 μg/mL, preferably 50 μg/mL, of thrombin was combined with pre-pro-activator and the combination was incubated between 1 hr and 24 hr at between 21° C. and 37° C., preferably 21° C. A trypsin activation was similarly used wherein 20 μg of trypsin was combined with pre-pro-activator and the combination was incubated about 30 min at 37° C. Other proteases may be useful as may metal ions such as copper or nickel at 37° C. for 16-24 hr. Optionally, a viral inactivation step can be performed; for example, using Triton X-100.

The mature activator was then purified from the retentate using IMAC capture chromatography. The column was packed with a Toyopearl AF chelate 650M resin (Toyo Haas, Philadelphia, Pa., Cat. #14475) prepared as follows: a five column volume rinse using dH$_2$O, followed by a five column volume charge with 1 M ZnCl$_2$, followed by a five column volume rinse with dH$_2$O, followed by a 5-10 column volume equilibration with 25 mM phosphate 1 M NaCl, 10 mM Imidazole at pH 7.2. Other metals can be used to charge the column, including, but not limited to copper and nickel. The column was then loaded with conditioned UF/DF retentate, washed with 5-10 column volume of 25 mM phosphate 1 M NaCl, 10 mM Imidazole pH 7.2 and eluted with a ten column volume gradient from 100% EQ/wash buffer of 25 mM phosphate 1 M NaCl, 10 mM Imidazole pH 7.2 to 50% Elution buffer of 25 mM phosphate 1 M NaCl, 500 mM Imidazole at pH 7.2. In alternative column purification, a similar IMAC procedure can be performed directly on the cell culture, thus bypassing the UF/DF process and the activator subsequently activated. Similarly, anion exchange columns, cation exchange columns and IMAC and, for example, a borate buffer and/or pH variations, were used to purify the mature activator. Other methods for purifying activator or pre-pro activator are similarly applicable and known to the ordinarily skilled artisan.

A polishing chromatography step was then performed. Any suitable chromatography can be used, including, but not limited to, ion exchange chromatography, hydrophobic interaction chromatography, size exclusion chromatography and heparin chromatography. Heparin columns are prepared by equilibrating the column with 5 column volume of 25 mM phosphate 70 mM NaCl$_2$ at pH 7.4. An IMAC capture pool was adjusted by diluting the pool with 25 mM Na$_2$PO$_4$ until the conductivity of the combined pool is from about 10 to about 12 mS/cm and was then loaded onto the column and washed with five column volume of equilibration buffer and eluted with a fifteen column volume gradient from 0% to 40% elution buffer (elution buffer is 25 mM phosphate and 1 M NaCl at pH 7.4). The purified activator is then stored in 25 mM sodium phosphate, 250 mM NaCl, pH 7.4. Pools may be stored at −80° C. for stability.

Example 4

Analysis and Characterization of Activator

Purified mature activator was assayed for its ability to cleave a precursor thrombin molecule to its activated form, i.e., thrombin. In this assay the precursor thrombin molecule was from a recombinant source; however, the activator will also activate plasma derived prothrombin. Samples containing activator were serially diluted in a 125 mM 2-(morpholino)ethanesulfonic acid (MES) buffer at pH 6 with BSA carrier. Prethrombin-1 (see U.S. Pat. No. 5,527,692), was then added to the activator sample and incubated for 3 min at ambient temperature. The reaction was quenched with 100 mM EDTA at pH 8.4. Sample solution pH was adjusted to 8.0 with a 100 mM Tris/100 mM Imidazole buffer and the amount of thrombin generated was then quantified by measuring the rate of hydrolysis of Pefachrome TH (Pentapharm, Basal, CH) by monitoring the increase in the optical absorbance (405 nm). Upon hydrolysis, the para-nitroaniline absorbs light at 405 nm, and its rate of generation is proportional to the thrombin activity in the sample. The mature activator's activity was quantitated against a two-fold venom derived ecarin (Pentapharm) standard curve from 2000 to 62.5 ng/mL. The recombinant mature activator cleaves thrombin precursor molecules to generate active thrombin.

Western blot analysis was performed to detect the recombinant activator in sample. Samples containing pre-pro-activator or mature activator were prepared in SDS buffer with reducing agents added (Invitrogen, Cat. #NP0004). Proteins were separated using an applied voltage of 200V for 40-60 minutes on 4-12% Bis-Tris precast gels using MOPS running buffer (Invitrogen, Cat. #NP0321box; #NP0001), and then electroblotted onto a nitrocellulose membrane. The membrane was blocked with non-fat dry milk and then probed with an anti-HIS tagged antibody (R&D Systems, Cat. #MAB050H) followed by detection using a Lumi-Light solution (Roche, Cat. #2015200). Analysis of the western blot indicated separation of more than one species containing the His tag. Subsequent sequencing of these separated bands from coomassie brilliant blue stained PVDF blots of SDS-PAGE gels, run as described below, confirmed separation of the pro species from the mature activator.

Samples containing activator were assayed by SDS-PAGE by preparing the samples in SDS sample buffer with reducing agents added (Invitrogen, Cat. #NP0004). Proteins were then separated on 4-12% Bis-Tris precast gels using MOPS running buffer at 200V constant voltage for 45-60 min. Proteins from cell culture, ultrafiltered, diafiltered and various chromatographic fractions were each imaged using coomassie brilliant blue or silver staining.

Analytical RP-HPLC was performed with a series of in-process samples each containing approximately 30 μg of activator ranging in volume from 100 μl to 800 μl. In this example, there was no further dilution or sample handling prior to analysis for downstream purification samples. Samples were loaded onto a PLRP-S column from polymer laboratories, and eluted with a mobile phase of acetonitrile and water, using a gradient of 30% to 50% mobile phase B in 8 min. Prior to analysis, the column was equilibrated with mobile phase A for approximately half an hour. Proteins were detected by 280 nm and 215 nm UV absorbance. A zinc-IMAC chromatographic eluate was fractionated by reverse-phase-HPLC and characterized by N-terminal sequencing and western blot assays. The major peak of RP-HPLC was identified as Ecarin related material. The pre-peaks and post peaks were characterized as unrelated species. N terminal sequencing revealed mature activator species with different N-terminus start sites. The most common N-terminus start sites for the mature activator include V191, T186, L187 and V154. The V191 mature activator was more frequently, though not exclusively, present when the pre-pro activator was activated using thrombin. Similarly, the T186 mature activator was more frequently, though not exclusively, present when the pre-pro-activator was activated with trypsin or heat. These were general trends and are not meant to limit the instant invention by linking the mature activator polypeptide sequence to any particular method of activation.

Capillary HPLC coupled to time-of-flight mass spectrometry was performed to assess sequence integrity and post-translational modifications of the activator in sample. An activator sample formulated in a phosphate/sodium buffer was divided into three aliquots that were treated differently and then characterized by intact mass analysis. The first aliquot was left untreated; the second aliquot was deglycosylated; and the third aliquot was deglycosylated and reduced. No intact mass data was received from the first aliquot mainly because of the impact of glycosylation on analysis. The second aliquot provided a main mass consistent with mature ecarin with an N-terminal 5 amino acid extension starting at T186. The odd cysteine was identified as C255. Mass matching indicated that C255 was cysteinylated, glutathionylated, or converted to dehydroalanine (ratio of about 3:2:1), but not free. The other thirty-four cysteines appear disulfide-bonded. The third aliquot provided a main mass that was consistent with mature ecarin having an N-terminal five amino acid extension starting at T186. Additionally, five minor species with different N-termini were detected (≤10%). No C-terminal clipping of the His-tag was observed. The analyzed sample was mainly composed of glycosylated, disulfide bonded activator having a mass similar to mature ecarin and including N-terminal amino acids corresponding to the engineered thrombin cleavage site.

To further assess the sequence integrity and post translational modification for the activator, an IMAC pool sample digested with trypsin was assayed using capillary RP-HPLC coupled with intact mass analysis by time-of-flight. The tryptic digest was prepared by incubating the sample in the presence of trypsin at a protein to protease ratio of 20:1 for 21.5 hours at 37° C. Results from this assay showed N-terminal heterogeneity and C-terminal clipping of the His-tag. Results also showed a polypeptide from the pro-region with the free cysteine 170 of the ecarin pro-protein "cysteine switch" motif (-Pro-Lys-Met-Cys-Gly-Val-), which is commonly used in the activation of matrix metalloproteinase zymogens (Grams et al., 335 FEBS Lett. 76-80 (1993); Nishida et al., 1995). The peptide map also localized two of the disulfide bridges. These results are unlike those received from analysis of a heparin pool fraction diluted in a phosphate/sodium chloride buffer, wherein N-terminal heterogeneity was also observed but not the pro-region with the cysteine switch or loss of the C-terminal His tag. The observed differences are likely due to slight differences in the purification process for the samples of activator.

N-terminal sequencing of purified samples loaded on pre-cycled filters or ProSorb filters (Applied Biosys., Inc. Foster City, Calif.) showed extra amino acid residues at their N-terminuses compared to the published mature ecarin N-terminal sequence. In some instances, these additional residues formed part of the thrombin cleavage site engineered into the pre-pro molecule. N-terminal sequencing data was obtained from series of reverse-phase-HPLC fractions isolated from heparin columns or from IMAC columns. Heterogenous mature activator sequences were obtained for the RP-HPLC fraction sample. Data received for a pool from a heparin column fraction showed a single sequence, however.

Example 5

Immobilization of Activator to a Beaded Resin Support

The mature activator was immobilized on a cyanogens bromide activated sepharose beaded resin support (GE Health Sciences) according to manufacturer's instructions. If required, the activator solution was dialysed to remove buffer components prior to immobilization. Then 1 mg to 20 mg of activator in 5 ml to 50 ml of solution was combined with an equal volume of 100 mM Sodium bicarbonate and 200 mM NaCl at pH 8.3 and added to 1 ml of hydrated and washed resin, then incubated at room temperature for several hours. During the reaction time, samples of the supernatant were taken to monitor the extent of reaction. Once complete, the reaction mixture was filtered off and the resin quenched with 100 mM Tris pH 8.0 and allowed to react for 2 hr at room temperature. Then, the resin was washed with seven alternating cycles of 100 mM sodium acetate, 500 mM NaCl at pH 5.0 and 100 mM Tris, 500 mM NaCl at pH 8.0 solutions to remove excess reagents. The resin with immobilized mature activator was placed in an azide or alcohol solution for long term storage.

Example 6

Activation of Prethrombin-1 to Thrombin Using Mature Activator

Recombinant prethrombin-1 was then used to identify buffer conditions that provide optimum conversion of prethrombin-1 to thrombin and thrombin yield. Optimum conditions for converting prethrombin-1 to thrombin were determined using purified mature activator in solution. Alternatively, the mature activator for converting a thrombin precursor to thrombin can use the immobilized mature activator. Prethrombin-1 was diluted into buffers to create the following 3 by 3 matrix of conditions pH=6.0, 7.0, 8.3 and NaCl=70 mM, 150 mM and 300 mM. 1 mL samples of prethrombin-1 in these buffer conditions were then combined with 35 mL of immobilized activator, and the mixture was allowed to react at room temperature for 2.5 min prior to quenching with glacial acetic acid (Baker, Cat. #9526-03) or 1 M acetic acid solution. Reaction products were analyzed by reverse phase HPLC. The results showed that thrombin yields were best from about pH 7.0 to about pH 8.3 and salt concentration ranging from about 150 mM to about 300 mM.

Applicants have surprisingly found that incubation of mature activator in IMAC pool (derived using Zn-charged IMAC) with either Cu (26 mM copper sulfate) or Ni (26 mM nickelous sulfate) has shown to increase the mature activator activity by 7-fold up to 14-fold. Additional experimentation has confirmed that the increased activity is the result of a mature activator-copper (or nickel) interaction.

A production method was tested with immobilized mature activator. The thrombin product was captured using p-aminobenzamidine affinity chromatography. Briefly, 160 mL of 5 mg/mL prethrombin-1 in 20 mM Tris 70 mM NaCl at pH 7.3 was pumped through a 0.4 mL immobilized mature activator (1 mg/mL) column and the flow-through was run through a 20 cm bed height PABA resin bed. Once the flow-through stage was complete, the PABA column was washed with a 20 mM Tris, 70 mM NaCl buffer at pH 7.3, then with a 20 mM Tris, 264 mM NaCl, 7.1% (v/v) isopropyl alcohol buffer, and finally eluted with 20 mM Tris, 500 mM NaCl, 15.7% (v/v) isopropyl alcohol, where the eluate was collected according to the criteria set during process development. Thrombin that was produced by the immobilized activator was compared to thrombin that was prepared by conversion of pre-thrombin-1 to thrombin using commercially available activators. The thrombin captured by PABA chromatography was analyzed by HPLC, clotting assay and mass spectrometry, and found to be similar to thrombin produced using the commercial activator. Thus, the thrombin produced by activation of prethrombin-1 using mature activator has the expected properties for alpha thrombin as detected by HPLC, clotting activity and mass spec.

Example 7

Purification of rEcarin

Cell culture supernatant (CC) containing the recombinant pre-pro-rEcarin and activated rEcarin was concentrated and purified (typical CC contains ~80% pre pro rEcarin and ~20% activated rEcarin). Concentration of the CC was performed by ultrafiltration (UF) using a 30 kD polyethersulfone ("PES") membrane (Millipore, Cat. #P2B030A01). Final volume following ultrafiltration was small enough to make loading onto the IMAC column convenient. Target concentrations were typically ~20× of the original starting volume of CC; thus a 100 L harvest would be concentrated down to 5 L. UF was followed by diafiltration (DF) into 25 mM HEPES and 250 mM NaCl at pH 8.0, a buffer compatible for activation and IMAC capture chromatography.

As mentioned, the recombinant rEcarin in cell supernatant is predominantly pre-pro-rEcarin. The pre-pro-rEcarin was then itself activated, using an enzymatic method. The UF/DF retentate was incubated overnight (~16 hours) with 50 µg/mL thrombin at 21° C. Additionally, in some purification runs, triton (Triton X-100, 10% solution, proteomics grade, Code: M236) was also added to a final concentration of 0.5% as an optional enveloped viral inactivation step.

After activation, the mature rEcarin was purified from the activated retentate using IMAC capture chromatography. The IMAC column uses Toyopearl AF chelate 650M resin (TOSOH BIOSCIENCE, Cat. #14475) prepared as follows: a 5-column volume (CV) rinse using dH$_2$O, followed by a 1-5 CV charge with 1 M ZnCl$_2$, followed by a 5 CV rinse with dH$_2$O, followed by a 5-10 CV equilibration with 25 mM HEPES, 250 mM NaCl, pH 8.0. The column was then loaded with conditioned UF/DF retentate, washed with 5 CV of 25 mM HEPES, 250 mM NaCl, pH 8.0 followed by a no salt wash with 5-10 CV of 25 mM HEPES, pH 8.0 specifically designed to remove HCP and other impurities hydrophobically bound to the column. Following the no salt wash, the column was prepared for elution with a third wash with 2-3 CV of 25 mM HEPES, 75 mM NaCl, pH 8.0. Elution was achieved with a 10 CV gradient from 100% of 25 mM HEPES, 75 mM NaCl, pH 8.0 to 50% Elution buffer of 25 mM HEPES, 75 mM NaCl, 150 mM Imidazole at pH 8.0.

A polishing step may then be performed. Several different approaches to polishing were successfully used to produce high purity active rEcarin suitable for coupling. These include: heparin chromatography, cation exchange chromatography (SPHP), anion exchange chromatography (DEAE), and buffer exchange using dialysis, UF/DF, or size exclusion chromatography.

Affinity chromatography was performed using Heparin resin (TOSOH BIOSCIENCE, Cat. #14474). Affinity chromatography was started by equilibrating the column with 5 CV of 25 mM sodium phosphate, 70 mM NaCl, pH 7.4. After equilibration, IMAC capture pool from above (i.e., with 75 mM NaCl in the elution pool) was prepared by diluting 1:10 with 25 mM sodium phosphate, pH 7.4, and then filtered. The adjusted filtered pool was then loaded onto the column, washed with 5 CV of equilibration buffer, and eluted with a 20 CV gradient from 0% to 100% elution buffer (elution buffer is 25 mM sodium phosphate, 1 M NaCl, pH 7.4). The purified rEcarin was then stored in 25 mM sodium phosphate, 0-1 M NaCl at pH 7.4. Pools were stored at −80° C. for stability.

Cation exchange chromatography (CIEX) was performed using SPHP resin (GE healthcare, Cat. #17-1087-03). CIEX was started by equilibrating the column with 5 CV of 25 mM sodium acetate at pH 5.5. After equilibration, IMAC capture pool from above (i.e., with 75 mM NaCl in the elution pool) was prepared by adjusting to pH 5.5 using acetic acid, and then filtered. The adjusted filtered IMAC pool was then loaded onto the column, followed by washing with 5 CV of equilibration buffer and elution with a 10 CV gradient from 0% to 100% elution buffer (elution buffer was 25 mM sodium acetate, 1 M NaCl at pH 5.5). The purified rEcarin was then stored in 25 mM sodium acetate, 0-1 M NaCl at pH 5.5. Pools were stored at −80° C. for stability.

Anion exchange chromatography (ALEX), an alternate to cation exchange chromatography, was performed using Toyopearl DEAE-650M resin (TOSOH BIOSCIENCE, Cat. #43201). ALEX was started by equilibrating the column with 5 CV of 25 mM HEPES at pH 8.0. After equilibration, IMAC capture pool from above (i.e., with 75 mM NaCl in the elution pool) was prepared by adjusting the conductivity to less than 1 mS/cm using Water For Injection (WFI), and then filtered. The adjusted filtered IMAC pool was then loaded onto the column, washed with 5 CV of equilibration buffer, and eluted with a 10 CV gradient from 0% to 100% elution buffer (elution buffer is 25 mM HEPES, 500 mM NaCl at pH 8.0). The purified rEcarin was then stored in 25 mM HEPES, O-500 mM NaCl at pH 8.0. Pools were stored at −80° C. for stability.

Several different buffer exchange processes may also be used on IMAC to produce rEcarin that can be coupled and used to activate Prethrombin. The key point is that the residual Imidazole in the IMAC pool (leftover from the elution) should be removed since it negatively affects the coupling process. Buffer exchange was performed using dialysis into 25 mM HEPES, 75 mM NaCl, pH 8.0, a buffer compatible with the coupling reaction, and this process generated material suitable for coupling. Additionally, other easily recognizable buffer exchange processes such as DF or SEC should also remove imidazole from the IMAC pool and generate rEcarin ready for coupling.

Example 8

Treatment of rEcarin in Solution or Immobilized rEcarin with Transition Metal Ions to Place Metal into the Active Site, Thereby Generating an Active rEcarin Species In general, a solution state rEcarin or immobilized rEcarin may be treated with $Cu^{2+}$, $Co^{2+}$, or $Ni^{2+}$, in concentrations ranging from 0.1 µM to 100 mM, for a time ranging from 1 min to 18 hr. The solution may range from pH 5.0 to pH 7.0. The counter-ion can be sulfate, chloride, acetate, or another anionic compound that yields a solution. It is possible that the addition of chelating agents or crown ethers may be used to deliver these metal ions to the enzyme active site. Additionally, the presence of detergents, such as Triton X-100, or solution-modifying agents such as polyethylene glycol (e.g., PEG3350) may be helpful in facilitating the addition of the metal to rEcarin.

Treatment of rEcarin in Solution:

Thirty (30) μL solution state rEcarin was treated with 5 μL of 200 mM of $Cu^{2+}$, $Co^{2+}$, or $Ni^{2+}$ for 3 hr at room temperature. These metal-treated rEcarin solutions were tested using an activity assay. Compared with PBS buffer, increases in activity of 1.2-fold to 14-fold were observed in the metal-treated reactions. A control experiment indicated that the increase in activity occurred when rEcarin was treated before the activity assay, and not when the metal was added only during the assay.

Treatment of Immobilized rEcarin:

rEcarin, purified by cation exchange and immobilized on a column, was treated with a 100 mM sodium acetate solution (pH 5.5) with 40 mM $Cu^{2+}$ for 20 min at room temperature. The column was then purged of the metal solution by flowing a 20 mM Tris, 70 mM NaCl, pH 7.4 solution through the column. Thrombin mass yield was increased by 25% relative to immobilized rEcarin not treated with $Cu^{2+}$.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

```
<160> NUMBER OF SEQ ID NOS: 105

<210> SEQ ID NO 1
<211> LENGTH: 1869
<212> TYPE: DNA
<213> ORGANISM: Artificial Sequence
<220> FEATURE:
<223> OTHER INFORMATION: Construct MPET1697,
      met-pre-pro-GPR-Metalloprotease-Disintegrin-Cys rich-His tag

<400> SEQUENCE: 1
atgatccaga ttctcttggt aattatatgc ttagcagttt ttccatatca aggttgctct     60
ataatcctgg gatctgggaa tgttaatgat tatgaagtag tgtatccaca aaaagtcact    120
gcattgccca aaggagcagt tcagcagcct gagcaaaagt atgaagatgc catgcaatat    180
gaatttgaag tgaagggaga gccagtggtc cttcacctag aaaaaaataa agaacttttt    240
tcagaagatt acagtgagac tcattattcg tctgatgaca gagaaattac aacaaaccct    300
tcagttgagg atcactgcta ttatcatgga cggatccaga atgatgctga gtcaactgca    360
agcatcagtg catgcaatgg tttgaaagga catttcaagc ttcgagggga gacgtacttt    420
attgaaccct tgaagattcc cgacagtgaa gcccatgcag tctacaaata tgaaaacata    480
gaaaatgagg atgaagcccc caaaatgtgt ggggtaaccc aggataattg ggaatcagat    540
gaacccatca aaaagacttt ggggccaaga gttcctcctc atgaacgaaa atttgagaaa    600
aaattcattg agcttgtcgt agttgtggac cacagtatgg tcacaaaata caacaatgat    660
tcaactgcta tccgcacatg gatctatgaa atgctcaaca ctgtaaatga gatctactta    720
cctttcaata ttcgtgtagc actggttggc ctagaatttt ggtgcaatgg tgacttgatt    780
aacgtgacat ccacagcaga tgatactttg cactcatttg gcgaatggcg cgcatcagat    840
ttgctgaatc gtaaacgcca tgatcatgct cagttactca cgaacgtgac actggatcat    900
tccactcttg gtatcacgtt cgtatatggc atgtgcaaat cagatcgttc tgtagaactt    960
attctggatt acagcaacat aacttttaat atggcatata tcattgccca tgagatgggt   1020
catagtctgg gcatgttaca tgacacaaaa ttctgtactt gtggggctaa accatgcatt   1080
atgtttggca aagaaagcat tccaccgccc aaagaattca gcagttgtag ttatgaccag   1140
```

-continued

```
tataacaagt atcttcttaa atataaccca aaatgcattc ttgatccacc tttgcgtaaa   1200
gatattgctt cacctgcagt ttgtggcaat gaaatttggg aggaaggtga agaatgtgat   1260
tgtggttctc ctgcagattg tcgcaatcca tgctgtgatg ctgcaacatg taaactgaaa   1320
ccaggggcag aatgtggcaa tggtgagtgt tgtgacaagt gcaagattcg taaagcaggc   1380
acagaatgcc ggccagcacg cgatgactgt gatgtcgctg aacactgcac tggccaatct   1440
gctgagtgtc cccgtaatga gttccaacgc aatggtcaac catgccttaa caactctggt   1500
tattgctaca atggggattg ccccatcatg ttaaaccaat gtattgctct ctttagtcca   1560
agtgcaactg tggctcaaga ttcatgtttt cagcgtaact tgcaaggcag ttactatggc   1620
tactgcacaa aggaaattgg ttactatggt aaacgctttc catgtgcacc acaagatgta   1680
aaatgtggcc gtttatactg cttagataat tcattcaaaa aaaatatgcg ttgcaagaac   1740
gactattcat acgcggatga aaataagggt atcgttgaac ctggtacaaa atgtgaagat   1800
ggtaaggtct gcatcaaccg caagtgtgtt gatgtgaata cagcctacca tcaccatcac   1860
catcactaa                                                          1869
```

<210> SEQ ID NO 2
<211> LENGTH: 622
<212> TYPE: PRT
<213> ORGANISM: Artificial Sequence
<220> FEATURE:
<223> OTHER INFORMATION: Construct MPET1697,
      met-pre-pro-GPR-Metalloprotease-Disintegrin-Cys rich-His tag

<400> SEQUENCE: 2

```
Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Asp Asp Arg Glu Ile
                85                  90                  95

Thr Thr Asn Pro Ser Val Glu Asp His Cys Tyr Tyr His Gly Arg Ile
            100                 105                 110

Gln Asn Asp Ala Glu Ser Thr Ala Ser Ile Ser Ala Cys Asn Gly Leu
        115                 120                 125

Lys Gly His Phe Lys Leu Arg Gly Glu Thr Tyr Phe Ile Glu Pro Leu
    130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Pro Arg Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
    210                 215                 220
```

```
Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
            245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
    290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
                405                 410                 415

Glu Glu Cys Asp Cys Gly Ser Pro Ala Asp Cys Arg Asn Pro Cys Cys
            420                 425                 430

Asp Ala Ala Thr Cys Lys Leu Lys Pro Gly Ala Glu Cys Gly Asn Gly
        435                 440                 445

Glu Cys Cys Asp Lys Cys Lys Ile Arg Lys Ala Gly Thr Glu Cys Arg
    450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro Cys Leu
                485                 490                 495

Asn Asn Ser Gly Tyr Cys Tyr Asn Gly Asp Cys Pro Ile Met Leu Asn
            500                 505                 510

Gln Cys Ile Ala Leu Phe Ser Pro Ser Ala Thr Val Ala Gln Asp Ser
        515                 520                 525

Cys Phe Gln Arg Asn Leu Gln Gly Ser Tyr Tyr Gly Tyr Cys Thr Lys
    530                 535                 540

Glu Ile Gly Tyr Tyr Gly Lys Arg Phe Pro Cys Ala Pro Gln Asp Val
545                 550                 555                 560

Lys Cys Gly Arg Leu Tyr Cys Leu Asp Asn Ser Phe Lys Lys Asn Met
                565                 570                 575

Arg Cys Lys Asn Asp Tyr Ser Tyr Ala Asp Glu Asn Lys Gly Ile Val
            580                 585                 590

Glu Pro Gly Thr Lys Cys Glu Asp Gly Lys Val Cys Ile Asn Arg Lys
        595                 600                 605

Cys Val Asp Val Asn Thr Ala Tyr His His His His His
    610                 615                 620

<210> SEQ ID NO 3
<211> LENGTH: 1869
<212> TYPE: DNA
```

<213> ORGANISM: Artificial Sequence
<220> FEATURE:
<223> OTHER INFORMATION: Construct MPET1696,
    met-pre-pro-TLGLI-Metalloprotease-Disintegrin-Cys rich-His tag

<400> SEQUENCE: 3

| | | | | | | |
|---|---|---|---|---|---|---|
| atgatccaga | ttctcttggt | aattatatgc | ttagcagttt | ttccatatca | aggttgctct | 60 |
| ataatcctgg | gatctgggaa | tgttaatgat | tatgaagtag | tgtatccaca | aaaagtcact | 120 |
| gcattgccca | aggagcagt | tcagcagcct | gagcaaaagt | atgaagatgc | catgcaatat | 180 |
| gaatttgaag | tgaagggaga | gccagtggtc | cttcacctag | aaaaaaataa | agaacttttt | 240 |
| tcagaagatt | acagtgagac | tcattattcg | tctgatgaca | gagaaattac | aacaaaccct | 300 |
| tcagttgagg | atcactgcta | ttatcatgga | cggatccaga | atgatgctga | gtcaactgca | 360 |
| agcatcagtg | catgcaatgg | tttgaaagga | catttcaagc | ttcgagggga | gacgtacttt | 420 |
| attgaaccct | tgaagattcc | cgacagtgaa | gcccatgcag | tctacaaata | tgaaaacata | 480 |
| gaaaatgagg | atgaagcccc | caaaatgtgt | ggggtaaccc | aggataattg | ggaatcagat | 540 |
| gaacccatca | aaaagacttt | ggggttaatt | gttcctcctc | atgaacgaaa | atttgagaaa | 600 |
| aaattcattg | agcttgtcgt | agttgtggac | cacagtatgg | tcacaaaata | caacaatgat | 660 |
| tcaactgcta | tccgcacatg | gatctatgaa | atgctcaaca | ctgtaaatga | gatctactta | 720 |
| cctttcaata | ttcgtgtagc | actggttggc | ctagaatttt | ggtgcaatgg | tgacttgatt | 780 |
| aacgtgacat | ccacagcaga | tgatactttg | cactcatttg | gcgaatggcg | cgcatcagat | 840 |
| ttgctgaatc | gtaaacgcca | tgatcatgct | cagttactca | cgaacgtgac | actggatcat | 900 |
| tccactcttg | gtatcacgtt | cgtatatggc | atgtgcaaat | cagatcgttc | tgtagaactt | 960 |
| attctggatt | acagcaacat | aactttaat | atggcatata | tcattgccca | tgagatgggt | 1020 |
| catagtctgg | gcatgttaca | tgacacaaaa | ttctgtactt | gtggggctaa | accatgcatt | 1080 |
| atgtttggca | agaaaagcat | tccaccgccc | aaagaattca | gcagttgtag | ttatgaccag | 1140 |
| tataacaagt | atcttcttaa | atataaccca | aaatgcattc | ttgatccacc | tttgcgtaaa | 1200 |
| gatattgctt | cacctgcagt | ttgtggcaat | gaaatttggg | aggaaggtga | agaatgtgat | 1260 |
| tgtggttctc | ctgcagattg | tcgcaatcca | tgctgtgatg | ctgcaacatg | taaactgaaa | 1320 |
| ccagggcag | aatgtggcaa | tggtgagtgt | tgtgacaagt | gcaagattcg | taaagcaggc | 1380 |
| acagaatgcc | ggccagcacg | cgatgactgt | gatgtcgctg | aacactgcac | tggccaatct | 1440 |
| gctgagtgtc | cccgtaatga | gttccaacgc | aatggtcaac | catgccttaa | caactctggt | 1500 |
| tattgctaca | tgggggattg | ccccatcatg | ttaaaccaat | gtattgctct | ctttagtcca | 1560 |
| agtgcaactg | tggctcaaga | ttcatgttttt | cagcgtaact | tgcaaggcag | ttactatggc | 1620 |
| tactgcacaa | aggaaattgg | ttactatggt | aaacgctttc | catgtgcacc | acaagatgta | 1680 |
| aaatgtggcc | gtttatactg | cttagataat | tcattcaaaa | aaatatgcg | ttgcaagaac | 1740 |
| gactattcat | acgcggatga | aaataagggt | atcgttgaac | ctggtacaaa | atgtgaagat | 1800 |
| ggtaaggtct | gcatcaaccg | caagtgtgtt | gatgtgaata | cagcctacca | tcaccatcac | 1860 |
| catcactaa | | | | | | 1869 |

<210> SEQ ID NO 4
<211> LENGTH: 622
<212> TYPE: PRT
<213> ORGANISM: Artificial Sequence
<220> FEATURE:
<223> OTHER INFORMATION: Construct MPET1696,
    met-pre-pro-TLGLI-Metalloprotease-Disintegrin-Cys rich-His tag

<400> SEQUENCE: 4

```
Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Arg Glu Ile
                85                  90                  95

Thr Thr Asn Pro Ser Val Glu Asp His Cys Tyr Tyr His Gly Arg Ile
                100                 105                 110

Gln Asn Asp Ala Glu Ser Thr Ala Ser Ile Ser Ala Cys Asn Gly Leu
            115                 120                 125

Lys Gly His Phe Lys Leu Arg Gly Glu Thr Tyr Phe Ile Glu Pro Leu
        130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Leu Ile Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
    370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
```

|  |  |  | 405 |  |  |  | 410 |  |  |  | 415 |  |  |
|--|--|--|--|--|--|--|--|--|--|--|--|--|--|

Glu Glu Cys Asp Cys Gly Ser Pro Ala Asp Cys Arg Asn Pro Cys Cys
              420              425              430

Asp Ala Ala Thr Cys Lys Leu Lys Pro Gly Ala Glu Cys Gly Asn Gly
              435              440              445

Glu Cys Cys Asp Lys Cys Lys Ile Arg Lys Ala Gly Thr Glu Cys Arg
        450              455              460

Pro Ala Arg Asp Asp Cys Asp Val Ala Glu His Cys Thr Gly Gln Ser
465              470              475              480

Ala Glu Cys Pro Arg Asn Glu Phe Gln Arg Asn Gly Gln Pro Cys Leu
              485              490              495

Asn Asn Ser Gly Tyr Cys Tyr Asn Gly Asp Cys Pro Ile Met Leu Asn
        500              505              510

Gln Cys Ile Ala Leu Phe Ser Pro Ser Ala Thr Val Ala Gln Asp Ser
              515              520              525

Cys Phe Gln Arg Asn Leu Gln Gly Ser Tyr Tyr Gly Tyr Cys Thr Lys
        530              535              540

Glu Ile Gly Tyr Tyr Gly Lys Arg Phe Pro Cys Ala Pro Gln Asp Val
545              550              555              560

Lys Cys Gly Arg Leu Tyr Cys Leu Asp Asn Ser Phe Lys Lys Asn Met
              565              570              575

Arg Cys Lys Asn Asp Tyr Ser Tyr Ala Asp Glu Asn Lys Gly Ile Val
        580              585              590

Glu Pro Gly Thr Lys Cys Glu Asp Gly Lys Val Cys Ile Asn Arg Lys
              595              600              605

Cys Val Asp Val Asn Thr Ala Tyr His His His His His His
        610              615              620

<210> SEQ ID NO 5
<211> LENGTH: 1404
<212> TYPE: DNA
<213> ORGANISM: Artificial Sequence
<220> FEATURE:
<223> OTHER INFORMATION: Construct pTAP488, otpa
     leader-TLGLI-Metalloprotease-Disintegrin-Cys rich

<400> SEQUENCE: 5

| | |
|---|---|
| atggatgcaa tgaagagagg gctctgctgt gtgctgctgc tgtgtggcgc cgtcttcgtt | 60 |
| tcgctcagcc aggaaatcca tgccgagttg agacgcttcc gtagatctac tttggggtta | 120 |
| attgttcctc ctcatgaacg aaaatttgag aaaaaattca ttgagcttgt cgtagttgtg | 180 |
| gaccacagta tggtcacaaa atacaacaat gattcaactg ctatccgcac atggatctat | 240 |
| gaaatgctca acactgtaaa tgagatctac ttacctttca atattcgtgt agcactggtt | 300 |
| ggcctagaat tttggtgcaa tggtgacttg attaacgtga catccacagc agatgatact | 360 |
| ttgcactcat ttggcgaatg gcgcgcatca gatttgctga atcgtaaacg ccatgatcat | 420 |
| gctcagttac tcacgaacgt gacactggat cattccactc ttggtatcac gttcgtatat | 480 |
| ggcatgtgca atcagatcg ttctgtagaa cttattctgg attacagcaa cataactttt | 540 |
| aatatggcat atatcattgc ccatgagatg ggtcatagtc tgggcatgtt acatgacaca | 600 |
| aaattctgta cttgtggggc taaaccatgc attatgtttg gcaagaaaag cattccaccg | 660 |
| cccaaagaat tcagcagttg tagttatgac cagtataaca agtatcttct taaatataac | 720 |
| ccaaaatgca ttcttgatcc acctttgcgt aaagatattg cttcacctgc agtttgtggc | 780 |
| aatgaaattt gggaggaagg tgaagaatgt gattgtggtt ctcctgcaga ttgtcgcaat | 840 |

```
ccatgctgtg atgctgcaac atgtaaactg aaaccagggg cagaatgtgg caatggtgag    900
tgttgtgaca agtgcaagat tcgtaaagca ggcacagaat gccggccagc acgcgatgac    960
tgtgatgtcg ctgaacactg cactggccaa tctgctgagt gtccccgtaa tgagttccaa   1020
cgcaatggtc aaccatgcct taacaactct ggttattgct acaatgggga ttgccccatc   1080
atgttaaacc aatgtattgc tctctttagt ccaagtgcaa ctgtggctca agattcatgt   1140
tttcagcgta acttgcaagg cagttactat ggctactgca caaaggaaat tggttactat   1200
ggtaaacgct ttccatgtgc accacaagat gtaaaatgtg ccgtttata ctgcttagat    1260
aattcattca aaaaaaatat gcgttgcaag aacgactatt catacgcgga tgaaaataag   1320
ggtatcgttg aacctggtac aaaatgtgaa gatggtaagg tctgcatcaa ccgcaagtgt   1380
gttgatgtga atacagccta ctaa                                          1404
```

<210> SEQ ID NO 6
<211> LENGTH: 467
<212> TYPE: PRT
<213> ORGANISM: Artificial Sequence
<220> FEATURE:
<223> OTHER INFORMATION: Construct pTAP488, otpa
      leader-TLGLI-Metalloprotease-Disintegrin-Cys rich

<400> SEQUENCE: 6

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ser Thr Leu Gly Leu Ile Val Pro Pro His Glu Arg Lys
        35                  40                  45

Phe Glu Lys Lys Phe Ile Glu Leu Val Val Val Asp His Ser Met
    50                  55                  60

Val Thr Lys Tyr Asn Asn Asp Ser Thr Ala Ile Arg Thr Trp Ile Tyr
65                  70                  75                  80

Glu Met Leu Asn Thr Val Asn Glu Ile Tyr Leu Pro Phe Asn Ile Arg
                85                  90                  95

Val Ala Leu Val Gly Leu Glu Phe Trp Cys Asn Gly Asp Leu Ile Asn
            100                 105                 110

Val Thr Ser Thr Ala Asp Asp Thr Leu His Ser Phe Gly Glu Trp Arg
        115                 120                 125

Ala Ser Asp Leu Leu Asn Arg Lys Arg His Asp His Ala Gln Leu Leu
    130                 135                 140

Thr Asn Val Thr Leu Asp His Ser Thr Leu Gly Ile Thr Phe Val Tyr
145                 150                 155                 160

Gly Met Cys Lys Ser Asp Arg Ser Val Glu Leu Ile Leu Asp Tyr Ser
                165                 170                 175

Asn Ile Thr Phe Asn Met Ala Tyr Ile Ile Ala His Glu Met Gly His
            180                 185                 190

Ser Leu Gly Met Leu His Asp Thr Lys Phe Cys Thr Cys Gly Ala Lys
        195                 200                 205

Pro Cys Ile Met Phe Gly Lys Glu Ser Ile Pro Pro Lys Glu Phe
    210                 215                 220

Ser Ser Cys Ser Tyr Asp Gln Tyr Asn Lys Tyr Leu Leu Lys Tyr Asn
225                 230                 235                 240

Pro Lys Cys Ile Leu Asp Pro Pro Leu Arg Lys Asp Ile Ala Ser Pro
                245                 250                 255
```

```
Ala Val Cys Gly Asn Glu Ile Trp Glu Glu Gly Glu Cys Asp Cys
            260                 265                 270
Gly Ser Pro Ala Asp Cys Arg Asn Pro Cys Cys Asp Ala Ala Thr Cys
        275                 280                 285
Lys Leu Lys Pro Gly Ala Glu Cys Gly Asn Gly Glu Cys Cys Asp Lys
    290                 295                 300
Cys Lys Ile Arg Lys Ala Gly Thr Glu Cys Arg Pro Ala Arg Asp Asp
305                 310                 315                 320
Cys Asp Val Ala Glu His Cys Thr Gly Gln Ser Ala Glu Cys Pro Arg
                325                 330                 335
Asn Glu Phe Gln Arg Asn Gly Gln Pro Cys Leu Asn Asn Ser Gly Tyr
            340                 345                 350
Cys Tyr Asn Gly Asp Cys Pro Ile Met Leu Asn Gln Cys Ile Ala Leu
        355                 360                 365
Phe Ser Pro Ser Ala Thr Val Ala Gln Asp Ser Cys Phe Gln Arg Asn
    370                 375                 380
Leu Gln Gly Ser Tyr Tyr Gly Tyr Cys Thr Lys Glu Ile Gly Tyr Tyr
385                 390                 395                 400
Gly Lys Arg Phe Pro Cys Ala Pro Gln Asp Val Lys Cys Gly Arg Leu
                405                 410                 415
Tyr Cys Leu Asp Asn Ser Phe Lys Lys Asn Met Arg Cys Lys Asn Asp
            420                 425                 430
Tyr Ser Tyr Ala Asp Glu Asn Lys Gly Ile Val Glu Pro Gly Thr Lys
        435                 440                 445
Cys Glu Asp Gly Lys Val Cys Ile Asn Arg Lys Cys Val Asp Val Asn
    450                 455                 460
Thr Ala Tyr
465

<210> SEQ ID NO 7
<211> LENGTH: 1422
<212> TYPE: DNA
<213> ORGANISM: Artificial Sequence
<220> FEATURE:
<223> OTHER INFORMATION: Construct pTAP498, otpa-TLGLI-Metalloprotease-
      Disintegrin-Cys rich-His tag

<400> SEQUENCE: 7
atggatgcaa tgaagagagg ctctgctgtt gtgctgctgc tgtgtggcgc cgtcttcgtt    60
tcgctcagcc aggaaatcca tgccgagttg agacgcttcc gtagatctac tttgggatta   120
attgttcctc ctcatgaacg aaaatttgag aaaaaattca ttgagcttgt cgtagttgtg   180
gaccacagta tggtcacaaa atacaacaat gattcaactg ctatccgcac atggatctat   240
gaaatgctca acactgtaaa tgagatctac ttacctttca atattcgtgt agcactggtt   300
ggcctagaat tttggtgcaa tggtgacttg attaacgtga catccacagc agatgatact   360
ttgcactcat ttgcgaatg gcgcgcatca gatttgctga atcgtaaacg ccatgatcat   420
gctcagttac tcacgaacgt gacactggat cattccactc ttggtatcac gttcgtatat   480
ggcatgtgca atcagatcg ttctgtagaa cttattctgg attacagcaa cataactttt   540
aatatggcat atatcattgc ccatgagatg ggtcatagtc tgggcatgtt acatgacaca   600
aaattctgta cttgtggggc taaccatgc attatgtttg caagaaaag cattccaccg   660 cccaaagaat tcagcagttg tagttatgac cagtataaca agtatcttct taaatataac   720
ccaaaatgca ttcttgatcc acctttgcgt aaagatattg cttcacctgc agtttgtggc   780
```

```
aatgaaattt gggaggaagg tgaagaatgt gattgtggtt ctcctgcaga ttgtcgcaat      840
ccatgctgtg atgctgcaac atgtaaactg aaaccagggg cagaatgtgg caatggtgag      900
tgttgtgaca gtgcaagat tcgtaaagca ggcacagaat gccggccagc acgcgatgac      960
tgtgatgtcg ctgaacactg cactggccaa tctgctgagt gtccccgtaa tgagttccaa     1020
cgcaatggtc aaccatgcct taacaactct ggttattgct acaatgggga ttgccccatc     1080
atgttaaacc aatgtattgc tctctttagt ccaagtgcaa ctgtggctca agattcatgt     1140
tttcagcgta acttgcaagg cagttactat ggctactgca caaggaaat tggttactat      1200 ggtaaacgct tccatgtgc accacaagat gtaaatgtg ccgtttata ctgcttagat        1260 aattcattca aaaaaatat gcgttgcaag aacgactatt catacgcgga tgaaataag       1320 ggtatcgttg aacctggtac aaaatgtgaa gatggtaagg tctgcatcaa ccgcaagtgt     1380
gttgatgtga atacagccta ccatcaccat caccatcact aa                        1422
```

<210> SEQ ID NO 8
<211> LENGTH: 473
<212> TYPE: PRT
<213> ORGANISM: Artificial Sequence
<220> FEATURE:
<223> OTHER INFORMATION: Construct pTAP498, otpa-TLGLI-Metalloprotease-
      Disintegrin-Cys rich-His tag

<400> SEQUENCE: 8

```
Met Asp Ala Met Lys Arg Gly Leu Cys Cys Val Leu Leu Cys Gly
1               5                   10                  15

Ala Val Phe Val Ser Leu Ser Gln Glu Ile His Ala Glu Leu Arg Arg
            20                  25                  30

Phe Arg Arg Ser Thr Leu Gly Leu Ile Val Pro Pro His Glu Arg Lys
        35                  40                  45

Phe Glu Lys Lys Phe Ile Glu Leu Val Val Val Asp His Ser Met
50                  55                  60

Val Thr Lys Tyr Asn Asn Asp Ser Thr Ala Ile Arg Thr Trp Ile Tyr
65                  70                  75                  80

Glu Met Leu Asn Thr Val Asn Glu Ile Tyr Leu Pro Phe Asn Ile Arg
                85                  90                  95

Val Ala Leu Val Gly Leu Glu Phe Trp Cys Asn Gly Asp Leu Ile Asn
            100                 105                 110

Val Thr Ser Thr Ala Asp Asp Thr Leu His Ser Phe Gly Glu Trp Arg
        115                 120                 125

Ala Ser Asp Leu Leu Asn Arg Lys Arg His Asp His Ala Gln Leu Leu
    130                 135                 140

Thr Asn Val Thr Leu Asp His Ser Thr Leu Gly Ile Thr Phe Val Tyr
145                 150                 155                 160

Gly Met Cys Lys Ser Asp Arg Ser Val Glu Leu Ile Leu Asp Tyr Ser
                165                 170                 175

Asn Ile Thr Phe Asn Met Ala Tyr Ile Ile Ala His Glu Met Gly His
            180                 185                 190

Ser Leu Gly Met Leu His Asp Thr Lys Phe Cys Thr Cys Gly Ala Lys
        195                 200                 205

Pro Cys Ile Met Phe Gly Lys Glu Ser Ile Pro Pro Lys Glu Phe
    210                 215                 220

Ser Ser Cys Ser Tyr Asp Gln Tyr Asn Lys Tyr Leu Leu Lys Tyr Asn
225                 230                 235                 240
```

Pro Lys Cys Ile Leu Asp Pro Pro Leu Arg Lys Asp Ile Ala Ser Pro
            245                 250                 255

Ala Val Cys Gly Asn Glu Ile Trp Glu Glu Gly Glu Cys Asp Cys
        260                 265                 270

Gly Ser Pro Ala Asp Cys Arg Asn Pro Cys Cys Asp Ala Ala Thr Cys
            275                 280                 285

Lys Leu Lys Pro Gly Ala Glu Cys Gly Asn Gly Glu Cys Cys Asp Lys
            290                 295                 300

Cys Lys Ile Arg Lys Ala Gly Thr Glu Cys Arg Pro Ala Arg Asp Asp
305                 310                 315                 320

Cys Asp Val Ala Glu His Cys Thr Gly Gln Ser Ala Glu Cys Pro Arg
                325                 330                 335

Asn Glu Phe Gln Arg Asn Gly Gln Pro Cys Leu Asn Asn Ser Gly Tyr
            340                 345                 350

Cys Tyr Asn Gly Asp Cys Pro Ile Met Leu Asn Gln Cys Ile Ala Leu
            355                 360                 365

Phe Ser Pro Ser Ala Thr Val Ala Gln Asp Ser Cys Phe Gln Arg Asn
370                 375                 380

Leu Gln Gly Ser Tyr Tyr Gly Tyr Cys Thr Lys Glu Ile Gly Tyr Tyr
385                 390                 395                 400

Gly Lys Arg Phe Pro Cys Ala Pro Gln Asp Val Lys Cys Gly Arg Leu
            405                 410                 415

Tyr Cys Leu Asp Asn Ser Phe Lys Lys Asn Met Arg Cys Lys Asn Asp
            420                 425                 430

Tyr Ser Tyr Ala Asp Glu Asn Lys Gly Ile Val Glu Pro Gly Thr Lys
            435                 440                 445

Cys Glu Asp Gly Lys Val Cys Ile Asn Arg Lys Cys Val Asp Val Asn
450                 455                 460

Thr Ala Tyr His His His His His His
465                 470

```
<210> SEQ ID NO 9
<211> LENGTH: 1407
<212> TYPE: DNA
<213> ORGANISM: Artificial Sequence
<220> FEATURE:
<223> OTHER INFORMATION: Construct pTAP497, otpa leader-Metalloprotease-
      Disintegrin-Cys rich-His tag

<400> SEQUENCE: 9
atggatgcaa tgaagagagg gctctgctgt gtgctgctgc tgtgtggcgc cgtcttcgtt      60
tcgctcagcc aggaaatcca tgccgagttg agacgcttcc gtagatctgt tcctcctcat     120
gaacgaaaat ttgagaaaaa attcattgag cttgtcgtag ttgtggacca cagtatggtc     180
acaaaataca caatgattc aactgctatc cgcacatgga tctatgaaat gctcaacact     240
gtaaatgaga tctacttacc tttcaatatt cgtgtagcac tggttggcct agaattttgg     300
tgcaatggtg acttgattaa cgtgacatcc acagcagatg atactttgca ctcatttggc     360
gaatggcgcg catcagattt gctgaatcgt aaacgccatg atcatgctca gttactcacg     420
aacgtgacac tggatcattc cactcttggt atcacgttcg tatatggcat gtgcaaatca     480
gatcgttctg tagaacttat tctggattac agcaacataa cttttaatat ggcatatatc     540
attgcccatg agatgggtca tagtctgggc atgttacatg acacaaaatt ctgtacttgt     600
ggggctaaac catgcattat gtttggcaaa gaaagcattc accgcccaa gaattcagc     660 agttgtagtt atgaccagta taacaagtat cttcttaaat ataacccaaa atgcattctt     720
```

```
gatccacctt tgcgtaaaga tattgcttca cctgcagttt gtggcaatga aatttgggag      780
gaaggtgaag aatgtgattg tggttctcct gcagattgtc gcaatccatg ctgtgatgct      840
gcaacatgta aactgaaacc aggggcagaa tgtggcaatg gtgagtgttg tgacaagtgc      900
aagattcgta agcaggcac agaatgccgg ccagcacgcg atgactgtga tgtcgctgaa       960
cactgcactg ccaatctgc tgagtgtccc cgtaatgagt tccaacgcaa tggtcaacca      1020
tgccttaaca actctggtta ttgctacaat ggggattgcc ccatcatgtt aaaccaatgt     1080
attgctctct ttagtccaag tgcaactgtg gctcaagatt catgttttca gcgtaacttg     1140
caaggcagtt actatggcta ctgcacaaag gaaattggtt actatggtaa acgctttcca    1200
tgtgcaccac aagatgtaaa atgtggccgt ttatactgct tagataattc attcaaaaaa    1260
aatatgcgtt gcaagaacga ctattcatac gcggatgaaa ataagggtat cgttgaacct    1320
ggtacaaaat gtgaagatgg taaggtctgc atcaaccgca agtgtgttga tgtgaataca    1380
gcctaccatc accatcacca tcactaa                                         1407
```

<210> SEQ ID NO 10
<211> LENGTH: 468
<212> TYPE: PRT
<213> ORGANISM: Artificial Sequence
<220> FEATURE:
<223> OTHER INFORMATION: Construct pTAP497, otpa leader-Metalloprotease-
      Disintegrin-Cys rich-His tag

<400> SEQUENCE: 10

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ser Val Pro Pro His Glu Arg Lys Phe Glu Lys Lys Phe
        35                  40                  45

Ile Glu Leu Val Val Val Val Asp His Ser Met Val Thr Lys Tyr Asn
    50                  55                  60

Asn Asp Ser Thr Ala Ile Arg Thr Trp Ile Tyr Glu Met Leu Asn Thr
65                  70                  75                  80

Val Asn Glu Ile Tyr Leu Pro Phe Asn Ile Arg Val Ala Leu Val Gly
                85                  90                  95

Leu Glu Phe Trp Cys Asn Gly Asp Leu Ile Asn Val Thr Ser Thr Ala
            100                 105                 110

Asp Asp Thr Leu His Ser Phe Gly Glu Trp Arg Ala Ser Asp Leu Leu
        115                 120                 125

Asn Arg Lys Arg His Asp His Ala Gln Leu Leu Thr Asn Val Thr Leu
    130                 135                 140

Asp His Ser Thr Leu Gly Ile Thr Phe Val Tyr Gly Met Cys Lys Ser
145                 150                 155                 160

Asp Arg Ser Val Glu Leu Ile Leu Asp Tyr Ser Asn Ile Thr Phe Asn
                165                 170                 175

Met Ala Tyr Ile Ile Ala His Glu Met Gly His Ser Leu Gly Met Leu
            180                 185                 190

His Asp Thr Lys Phe Cys Thr Cys Gly Ala Lys Pro Cys Ile Met Phe
        195                 200                 205

Gly Lys Glu Ser Ile Pro Pro Lys Glu Phe Ser Ser Cys Ser Tyr
    210                 215                 220

Asp Gln Tyr Asn Lys Tyr Leu Leu Lys Tyr Asn Pro Lys Cys Ile Leu
```

```
                225                 230                 235                 240
Asp Pro Pro Leu Arg Lys Asp Ile Ala Ser Pro Ala Val Cys Gly Asn
                    245                 250                 255
Glu Ile Trp Glu Glu Gly Glu Cys Asp Cys Gly Ser Pro Ala Asp
                260                 265                 270
Cys Arg Asn Pro Cys Cys Asp Ala Ala Thr Cys Lys Leu Lys Pro Gly
                275                 280                 285
Ala Glu Cys Gly Asn Gly Glu Cys Cys Asp Lys Cys Lys Ile Arg Lys
            290                 295                 300
Ala Gly Thr Glu Cys Arg Pro Ala Arg Asp Asp Cys Asp Val Ala Glu
305                 310                 315                 320
His Cys Thr Gly Gln Ser Ala Glu Cys Pro Arg Asn Glu Phe Gln Arg
                325                 330                 335
Asn Gly Gln Pro Cys Leu Asn Asn Ser Gly Tyr Cys Tyr Asn Gly Asp
                340                 345                 350
Cys Pro Ile Met Leu Asn Gln Cys Ile Ala Leu Phe Ser Pro Ser Ala
                355                 360                 365
Thr Val Ala Gln Asp Ser Cys Phe Gln Arg Asn Leu Gln Gly Ser Tyr
            370                 375                 380
Tyr Gly Tyr Cys Thr Lys Glu Ile Gly Tyr Tyr Gly Lys Arg Phe Pro
385                 390                 395                 400
Cys Ala Pro Gln Asp Val Lys Cys Gly Arg Leu Tyr Cys Leu Asp Asn
                    405                 410                 415
Ser Phe Lys Lys Asn Met Arg Cys Lys Asn Asp Tyr Ser Tyr Ala Asp
                420                 425                 430
Glu Asn Lys Gly Ile Val Glu Pro Gly Thr Lys Cys Glu Asp Gly Lys
            435                 440                 445
Val Cys Ile Asn Arg Lys Cys Val Asp Val Asn Thr Ala Tyr His His
                450                 455                 460
His His His His
465

<210> SEQ ID NO 11
<211> LENGTH: 1422
<212> TYPE: DNA
<213> ORGANISM: Artificial Sequence
<220> FEATURE:
<223> OTHER INFORMATION: Construct pTAP502, otpa leader-His
      tag-TLGLI-Metalloprotease-Disintegrin-Cys rich

<400> SEQUENCE: 11
atggatgcaa tgaagagagg ctctgctgt gtgctgctgc tgtgtggcgc cgtcttcgtt      60
tcgctcagcc aggaaatcca tgccgagttg agacgcttcc gtagatctca tcaccatcac     120
catcacactt tggggttaat tgttcctcct catgaacgaa atttgagaa aaaattcatt     180 gagcttgtcg tagttgtgga ccacagtatg gtcacaaaat acaacaatga ttcaactgct     240
atccgcacat ggatctatga aatgctcaac actgtaaatg agatctactt acctttcaat     300
attcgtgtag cactggttgg cctagaattt tggtgcaatg gtgacttgat taacgtgaca     360
tccacagcag atgatacttt gcactcattt ggcgaatggc gcgcatcaga tttgctgaat     420
cgtaaacgcc atgatcatgc tcagttactc acgaacgtga cactggatca ttccactctt     480
ggtatcacgt tcgtatatgg catgtgcaaa tcagatcgtt ctgtagaact tattctggat     540
tacagcaaca taacttttaa tatggcatat atcattgccc atgagatggg tcatagtctg     600
ggcatgttac atgacacaaa attctgtact tgtggggcta aaccatgcat tatgtttggc     660
```

-continued

```
aaagaaagca ttccaccgcc caaagaattc agcagttgta gttatgacca gtataacaag    720
tatcttctta aatataaccc aaaatgcatt cttgatccac ctttgcgtaa agatattgct    780
tcacctgcag tttgtggcaa tgaaatttgg gaggaaggtg aagaatgtga ttgtggttct    840
cctgcagatt gtcgcaatcc atgctgtgat gctgcaacat gtaaactgaa accaggggca    900
gaatgtggca atggtgagtg ttgtgacaag tgcaagattc gtaaagcagg cacagaatgc    960
cggccagcac gcgatgactg tgatgtcgct gaacactgca ctggccaatc tgctgagtgt   1020
ccccgtaatg agttccaacg caatggtcaa ccatgcctta caactctggt tattgctac    1080 aatgggatt gccccatcat gttaaaccaa tgtattgctc tctttagtcc aagtgcaact    1140
gtggctcaag attcatgttt tcagcgtaac ttgcaaggca gttactatgg ctactgcaca   1200
aaggaaattg gttactatgg taaacgcttt ccatgtgcac cacaagatgt aaaatgtggc   1260
cgtttatact gcttagataa ttcattcaaa aaaaatatgc gttgcaagaa cgactattca   1320
tacgcggata aaaataaggg tatcgttgaa cctggtacaa aatgtgaaga tggtaaggtc   1380
tgcatcaacc gcaagtgtgt tgatgtgaat acagcctact aa                     1422
```

<210> SEQ ID NO 12
<211> LENGTH: 473
<212> TYPE: PRT
<213> ORGANISM: Artificial Sequence
<220> FEATURE:
<223> OTHER INFORMATION: Construct pTAP502, otpa leader-His
      tag-TLGLI-Metalloprotease-Disintegrin-Cys rich

<400> SEQUENCE: 12

```
Met Asp Ala Met Lys Arg Gly Leu Cys Cys Val Leu Leu Cys Gly
1               5                  10                  15

Ala Val Phe Val Ser Leu Ser Gln Glu Ile His Ala Glu Leu Arg Arg
                20                  25                  30

Phe Arg Arg Ser His His His His His His Thr Leu Gly Leu Ile Val
            35                  40                  45

Pro Pro His Glu Arg Lys Phe Glu Lys Lys Phe Ile Glu Leu Val Val
        50                  55                  60

Val Val Asp His Ser Met Val Thr Lys Tyr Asn Asn Asp Ser Thr Ala
65                  70                  75                  80

Ile Arg Thr Trp Ile Tyr Glu Met Leu Asn Thr Val Asn Glu Ile Tyr
                85                  90                  95

Leu Pro Phe Asn Ile Arg Val Ala Leu Val Gly Leu Glu Phe Trp Cys
            100                 105                 110

Asn Gly Asp Leu Ile Asn Val Thr Ser Thr Ala Asp Asp Thr Leu His
        115                 120                 125

Ser Phe Gly Glu Trp Arg Ala Ser Asp Leu Leu Asn Arg Lys Arg His
    130                 135                 140

Asp His Ala Gln Leu Leu Thr Asn Val Thr Leu Asp His Ser Thr Leu
145                 150                 155                 160

Gly Ile Thr Phe Val Tyr Gly Met Cys Lys Ser Asp Arg Ser Val Glu
                165                 170                 175

Leu Ile Leu Asp Tyr Ser Asn Ile Thr Phe Asn Met Ala Tyr Ile Ile
            180                 185                 190

Ala His Glu Met Gly His Ser Leu Gly Met Leu His Asp Thr Lys Phe
        195                 200                 205

Cys Thr Cys Gly Ala Lys Pro Cys Ile Met Phe Gly Lys Glu Ser Ile
    210                 215                 220
```

-continued

```
Pro Pro Pro Lys Glu Phe Ser Ser Cys Ser Tyr Asp Gln Tyr Asn Lys
225                 230                 235                 240

Tyr Leu Leu Lys Tyr Asn Pro Lys Cys Ile Leu Asp Pro Pro Leu Arg
            245                 250                 255

Lys Asp Ile Ala Ser Pro Ala Val Cys Gly Asn Glu Ile Trp Glu Glu
        260                 265                 270

Gly Glu Glu Cys Asp Cys Gly Ser Pro Ala Asp Cys Arg Asn Pro Cys
    275                 280                 285

Cys Asp Ala Ala Thr Cys Lys Leu Lys Pro Gly Ala Glu Cys Gly Asn
290                 295                 300

Gly Glu Cys Cys Asp Lys Cys Lys Ile Arg Lys Ala Gly Thr Glu Cys
305                 310                 315                 320

Arg Pro Ala Arg Asp Asp Cys Asp Val Ala Glu His Cys Thr Gly Gln
                325                 330                 335

Ser Ala Glu Cys Pro Arg Asn Glu Phe Gln Arg Asn Gly Gln Pro Cys
            340                 345                 350

Leu Asn Asn Ser Gly Tyr Cys Tyr Asn Gly Asp Cys Pro Ile Met Leu
        355                 360                 365

Asn Gln Cys Ile Ala Leu Phe Ser Pro Ser Ala Thr Val Ala Gln Asp
370                 375                 380

Ser Cys Phe Gln Arg Asn Leu Gln Gly Ser Tyr Tyr Gly Tyr Cys Thr
385                 390                 395                 400

Lys Glu Ile Gly Tyr Tyr Gly Lys Arg Phe Pro Cys Ala Pro Gln Asp
                405                 410                 415

Val Lys Cys Gly Arg Leu Tyr Cys Leu Asp Asn Ser Phe Lys Lys Asn
            420                 425                 430

Met Arg Cys Lys Asn Asp Tyr Ser Tyr Ala Asp Glu Asn Lys Gly Ile
        435                 440                 445

Val Glu Pro Gly Thr Lys Cys Glu Asp Gly Lys Val Cys Ile Asn Arg
    450                 455                 460

Lys Cys Val Asp Val Asn Thr Ala Tyr
465                 470

<210> SEQ ID NO 13
<211> LENGTH: 765
<212> TYPE: DNA
<213> ORGANISM: Artificial Sequence
<220> FEATURE:
<223> OTHER INFORMATION: Construct pTAP504, otpa leader-TLGLI-
      Metalloprotease-His tag

<400> SEQUENCE: 13
atggatgcaa tgaagagagg gctctgctgt gtgctgctgc tgtgtggcgc cgtcttcgtt      60
tcgctcagcc aggaaatcca tgccgagttg agacgcttcc gtagatctac tttggggtta    120
attgttcctc tcatgaacg aaatttgag aaaaaattca ttgagcttgt cgtagttgtg     180
gaccacagta tggtcacaaa atacaacaat gattcaactg ctatccgcac atggatctat    240
gaaatgctca cactgtaaa tgagatctac ttacctttca atattcgtgt agcactggtt    300
ggcctagaat tttggtgcaa tggtgacttg attaacgtga catccacagc agatgatact    360
ttgcactcat ttggcgaatg gcgcgcatca gatttgctga atcgtaaacg ccatgatcat    420
gctcagttac tcacgaacgt gacactggat cattccactc ttggtatcac gttcgtatat    480
ggcatgtgca aatcagatcg ttctgtagaa cttattctgg attacagcaa cataactttt    540
aatatggcat atatcattgc ccatgagatg ggtcatagtc tgggcatgtt acatgacaca    600
```

```
aaattctgta cttgtggggc taaaccatgc attatgtttg gcaaagaaag cattccaccg        660
cccaaagaat tcagcagttg tagttatgac cagtataaca agtatcttct taaatataac        720
ccaaaatgca ttcttgatcc acctcatcac catcaccatc actaa                        765
```

<210> SEQ ID NO 14
<211> LENGTH: 254
<212> TYPE: PRT
<213> ORGANISM: Artificial Sequence
<220> FEATURE:
<223> OTHER INFORMATION: Construct pTAP504, otpa leader-TLGLI-
      Metalloprotease-His tag

<400> SEQUENCE: 14

```
Met Asp Ala Met Lys Arg Gly Leu Cys Cys Val Leu Leu Cys Gly
1               5                   10                  15

Ala Val Phe Val Ser Leu Ser Gln Glu Ile His Ala Glu Leu Arg Arg
                20                  25                  30

Phe Arg Arg Ser Thr Leu Gly Leu Ile Val Pro Pro His Glu Arg Lys
            35                  40                  45

Phe Glu Lys Lys Phe Ile Glu Leu Val Val Val Asp His Ser Met
50                  55                  60

Val Thr Lys Tyr Asn Asn Asp Ser Thr Ala Ile Arg Thr Trp Ile Tyr
65                  70                  75                  80

Glu Met Leu Asn Thr Val Asn Glu Ile Tyr Leu Pro Phe Asn Ile Arg
                85                  90                  95

Val Ala Leu Val Gly Leu Glu Phe Trp Cys Asn Gly Asp Leu Ile Asn
            100                 105                 110

Val Thr Ser Thr Ala Asp Asp Thr Leu His Ser Phe Gly Glu Trp Arg
        115                 120                 125

Ala Ser Asp Leu Leu Asn Arg Lys Arg His Asp His Ala Gln Leu Leu
130                 135                 140

Thr Asn Val Thr Leu Asp His Ser Thr Leu Gly Ile Thr Phe Val Tyr
145                 150                 155                 160

Gly Met Cys Lys Ser Asp Arg Ser Val Glu Leu Ile Leu Asp Tyr Ser
                165                 170                 175

Asn Ile Thr Phe Asn Met Ala Tyr Ile Ile Ala His Glu Met Gly His
            180                 185                 190

Ser Leu Gly Met Leu His Asp Thr Lys Phe Cys Thr Cys Gly Ala Lys
        195                 200                 205

Pro Cys Ile Met Phe Gly Lys Glu Ser Ile Pro Pro Lys Glu Phe
    210                 215                 220

Ser Ser Cys Ser Tyr Asp Gln Tyr Asn Lys Tyr Leu Leu Lys Tyr Asn
225                 230                 235                 240

Pro Lys Cys Ile Leu Asp Pro Pro His His His His His His
                245                 250
```

<210> SEQ ID NO 15
<211> LENGTH: 750
<212> TYPE: DNA
<213> ORGANISM: Artificial Sequence
<220> FEATURE:
<223> OTHER INFORMATION: Construct pTAP495, otpa leader-
      Metalloprotease-His tag

<400> SEQUENCE: 15

```
atggatgcaa tgaagagagg gctctgctgt gtgctgctgc tgtgtggcgc cgtcttcgtt        60
```

```
tcgctcagcc aggaaatcca tgccgagttg agacgcttcc gtagatctgt tcctcctcat      120
gaacgaaaat ttgagaaaaa attcattgag cttgtcgtag ttgtggacca cagtatggtc      180
acaaaataca acaatgattc aactgctatc cgcacatgga tctatgaaat gctcaacact      240
gtaaatgaga tctacttacc tttcaatatt cgtgtagcac tggttggcct agaattttgg      300
tgcaatggtg acttgattaa cgtgacatcc acagcagatg atactttgca ctcatttggc      360
gaatggcgcg catcagattt gctgaatcgt aaagccatg atcatgctca gttactcacg       420
aacgtgacac tggatcattc cactcttggt atcacgttcg tatatggcat gtgcaaatca      480
gatcgttctg tagaacttat tctggattac agcaacataa cttttaatat ggcatatatc      540
attgcccatg agatgggtca tagtctgggc atgttacatg acacaaaatt ctgtacttgt      600
ggggctaaac catgcattat gtttggcaaa gaaagcattc caccgcccaa agaattcagc      660
agttgtagtt atgaccagta taacaagtat cttcttaaat ataacccaaa atgcattctt      720
gatccacctc atcaccatca ccatcactaa                                        750
```

```
<210> SEQ ID NO 16
<211> LENGTH: 249
<212> TYPE: PRT
<213> ORGANISM: Artificial Sequence
<220> FEATURE:
<223> OTHER INFORMATION: Construct pTAP495, otpa leader-
      Metalloprotease-His tag

<400> SEQUENCE: 16

Met Asp Ala Met Lys Arg Gly Leu Cys Cys Val Leu Leu Cys Gly
1               5                   10                  15

Ala Val Phe Val Ser Leu Ser Gln Glu Ile His Ala Glu Leu Arg Arg
            20                  25                  30

Phe Arg Arg Ser Val Pro Pro His Glu Arg Lys Phe Glu Lys Lys Phe
        35                  40                  45

Ile Glu Leu Val Val Val Asp His Ser Met Val Thr Lys Tyr Asn
    50                  55                  60

Asn Asp Ser Thr Ala Ile Arg Thr Trp Ile Tyr Glu Met Leu Asn Thr
65                  70                  75                  80

Val Asn Glu Ile Tyr Leu Pro Phe Asn Ile Arg Val Ala Leu Val Gly
                85                  90                  95

Leu Glu Phe Trp Cys Asn Gly Asp Leu Ile Asn Val Thr Ser Thr Ala
            100                 105                 110

Asp Asp Thr Leu His Ser Phe Gly Glu Trp Arg Ala Ser Asp Leu Leu
        115                 120                 125

Asn Arg Lys Arg His Asp His Ala Gln Leu Leu Thr Asn Val Thr Leu
    130                 135                 140

Asp His Ser Thr Leu Gly Ile Thr Phe Val Tyr Gly Met Cys Lys Ser
145                 150                 155                 160

Asp Arg Ser Val Glu Leu Ile Leu Asp Tyr Ser Asn Ile Thr Phe Asn
                165                 170                 175

Met Ala Tyr Ile Ile Ala His Glu Met Gly His Ser Leu Gly Met Leu
            180                 185                 190

His Asp Thr Lys Phe Cys Thr Cys Gly Ala Lys Pro Cys Ile Met Phe
        195                 200                 205

Gly Lys Glu Ser Ile Pro Pro Lys Glu Phe Ser Ser Cys Ser Tyr
    210                 215                 220

Asp Gln Tyr Asn Lys Tyr Leu Leu Lys Tyr Asn Pro Lys Cys Ile Leu
225                 230                 235                 240
```

Asp Pro Pro His His His His His His
                245

<210> SEQ ID NO 17
<211> LENGTH: 1977
<212> TYPE: DNA
<213> ORGANISM: Artificial Sequence
<220> FEATURE:
<223> OTHER INFORMATION: Construct pTAP540, otpa
      leader-pre-pro-GPR-Metalloprotease-Disintegrin-Cys rich-His tag

<400> SEQUENCE: 17

| | | | | |
|---|---|---|---|---|
| atggatgcaa | tgaagagagg | gctctgctgt | gtgctgctgc | tgtgtggcgc | cgtcttcgtt | 60 |
| tcgctcagcc | aggaaatcca | tgccgagttg | agacgcttcc | gtagatctat | gatccagatt | 120 |
| ctcttggtaa | ttatatgctt | agcagttttt | ccatatcaag | gttgctctat | aatcctggga | 180 |
| tctgggaatg | ttaatgatta | tgaagtagtg | tatccacaaa | aagtcactgc | attgcccaaa | 240 |
| ggagcagttc | agcagcctga | gcaaaagtat | gaagatgcca | tgcaatatga | atttgaagtg | 300 |
| aagggagagc | cagtggtcct | tcacctagaa | aaaataaag | aacttttttc | agaagattac | 360 |
| agtgagactc | attattcgtc | tgatgacaga | gaaattacaa | caaacccttc | agttgaggat | 420 |
| cactgctatt | atcatggacg | gatccagaat | gatgctgagt | caactgcaag | catcagtgca | 480 |
| tgcaatggtt | tgaaaggaca | tttcaagctt | cgagggggaga | cgtactttat | tgaacccttg | 540 |
| aagattcccg | acagtgaagc | ccatgcagtc | tacaaatatg | aaaacataga | aatgaggat | 600 |
| gaagcccca | aaatgtgtgg | ggtaacccag | gataattggg | aatcagatga | acccatcaaa | 660 |
| aagactttgg | ggccaagagt | tcctcctcat | gaacgaaaat | ttgagaaaaa | attcattgag | 720 |
| cttgtcgtag | ttgtggacca | cagtatggtc | acaaaataca | acaatgattc | aactgctatc | 780 |
| cgcacatgga | tctatgaaat | gctcaacact | gtaaatgaga | tctacttacc | tttcaatatt | 840 |
| cgtgtagcac | tggttggcct | agaattttg | tgcaatggtg | acttgattaa | cgtgacatcc | 900 |
| acagcagatg | atactttgca | ctcatttggc | gaatggcgcg | catcagattt | gctgaatcgt | 960 |
| aaacgccatg | atcatgctca | gttactcacg | aacgtgacac | tggatcattc | cactcttggt | 1020 |
| atcacgttcg | tatatggcat | gtgcaaatca | gatcgttctg | tagaacttat | tctggattac | 1080 |
| agcaacataa | cttttaatat | ggcatatatc | attgcccatg | agatgggtca | tagtctgggc | 1140 |
| atgttacatg | acacaaaatt | ctgtacttgt | ggggctaaac | catgcattat | gtttggcaaa | 1200 |
| gaaagcattc | caccgcccaa | agaattcagc | agttgtagtt | atgaccagta | taacaagtat | 1260 |
| cttcttaaat | ataacccaaa | atgcattctt | gatccacctt | tgcgtaaaga | tattgcttca | 1320 |
| cctgcagttt | gtggcaatga | aatttgggag | gaaggtgaag | aatgtgattg | tggttctcct | 1380 |
| gcagattgtc | gcaatccatg | ctgtgatgct | gcaacatgta | aactgaaacc | aggggcagaa | 1440 |
| tgtggcaatg | gtgagtgttg | tgacaagtgc | aagattcgta | aagcaggcac | agaatgccgg | 1500 |
| ccagcacgcg | atgactgtga | tgtcgctgaa | cactgcactg | gccaatctgc | tgagtgtccc | 1560 |
| cgtaatgagt | tccaacgcaa | tggtcaacca | tgccttaaca | actctggtta | ttgctacaat | 1620 |
| ggggattgcc | ccatcatgtt | aaaccaatgt | attgctctct | ttagtccaag | tgcaactgtg | 1680 |
| gctcaagatt | catgttttca | gcgtaacttg | caaggcagtt | actatggcta | ctgcacaaag | 1740 |
| gaaattggtt | actatggtaa | acgctttcca | tgtgcaccac | aagatgtaaa | atgtggccgt | 1800 |
| ttatactgct | tagataattc | attcaaaaaa | aatatgcgtt | gcaagaacga | ctattcatac | 1860 |
| gcggatgaaa | ataagggtat | cgttgaacct | ggtacaaaat | gtgaagatgg | taaggtctgc | 1920 | atcaaccgca agtgtgttga tgtgaataca gcctaccatc accatcacca tcactaa 1977

<210> SEQ ID NO 18
<211> LENGTH: 658
<212> TYPE: PRT
<213> ORGANISM: Artificial Sequence
<220> FEATURE:
<223> OTHER INFORMATION: Construct pTAP540, otpa
      leader-pre-pro-GPR-Metalloprotease-Disintegrin-Cys rich-His tag

<400> SEQUENCE: 18

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ser Met Ile Gln Ile Leu Leu Val Ile Ile Cys Leu Ala
        35                  40                  45

Val Phe Pro Tyr Gln Gly Cys Ser Ile Ile Leu Gly Ser Gly Asn Val
    50                  55                  60

Asn Asp Tyr Glu Val Val Tyr Pro Gln Lys Val Thr Ala Leu Pro Lys
65                  70                  75                  80

Gly Ala Val Gln Gln Pro Glu Gln Lys Tyr Glu Asp Ala Met Gln Tyr
                85                  90                  95

Glu Phe Glu Val Lys Gly Glu Pro Val Val Leu His Leu Glu Lys Asn
            100                 105                 110

Lys Glu Leu Phe Ser Glu Asp Tyr Ser Glu Thr His Tyr Ser Ser Asp
        115                 120                 125

Asp Arg Glu Ile Thr Thr Asn Pro Ser Val Glu Asp His Cys Tyr Tyr
    130                 135                 140

His Gly Arg Ile Gln Asn Asp Ala Glu Ser Thr Ala Ser Ile Ser Ala
145                 150                 155                 160

Cys Asn Gly Leu Lys Gly His Phe Lys Leu Arg Gly Glu Thr Tyr Phe
                165                 170                 175

Ile Glu Pro Leu Lys Ile Pro Asp Ser Glu Ala His Ala Val Tyr Lys
            180                 185                 190

Tyr Glu Asn Ile Glu Asn Glu Asp Glu Ala Pro Lys Met Cys Gly Val
        195                 200                 205

Thr Gln Asp Asn Trp Glu Ser Asp Glu Pro Ile Lys Lys Thr Leu Gly
    210                 215                 220

Pro Arg Val Pro Pro His Glu Arg Lys Phe Glu Lys Lys Phe Ile Glu
225                 230                 235                 240

Leu Val Val Val Val Asp His Ser Met Val Thr Lys Tyr Asn Asn Asp
                245                 250                 255

Ser Thr Ala Ile Arg Thr Trp Ile Tyr Glu Met Leu Asn Thr Val Asn
            260                 265                 270

Glu Ile Tyr Leu Pro Phe Asn Ile Arg Val Ala Leu Val Gly Leu Glu
        275                 280                 285

Phe Trp Cys Asn Gly Asp Leu Ile Asn Val Thr Ser Thr Ala Asp Asp
    290                 295                 300

Thr Leu His Ser Phe Gly Glu Trp Arg Ala Ser Asp Leu Leu Asn Arg
305                 310                 315                 320

Lys Arg His Asp His Ala Gln Leu Leu Thr Asn Val Thr Leu Asp His
                325                 330                 335

Ser Thr Leu Gly Ile Thr Phe Val Tyr Gly Met Cys Lys Ser Asp Arg
            340                 345                 350
```

```
Ser Val Glu Leu Ile Leu Asp Tyr Ser Asn Ile Thr Phe Asn Met Ala
            355                 360                 365
Tyr Ile Ile Ala His Glu Met Gly His Ser Leu Gly Met Leu His Asp
        370                 375                 380
Thr Lys Phe Cys Thr Cys Gly Ala Lys Pro Cys Ile Met Phe Gly Lys
385                 390                 395                 400
Glu Ser Ile Pro Pro Lys Glu Phe Ser Ser Cys Ser Tyr Asp Gln
                405                 410                 415
Tyr Asn Lys Tyr Leu Leu Lys Tyr Pro Lys Cys Ile Leu Asp Pro
            420                 425                 430
Pro Leu Arg Lys Asp Ile Ala Ser Pro Ala Val Cys Gly Asn Glu Ile
        435                 440                 445
Trp Glu Glu Gly Glu Glu Cys Asp Cys Gly Ser Pro Ala Asp Cys Arg
    450                 455                 460
Asn Pro Cys Cys Asp Ala Ala Thr Cys Lys Leu Lys Pro Gly Ala Glu
465                 470                 475                 480
Cys Gly Asn Gly Glu Cys Cys Asp Lys Cys Lys Ile Arg Lys Ala Gly
                485                 490                 495
Thr Glu Cys Arg Pro Ala Arg Asp Asp Cys Asp Val Ala Glu His Cys
            500                 505                 510
Thr Gly Gln Ser Ala Glu Cys Pro Arg Asn Glu Phe Gln Arg Asn Gly
        515                 520                 525
Gln Pro Cys Leu Asn Asn Ser Gly Tyr Cys Tyr Asn Gly Asp Cys Pro
    530                 535                 540
Ile Met Leu Asn Gln Cys Ile Ala Leu Phe Ser Pro Ser Ala Thr Val
545                 550                 555                 560
Ala Gln Asp Ser Cys Phe Gln Arg Asn Leu Gln Gly Ser Tyr Tyr Gly
                565                 570                 575
Tyr Cys Thr Lys Glu Ile Gly Tyr Tyr Gly Lys Arg Phe Pro Cys Ala
            580                 585                 590
Pro Gln Asp Val Lys Cys Gly Arg Leu Tyr Cys Leu Asp Asn Ser Phe
        595                 600                 605
Lys Lys Asn Met Arg Cys Lys Asn Asp Tyr Ser Tyr Ala Asp Glu Asn
    610                 615                 620
Lys Gly Ile Val Glu Pro Gly Thr Lys Cys Glu Asp Gly Lys Val Cys
625                 630                 635                 640
Ile Asn Arg Lys Cys Val Asp Val Asn Thr Ala Tyr His His His
            645                 650                 655
His His

<210> SEQ ID NO 19
<211> LENGTH: 1923
<212> TYPE: DNA
<213> ORGANISM: Artificial Sequence
<220> FEATURE:
<223> OTHER INFORMATION: Construct pTAP534, otpa
      leader-pro-GPR-Metalloprotease-Disintegrin-Cys rich-His tag

<400> SEQUENCE: 19
atggatgcaa tgaagagagg gctctgctgt gtgctgctgc tgtgtggcgc cgtcttcgtt      60
tcgctcagcc aggaaatcca tgccgagttg agacgcttcc gtagatcttg ctctataatc     120
ctgggatctg ggaatgttaa tgattatgaa gtagtgtatc cacaaaaagt cactgcattg     180
cccaaaggag cagttcagca gcctgagcaa agtatgaag atgccatgca atatgaattt     240
gaagtgaagg gagagccagt ggtccttcac ctagaaaaaa ataagaaact ttttcagaa      300
```

```
gattacagtg agactcatta ttcgtctgat gacagagaaa ttacaacaaa cccttcagtt    360
gaggatcact gctattatca tggacggatc cagaatgatg ctgagtcaac tgcaagcatc    420
agtgcatgca atggtttgaa aggacatttc aagcttcgag gggagacgta ctttattgaa    480
cccttgaaga ttcccgacag tgaagcccat gcagtctaca atatgaaaaa catagaaaat    540
gaggatgaag cccccaaaat gtgtggggta acccaggata attgggaatc agatgaaccc    600
atcaaaaaga ctttggggcc aagagttcct cctcatgaac gaaaatttga gaaaaaattc    660
attgagcttg tcgtagttgt ggaccacagt atggtcacaa atacaacaa tgattcaact    720 gctatccgca catggatcta tgaaatgctc aacactgtaa atgagatcta cttacctttc    780
aatattcgtg tagcactggt tggcctagaa ttttggtgca atggtgactt gattaacgtg    840
acatccacag cagatgatac tttgcactca tttggcgaat ggcgcgcatc agatttgctg    900
aatcgtaaac gccatgatca tgctcagtta ctcacgaacg tgacactgga tcattccact    960
cttggtatca cgttcgtata tggcatgtgc aaatcagatc gttctgtaga acttattctg   1020
gattacagca acataacttt taatatggca tatatcattg cccatgagat gggtcatagt   1080
ctgggcatgt tacatgacac aaaattctgt acttgtgggg ctaaaccatg cattatgttt   1140
ggcaaagaaa gcattccacc gcccaaagaa ttcagcagtt gtagttatga ccagtataac   1200
aagtatcttc ttaaatataa cccaaaatgc attcttgatc caccttttgcg taaagatatt   1260 gcttcacctg cagtttgtgg caatgaaatt tgggaggaag gtgaagaatg tgattgtggt   1320
tctcctgcag attgtcgcaa tccatgctgt gatgctgcaa catgtaaact gaaaccaggg   1380
gcagaatgtg gcaatggtga gtgttgtgac aagtgcaaga ttcgtaaagc aggcacagaa   1440
tgccggccag cacgcgatga ctgtgatgtc gctgaacact gcactggcca atctgctgag   1500
tgtccccgta atgagttcca acgcaatggt caaccatgcc ttaacaactc tggttattgc   1560
tacaatgggg attgccccat catgttaaac caatgtattg ctctctttag tccaagtgca   1620
actgtggctc aagattcatg ttttcagcgt aacttgcaag gcagttacta tggctactgc   1680
acaaaggaaa ttggttacta tggtaaacgc tttccatgtg caccacaaga tgtaaaatgt   1740
ggccgtttat actgcttaga taattcattc aaaaaaaata tgcgttgcaa gaacgactat   1800
tcatacgcgg atgaaaataa gggtatcgtt gaacctggta caaaatgtga agatggtaag   1860
gtctgcatca accgcaagtg tgttgatgtg aatacagcct accatcacca tcaccatcac   1920
taa                                                                 1923
```

<210> SEQ ID NO 20  
<211> LENGTH: 640  
<212> TYPE: PRT  
<213> ORGANISM: Artificial Sequence  
<220> FEATURE:  
<223> OTHER INFORMATION: Construct pTAP534, otpa  
    leader-pro-GPR-Metalloprotease-Disintegrin-Cys rich-His tag

<400> SEQUENCE: 20

```
Met Asp Ala Met Lys Arg Gly Leu Cys Cys Val Leu Leu Cys Gly
1               5                   10                  15

Ala Val Phe Val Ser Leu Ser Gln Glu Ile His Ala Glu Leu Arg Arg
            20                  25                  30

Phe Arg Arg Ser Cys Ser Ile Ile Leu Gly Ser Gly Asn Val Asn Asp
        35                  40                  45

Tyr Glu Val Val Tyr Pro Gln Lys Val Thr Ala Leu Pro Lys Gly Ala
    50                  55                  60
```

```
Val Gln Gln Pro Glu Gln Lys Tyr Glu Asp Ala Met Gln Tyr Glu Phe
65                  70                  75                  80

Glu Val Lys Gly Glu Pro Val Val Leu His Leu Glu Lys Asn Lys Glu
                85                  90                  95

Leu Phe Ser Glu Asp Tyr Ser Glu Thr His Tyr Ser Ser Asp Asp Arg
            100                 105                 110

Glu Ile Thr Thr Asn Pro Ser Val Glu Asp His Cys Tyr Tyr His Gly
        115                 120                 125

Arg Ile Gln Asn Asp Ala Glu Ser Thr Ala Ser Ile Ser Ala Cys Asn
    130                 135                 140

Gly Leu Lys Gly His Phe Lys Leu Arg Gly Glu Thr Tyr Phe Ile Glu
145                 150                 155                 160

Pro Leu Lys Ile Pro Asp Ser Glu Ala His Ala Val Tyr Lys Tyr Glu
                165                 170                 175

Asn Ile Glu Asn Glu Asp Glu Ala Pro Lys Met Cys Gly Val Thr Gln
            180                 185                 190

Asp Asn Trp Glu Ser Asp Glu Pro Ile Lys Lys Thr Leu Gly Pro Arg
        195                 200                 205

Val Pro Pro His Glu Arg Lys Phe Glu Lys Lys Phe Ile Glu Leu Val
210                 215                 220

Val Val Val Asp His Ser Met Val Thr Lys Tyr Asn Asn Asp Ser Thr
225                 230                 235                 240

Ala Ile Arg Thr Trp Ile Tyr Glu Met Leu Asn Thr Val Asn Glu Ile
                245                 250                 255

Tyr Leu Pro Phe Asn Ile Arg Val Ala Leu Val Gly Leu Glu Phe Trp
            260                 265                 270

Cys Asn Gly Asp Leu Ile Asn Val Thr Ser Thr Ala Asp Asp Thr Leu
        275                 280                 285

His Ser Phe Gly Glu Trp Arg Ala Ser Asp Leu Leu Asn Arg Lys Arg
    290                 295                 300

His Asp His Ala Gln Leu Leu Thr Asn Val Thr Leu Asp His Ser Thr
305                 310                 315                 320

Leu Gly Ile Thr Phe Val Tyr Gly Met Cys Lys Ser Asp Arg Ser Val
                325                 330                 335

Glu Leu Ile Leu Asp Tyr Ser Asn Ile Thr Phe Asn Met Ala Tyr Ile
            340                 345                 350

Ile Ala His Glu Met Gly His Ser Leu Gly Met Leu His Asp Thr Lys
        355                 360                 365

Phe Cys Thr Cys Gly Ala Lys Pro Cys Ile Met Phe Gly Lys Glu Ser
    370                 375                 380

Ile Pro Pro Pro Lys Glu Phe Ser Ser Cys Ser Tyr Asp Gln Tyr Asn
385                 390                 395                 400

Lys Tyr Leu Leu Lys Tyr Asn Pro Lys Cys Ile Leu Asp Pro Pro Leu
                405                 410                 415

Arg Lys Asp Ile Ala Ser Pro Ala Val Cys Gly Asn Glu Ile Trp Glu
            420                 425                 430

Glu Gly Glu Glu Cys Asp Cys Gly Ser Pro Ala Asp Cys Arg Asn Pro
        435                 440                 445

Cys Cys Asp Ala Ala Thr Cys Lys Leu Lys Pro Gly Ala Glu Cys Gly
    450                 455                 460

Asn Gly Glu Cys Cys Asp Lys Cys Lys Ile Arg Lys Ala Gly Thr Glu
465                 470                 475                 480
```

| | | | | | | | | | | |
|---|---|---|---|---|---|---|---|---|---|---|
|Cys|Arg|Pro|Ala|Arg|Asp|Asp|Cys|Asp|Val|Ala|Glu|His|Cys|Thr|Gly|
| | | | |485| | |490| | | |  | |495| | |

Cys Arg Pro Ala Arg Asp Asp Cys Asp Val Ala Glu His Cys Thr Gly
                485             490                 495

Gln Ser Ala Glu Cys Pro Arg Asn Glu Phe Gln Arg Asn Gly Gln Pro
            500             505                 510

Cys Leu Asn Asn Ser Gly Tyr Cys Tyr Asn Gly Asp Cys Pro Ile Met
            515             520                 525

Leu Asn Gln Cys Ile Ala Leu Phe Ser Pro Ser Ala Thr Val Ala Gln
        530                 535             540

Asp Ser Cys Phe Gln Arg Asn Leu Gln Gly Ser Tyr Tyr Gly Tyr Cys
545                 550                 555                 560

Thr Lys Glu Ile Gly Tyr Tyr Gly Lys Arg Phe Pro Cys Ala Pro Gln
                565                 570                 575

Asp Val Lys Cys Gly Arg Leu Tyr Cys Leu Asp Asn Ser Phe Lys Lys
            580                 585                 590

Asn Met Arg Cys Lys Asn Asp Tyr Ser Tyr Ala Asp Glu Asn Lys Gly
            595                 600                 605

Ile Val Glu Pro Gly Thr Lys Cys Glu Asp Gly Lys Val Cys Ile Asn
        610                 615                 620

Arg Lys Cys Val Asp Val Asn Thr Ala Tyr His His His His His His
625                 630                 635                 640

<210> SEQ ID NO 21
<211> LENGTH: 1887
<212> TYPE: DNA
<213> ORGANISM: Artificial Sequence
<220> FEATURE:
<223> OTHER INFORMATION: Construct pTAP542, truncated otpa
      leader-pro-GPR-Metalloprotease-Disintegrin-Cys rich-His tag

<400> SEQUENCE: 21

```
atggatgcaa tgaagagagg gctctgctgt gtgctgctgc tgtgtggcgc cgtcttcgtt      60
tcgctcagcc agtgctctat aatcctggga tctgggaatg ttaatgatta tgaagtagtg     120
tatccacaaa aagtcactgc attgcccaaa ggagcagttc agcagcctga gcaaaagtat     180
gaagatgcca tgcaatatga atttgaagtg aagggagagc cagtggtcct tcacctagaa     240
aaaaataaag aacttttttc agaagattac agtgagacta ttattcgtc tgatgacaga      300 gaaattacaa caaacccttc agttgaggat cactgctatt atcatggacg gatccagaat     360
gatgctgagt caactgcaag catcagtgca tgcaatggtt tgaaaggaca tttcaagctt     420 cgagggggaga cgtactttat tgaaccttg aagattcccg acagtgaagc ccatgcagtc     480
tacaaatatg aaaacataga aaatgaggat gaagccccca aatgtgtggg ggtaacccag     540
gataattggg aatcagatga acccatcaaa aagactttgg ggccaagagt tcctcctcat     600
gaacgaaaat tgagaaaaa attcattgag cttgtcgtag ttgtggacca cagtatggtc     660
acaaaataca caatgattc aactgctatc cgcacatgga tctatgaaat gctcaacact     720
gtaaatgaga tctacttacc tttcaatatt cgtgtagcac tggttggcct agaattttgg     780
tgcaatggtg acttgattaa cgtgacatcc acagcagatg atactttgca ctcatttggc     840
gaatggcgcg catcagattt gctgaatcgt aaacgccatg atcatgctca gttactcacg     900
aacgtgacac tggatcattc cactcttggt atcacgttcg tatatggcat gtgcaaatca     960
gatcgttctg tagaacttat tctggattac agcaacataa ctttaatat ggcatatatc      1020 attgcccatg agatgggtca tagtctgggc atgttacatg acacaaaatt ctgtacttgt     1080
ggggctaaac catgcattat gtttggcaaa gaaagcattc caccgcccaa agaattcagc     1140
```

```
agttgtagtt atgaccagta taacaagtat cttcttaaat ataacccaaa atgcattctt  1200
gatccacctt tgcgtaaaga tattgcttca cctgcagttt gtggcaatga aatttgggag  1260
gaaggtgaag aatgtgattg tggttctcct gcagattgtc gcaatccatg ctgtgatgct  1320
gcaacatgta aactgaaacc aggggcagaa tgtggcaatg tgagtgttg tgacaagtgc   1380 aagattcgta agcaggcac agaatgccgg ccagcacgcg atgactgtga tgtcgctgaa   1440
cactgcactg gccaatctgc tgagtgtccc cgtaatgagt ccaacgcaa tggtcaacca   1500 tgccttaaca actctggtta ttgctacaat ggggattgcc ccatcatgtt aaaccaatgt  1560
attgctctct ttagtccaag tgcaactgtg gctcaagatt catgttttca gcgtaacttg  1620
caaggcagtt actatggcta ctgcacaaag gaaattggtt actatggtaa acgctttcca  1680
tgtgcaccac aagatgtaaa atgtggccgt ttatactgct tagataattc attcaaaaaa  1740
aatatgcgtt gcaagaacga ctattcatac gcggatgaaa ataagggtat cgttgaacct  1800
ggtacaaaat gtgaagatgg taaggtctgc atcaaccgca agtgtgttga tgtgaataca  1860
gcctaccatc accatcacca tcactaa                                      1887
```

<210> SEQ ID NO 22
<211> LENGTH: 628
<212> TYPE: PRT
<213> ORGANISM: Artificial Sequence
<220> FEATURE:
<223> OTHER INFORMATION: Construct pTAP542, truncated otpa
      leader-pro-GPR-Metalloprotease-Disintegrin-Cys rich-His tag

<400> SEQUENCE: 22

```
Met Asp Ala Met Lys Arg Gly Leu Cys Cys Val Leu Leu Leu Cys Gly
1               5                  10                  15

Ala Val Phe Val Ser Leu Ser Gln Cys Ser Ile Ile Leu Gly Ser Gly
            20                  25                  30

Asn Val Asn Asp Tyr Glu Val Val Tyr Pro Gln Lys Val Thr Ala Leu
        35                  40                  45

Pro Lys Gly Ala Val Gln Gln Pro Glu Gln Lys Tyr Glu Asp Ala Met
    50                  55                  60

Gln Tyr Glu Phe Glu Val Lys Gly Glu Pro Val Val Leu His Leu Glu
65                  70                  75                  80

Lys Asn Lys Glu Leu Phe Ser Glu Asp Tyr Ser Glu Thr His Tyr Ser
                85                  90                  95

Ser Asp Asp Arg Glu Ile Thr Thr Asn Pro Ser Val Glu Asp His Cys
            100                 105                 110

Tyr Tyr His Gly Arg Ile Gln Asn Asp Ala Glu Ser Thr Ala Ser Ile
        115                 120                 125

Ser Ala Cys Asn Gly Leu Lys Gly His Phe Lys Leu Arg Gly Glu Thr
    130                 135                 140

Tyr Phe Ile Glu Pro Leu Lys Ile Pro Asp Ser Glu Ala His Ala Val
145                 150                 155                 160

Tyr Lys Tyr Glu Asn Ile Glu Asn Glu Asp Glu Ala Pro Lys Met Cys
                165                 170                 175

Gly Val Thr Gln Asp Asn Trp Glu Ser Asp Glu Pro Ile Lys Lys Thr
            180                 185                 190

Leu Gly Pro Arg Val Pro Pro His Glu Arg Lys Phe Glu Lys Lys Phe
        195                 200                 205

Ile Glu Leu Val Val Val Val Asp His Ser Met Val Thr Lys Tyr Asn
    210                 215                 220
```

Asn Asp Ser Thr Ala Ile Arg Thr Trp Ile Tyr Glu Met Leu Asn Thr
225                 230                 235                 240

Val Asn Glu Ile Tyr Leu Pro Phe Asn Ile Arg Val Ala Leu Val Gly
            245                 250                 255

Leu Glu Phe Trp Cys Asn Gly Asp Leu Ile Asn Val Thr Ser Thr Ala
                260                 265                 270

Asp Asp Thr Leu His Ser Phe Gly Glu Trp Arg Ala Ser Asp Leu Leu
        275                 280                 285

Asn Arg Lys Arg His Asp His Ala Gln Leu Leu Thr Asn Val Thr Leu
290                 295                 300

Asp His Ser Thr Leu Gly Ile Thr Phe Val Tyr Gly Met Cys Lys Ser
305                 310                 315                 320

Asp Arg Ser Val Glu Leu Ile Leu Asp Tyr Ser Asn Ile Thr Phe Asn
                325                 330                 335

Met Ala Tyr Ile Ile Ala His Glu Met Gly His Ser Leu Gly Met Leu
                340                 345                 350

His Asp Thr Lys Phe Cys Thr Cys Gly Ala Lys Pro Cys Ile Met Phe
        355                 360                 365

Gly Lys Glu Ser Ile Pro Pro Pro Lys Glu Phe Ser Ser Cys Ser Tyr
370                 375                 380

Asp Gln Tyr Asn Lys Tyr Leu Leu Lys Tyr Asn Pro Lys Cys Ile Leu
385                 390                 395                 400

Asp Pro Pro Leu Arg Lys Asp Ile Ala Ser Pro Ala Val Cys Gly Asn
                405                 410                 415

Glu Ile Trp Glu Glu Gly Glu Cys Asp Cys Gly Ser Pro Ala Asp
                420                 425                 430

Cys Arg Asn Pro Cys Cys Asp Ala Ala Thr Cys Lys Leu Lys Pro Gly
        435                 440                 445

Ala Glu Cys Gly Asn Gly Glu Cys Cys Asp Lys Cys Lys Ile Arg Lys
450                 455                 460

Ala Gly Thr Glu Cys Arg Pro Ala Arg Asp Asp Cys Asp Val Ala Glu
465                 470                 475                 480

His Cys Thr Gly Gln Ser Ala Glu Cys Pro Arg Asn Glu Phe Gln Arg
        485                 490                 495

Asn Gly Gln Pro Cys Leu Asn Asn Ser Gly Tyr Cys Tyr Asn Gly Asp
            500                 505                 510

Cys Pro Ile Met Leu Asn Gln Cys Ile Ala Leu Phe Ser Pro Ser Ala
        515                 520                 525

Thr Val Ala Gln Asp Ser Cys Phe Gln Arg Asn Leu Gln Gly Ser Tyr
530                 535                 540

Tyr Gly Tyr Cys Thr Lys Glu Ile Gly Tyr Tyr Gly Lys Arg Phe Pro
545                 550                 555                 560

Cys Ala Pro Gln Asp Val Lys Cys Gly Arg Leu Tyr Cys Leu Asp Asn
                565                 570                 575

Ser Phe Lys Lys Asn Met Arg Cys Lys Asn Asp Tyr Ser Tyr Ala Asp
            580                 585                 590

Glu Asn Lys Gly Ile Val Glu Pro Gly Thr Lys Cys Glu Asp Gly Lys
            595                 600                 605

Val Cys Ile Asn Arg Lys Cys Val Asp Val Asn Thr Ala Tyr His His
        610                 615                 620

His His His His
625

<210> SEQ ID NO 23
<211> LENGTH: 1869
<212> TYPE: DNA
<213> ORGANISM: Artificial Sequence
<220> FEATURE:
<223> OTHER INFORMATION: Construct MPET1697,
met-pre-pro-GPR-Metalloprotease-Disintegrin-Cys rich-His tag

<400> SEQUENCE: 23

```
atgatccaga ttctcttggt aattatatgc ttagcagttt ttccatatca aggttgctct      60
ataatcctgg gatctgggaa tgttaatgat tatgaagtag tgtatccaca aaaagtcact     120
gcattgccca aggagcagt tcagcagcct gagcaaaagt atgaagatgc catgcaatat     180
gaatttgaag tgaagggaga gccagtggtc cttcacctag aaaaaaataa agaactttt     240
tcagaagatt acagtgagac tcattattcg tctgatgaca gagaaattac aacaaaccct     300
tcagttgagg atcactgcta ttatcatgga cggatccaga atgatgctga gtcaactgca     360
agcatcagtg catgcaatgg tttgaaagga catttcaagc ttcgagggga gacgtacttt     420
attgaaccct tgaagattcc cgacagtgaa gcccatgcag tctacaaata tgaaaacata     480
gaaaatgagg atgaagcccc caaaatgtgt ggggtaaccc aggataattg gaatcagat     540
gaacccatca aaaagacttt ggggccaaga gttcctcctc atgaacgaaa atttgagaaa     600
aaattcattg agcttgtcgt agttgtggac acagtatgg tcacaaaata caacaatgat     660
tcaactgcta tccgcacatg gatctatgaa atgctcaaca ctgtaaatga gatctactta     720
cctttcaata ttcgtgtagc actggttggc ctagaatttt ggtgcaatgg tgacttgatt     780
aacgtgacat ccacagcaga tgatactttg cactcatttg gcgaatggcg cgcatcagat     840
ttgctgaatc gtaaacgcca tgatcatgct cagttactca cgaacgtgac actggatcat     900
tccactcttg gtatcacgtt cgtatatggc atgtgcaaat cagatcgttc tgtagaactt     960
attctggatt acagcaacat aacttttaat atggcatata tcattgccta ttccatgggt    1020
actagtctgg gcatgttaac tgacacaaaa ttctgtactt gtggggctaa ccatgcatt    1080
atgtttggca agaaaagcat tccaccgccc aaagaattca gcagttgtag ttatgaccag    1140
tataacaagt atcttcttaa atataaccca aaatgcattc ttgatccacc tttgcgtaaa    1200
gatattgctt cacctgcagt ttgtggcaat gaaatttggg aggaaggtga agaatgtgat    1260
tgtggttctc ctgcagattg tcgcaatcca tgctgtgatg ctgcaacatg taaactgaaa    1320
ccaggggcag aatgtggcaa tggtgagtgt tgtgacaagt gcagattcg taaagcaggc    1380
acagaatgcc ggccagcacg cgatgactgt gatgtcgctg aacactgcac tggccaatct    1440
gctgagtgtc cccgtaatga gttccaacgc aatggtcaac catgccttaa caactctggt    1500
tattgctaca tgggggattg ccccatcatg ttaaaccaat gtattgctct ctttagtcca    1560
agtgcaactg tggctcaaga ttcatgtttt cagcgtaact tgcaaggcag ttactatggc    1620
tactgcacaa aggaaattgg ttactatggt aaacgctttc catgtgcacc acaagatgta    1680
aaatgtggcc gtttatactg cttagataat tcattcaaaa aaatatgcg ttgcaagaac    1740
gactattcat acgcggatga aaataagggt atcgttgaac ctggtacaaa atgtgaagat    1800
ggtaaggtct gcatcaaccg caagtgtgtt gatgtgaata cagcctacca tcaccatcac    1860
catcactaa                                                            1869
```

<210> SEQ ID NO 24
<211> LENGTH: 622
<212> TYPE: PRT
<213> ORGANISM: Artificial Sequence

```
<220> FEATURE:
<223> OTHER INFORMATION: Construct MPET1697,
      met-pre-pro-GPR-Metalloprotease-Disintegrin-Cys rich-His tag

<400> SEQUENCE: 24

Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Asp Asp Arg Glu Ile
                    85                  90                  95

Thr Thr Asn Pro Ser Val Glu Asp His Cys Tyr Tyr His Gly Arg Ile
                100                 105                 110

Gln Asn Asp Ala Glu Ser Thr Ala Ser Ile Ser Ala Cys Asn Gly Leu
            115                 120                 125

Lys Gly His Phe Lys Leu Arg Gly Glu Thr Tyr Phe Ile Glu Pro Leu
        130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Pro Arg Val Pro
            180                 185                 190

Pro His Glu Arg Lys Phe Glu Lys Phe Ile Glu Leu Val Val Val
        195                 200                 205

Val Asp His Ser Met Val Thr Lys Tyr Asn Asn Asp Ser Thr Ala Ile
210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

Tyr Ser Met Gly Thr Ser Leu Gly Met Leu Thr Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
370                 375                 380

Leu Leu Lys Tyr Asn Pro Lys Cys Ile Leu Asp Pro Pro Leu Arg Lys
```

```
                385                 390                 395                 400
Asp Ile Ala Ser Pro Ala Val Cys Gly Asn Glu Ile Trp Glu Glu Gly
                    405                 410                 415

Glu Glu Cys Asp Cys Gly Ser Pro Ala Asp Cys Arg Asn Pro Cys Cys
                420                 425                 430

Asp Ala Ala Thr Cys Lys Leu Lys Pro Gly Ala Glu Cys Gly Asn Gly
                435                 440                 445

Glu Cys Cys Asp Lys Cys Lys Ile Arg Lys Ala Gly Thr Glu Cys Arg
            450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro Cys Leu
                485                 490                 495

Asn Asn Ser Gly Tyr Cys Tyr Asn Gly Asp Cys Pro Ile Met Leu Asn
                500                 505                 510

Gln Cys Ile Ala Leu Phe Ser Pro Ser Ala Thr Val Ala Gln Asp Ser
            515                 520                 525

Cys Phe Gln Arg Asn Leu Gln Gly Ser Tyr Tyr Gly Tyr Cys Thr Lys
        530                 535                 540

Glu Ile Gly Tyr Tyr Gly Lys Arg Phe Pro Cys Ala Pro Gln Asp Val
545                 550                 555                 560

Lys Cys Gly Arg Leu Tyr Cys Leu Asp Asn Ser Phe Lys Lys Asn Met
                565                 570                 575

Arg Cys Lys Asn Asp Tyr Ser Tyr Ala Asp Glu Asn Lys Gly Ile Val
                580                 585                 590

Glu Pro Gly Thr Lys Cys Glu Asp Gly Lys Val Cys Ile Asn Arg Lys
            595                 600                 605

Cys Val Asp Val Asn Thr Ala Tyr His His His His His His
        610                 615                 620

<210> SEQ ID NO 25
<211> LENGTH: 1498
<212> TYPE: DNA
<213> ORGANISM: Artificial Sequence
<220> FEATURE:
<223> OTHER INFORMATION: Construct pTAP549,
      met-pre-pro-GPR-Metalloprotease-Disintegrin-His tag

<400> SEQUENCE: 25
atgatccaga ttctcttggt aattatatgc ttagcagttt ttccatatca aggttgctct       60
ataatcctgg gatctgggaa tgttaatgat tatgaagtag tgtatccaca aaaagtcact      120
gcattgccca aggagcagtc tcagcagcct gagcaaaagt atgaagatgc catgcaatat      180
gaatttgaag tgaagggaga gccagtggtc cttcacctag aaaaaaataa gaactttttt      240
tcagaagatt acagtgagac tcattattcg tctgatgaca gagaaattac aacaaaccct      300
tcagttgagc tcactgcta ttatcatgga cggatccaga atgatgctga gtcaactgca      360
agcatcagtg catgcaatgg tttgaaagga catttcaagc ttcgagggga gacgtacttt      420
attgaaccct tgaagattcc cgacagtgaa gcccatgcag tctacaaata tgaaaacata      480
gaaaatgagg atgaagcccc caaaatgtgt ggggtaaccc aggataattg gaatcagat      540 gaacccatca aaaagacttt ggggccaaga gttcctcctc atgaacgaaa atttgagaaa      600
aaattcattg agcttgtcgt agttgtggac cacagtatgg tcacaaaata caacaatgat      660
tcaactgcta tccgcacatg gatctatgaa atgctcaaca ctgtaaatga gatctactta      720
```

```
cctttcaata ttcgtgtagc actggttggc ctagaatttt ggtgcaatgg tgacttgatt    780
aacgtgacat ccacagcaga tgatactttg cactcatttg gcgaatggcg cgcatcagat    840
ttgctgaatc gtaaacgcca tgatcatgct cagttactca cgaacgtgac actggatcat    900
tccactcttg gtatcacgtt cgtatatggc atgtgcaaat cagatcgttc tgtagaactt    960
attctggatt acagcaacat aacttttaat atggcatata tcattgccca tgagatgggt   1020
catagtctgg gcatgttaca tgacacaaaa ttctgtactt gtggggctaa ccatgcatt    1080
atgtttggca agaaagcat ccaccgccc aaagaattca gcagttgtag ttatgaccag    1140
tataacaagt atcttcttaa atataaccca aaatgcattc ttgatccacc tttgcgtaaa   1200
gatattgctt cacctgcagt ttgtggcaat gaaatttggg aggaaggtga agaatgtgat   1260
tgtggttctc ctgcagattg tcgcaatcca tgctgtgatg ctgcaacatg taaactgaaa   1320
ccaggggcag aatgtggcaa tggtgagtgt tgtgacaagt gcaagattcg taaagcaggc   1380
acagaatgcc ggccagcacg cgatgactgt gatgtcgctg aacactgcac tggccaatct   1440
gctgagtgtc cccgtaatga gttccaacgc aatggtccat caccatcacc atcactaa    1498
```

<210> SEQ ID NO 26
<211> LENGTH: 500
<212> TYPE: PRT
<213> ORGANISM: Artificial Sequence
<220> FEATURE:
<223> OTHER INFORMATION: Construct pTAP549,
    met-pre-pro-GPR-Metalloprotease-Disintegrin-His tag

<400> SEQUENCE: 26

Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Arg Glu Ile
                85                  90                  95

Thr Thr Asn Pro Ser Val Glu Asp His Cys Tyr Tyr His Gly Arg Ile
            100                 105                 110

Gln Asn Asp Ala Glu Ser Thr Ala Ser Ile Ser Ala Cys Asn Gly Leu
        115                 120                 125

Lys Gly His Phe Lys Leu Arg Gly Glu Thr Tyr Phe Ile Glu Pro Leu
    130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Pro Arg Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
    210                 215                 220

```
Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
    290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
    370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
                405                 410                 415

Glu Glu Cys Asp Cys Gly Ser Pro Ala Asp Cys Arg Asn Pro Cys Cys
            420                 425                 430

Asp Ala Ala Thr Cys Lys Leu Lys Pro Gly Ala Glu Cys Gly Asn Gly
        435                 440                 445

Glu Cys Cys Asp Lys Cys Lys Ile Arg Lys Ala Gly Thr Glu Cys Arg
    450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro His His
                485                 490                 495

His His His His
        500

<210> SEQ ID NO 27
<211> LENGTH: 1233
<212> TYPE: DNA
<213> ORGANISM: Artificial Sequence
<220> FEATURE:
<223> OTHER INFORMATION: Construct pTAP547, met-pre-pro-GPR-
      Metalloprotease-Cys rich-His tag

<400> SEQUENCE: 27
atgatccaga ttctcttggt aattatatgc ttagcagttt ttccatatca aggttgctct      60
ataatcctgg gatctgggaa tgttaatgat tatgaagtag tgtatccaca aaaagtcact     120
gcattgccca aggagcagt tcagcagcct gagcaaaagt atgaagatgc catgcaatat     180
gaatttgaag tgaagggaga gccagtggtc cttcacctag aaaaaaataa agaacttttt     240
tcagaagatt acagtgagac tcattattcg tctgatgaca gagaaattac aacaaaccct     300
tcagttgagg atcactgcta ttatcatgga cggatccaga tgatgctga gtcaactgca     360 agcatcagtg catgcaatgg tttgaaagga catttcaagc ttcgagggga gacgtacttt     420
```

```
attgaaccct tgaagattcc cgacagtgaa gcccatgcag tctacaaata tgaaaacata    480
gaaaatgagg atgaagcccc caaaatgtgt ggggtaaccc aggataattg ggaatcagat    540
gaacccatca aaaagacttt ggggccaaga gttcctcctc atgaacgaaa atttgagaaa    600
aaattcattg agcttgtcgt agttgtggac cacagtatgg tcacaaaata caacaatgat    660
tcaactgcta tccgcacatg gatctatgaa atgctcaaca ctgtaaatga gatctactta    720
cctttcaata ttcgtgtagc actggttggc ctagaatttt ggtgcaatgg tgacttgatt    780
aacgtgacat ccacagcaga tgatactttg cactcatttg gcgaatggcg cgcatcagat    840
ttgctgaatc gtaaacgcca tgatcatgct cagttactca cgaacgtgac actggatcat    900
tccactcttg gtatcacgtt cgtatatggc atgtgcaaat cagatcgttc tgtagaactt    960
attctggatt acagcaacat aactttaat atggcatata tcattgccca tgagatgggt    1020
catagtctgg gcatgttaca tgacacaaaa ttctgtactt gtggggctaa accatgcatt    1080
atgtttggca agaaaagcat tccaccgccc aaagaattca gcagttgtag ttatgaccag    1140
tataacaagt atcttcttaa atataaccca aaatgcattc ttgatccacc tttgcgtaaa    1200
gatattgctt cacatcacca tcaccatcac taa                                 1233
```

<210> SEQ ID NO 28
<211> LENGTH: 410
<212> TYPE: PRT
<213> ORGANISM: Artificial Sequence
<220> FEATURE:
<223> OTHER INFORMATION: Construct pTAP547, met-pre-pro-GPR-
     Metalloprotease-Cys rich-His tag

<400> SEQUENCE: 28

```
Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
                20                  25                  30

Val Val Tyr Pro Gln Lys Val Thr Ala Leu Pro Lys Gly Ala Val Gln
            35                  40                  45

Gln Pro Glu Gln Lys Tyr Glu Asp Ala Met Gln Tyr Glu Phe Glu Val
        50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Asp Asp Arg Glu Ile
                85                  90                  95

Thr Thr Asn Pro Ser Val Glu Asp His Cys Tyr Tyr His Gly Arg Ile
            100                 105                 110

Gln Asn Asp Ala Glu Ser Thr Ala Ser Ile Ser Ala Cys Asn Gly Leu
        115                 120                 125

Lys Gly His Phe Lys Leu Arg Gly Glu Thr Tyr Phe Ile Glu Pro Leu
    130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Pro Arg Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
```

```
                210                 215                 220
Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
                260                 265                 270

Phe Gly Glu Trp Arg Ala Ser Asp Leu Leu Asn Arg Lys Arg His Asp
            275                 280                 285

His Ala Gln Leu Leu Thr Asn Val Thr Leu Asp His Ser Thr Leu Gly
        290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
370                 375                 380

Leu Leu Lys Tyr Asn Pro Lys Cys Ile Leu Asp Pro Pro Leu Arg Lys
385                 390                 395                 400

Asp Ile Ala Ser His His His His His His
                405                 410
```

<210> SEQ ID NO 29
<211> LENGTH: 901
<212> TYPE: DNA
<213> ORGANISM: Artificial Sequence
<220> FEATURE:
<223> OTHER INFORMATION: construct pTAP493, alpha Fpp leader-
      Metalloprotease-His tag

<400> SEQUENCE: 29

```
atgagatttc cttctatttt tactgctgtt ttattcgctg cttcctccgc tttagctgct      60
ccagtcaaca ctaccactga agatgaaacg gctcaaattc cagctgaagc tgtcatcggt     120
tactctgatt tagaaggtga tttcgatgtt gctgttttgc catttccaa ctccaccaat      180 aacggtttat tgtttatcaa tactactatt gctagcattg ctgctaaaga agaaggtgta     240
agcttggaca agagagttcc tcctcatgaa cgaaaatttg agaaaaaatt cattgagctt     300
gtcgtagttg tggaccacag tatggtcaca aaatacaaca atgattcaac tgctatccgc     360
acatggatct atgaaatgct caacactgta aatgagatct acttaccttt caatattcgt     420
gtagcactgg ttggcctaga attttggtgc aatggtgact tgattaacgt gacatccaca     480
gcagatgata ctttgcactc atttggcgaa tggcgcgcat cagatttgct gaatcgtaaa     540
cgccatgatc atgctcagtt actcacgaac gtgacactgg atcattccac tcttggtatc     600
acgttcgtat atggcatgtg caaatcagat cgttctgtag aacttattct ggattacagc     660
aacataactt ttaatatggc atatatcatt gcccatgaga tgggtcatag tctgggcatg     720
ttacatgaca caaaattctg tacttgtggg gctaaaccat gcattatgtt tggcaaagaa     780
agcattccac cgcccaaaga attcagcagt tgtagttatg accagtataa caagtatctt     840
cttaaatata acccaaaatg cattcttgat ccacctcatc accatcacca tcactagaat     900
``` t                                                                                    901

<210> SEQ ID NO 30
<211> LENGTH: 298
<212> TYPE: PRT
<213> ORGANISM: Artificial Sequence
<220> FEATURE:
<223> OTHER INFORMATION: construct pTAP493, alpha Fpp leader-
      Metalloprotease-His tag

<400> SEQUENCE: 30

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Val Pro Pro His Glu Arg Lys Phe Glu Lys Lys
                85                  90                  95

Phe Ile Glu Leu Val Val Val Asp His Ser Met Val Thr Lys Tyr
            100                 105                 110

Asn Asn Asp Ser Thr Ala Ile Arg Thr Trp Ile Tyr Glu Met Leu Asn
            115                 120                 125

Thr Val Asn Glu Ile Tyr Leu Pro Phe Asn Ile Arg Val Ala Leu Val
    130                 135                 140

Gly Leu Glu Phe Trp Cys Asn Gly Asp Leu Ile Asn Val Thr Ser Thr
145                 150                 155                 160

Ala Asp Asp Thr Leu His Ser Phe Gly Glu Trp Arg Ala Ser Asp Leu
                165                 170                 175

Leu Asn Arg Lys Arg His Asp His Ala Gln Leu Leu Thr Asn Val Thr
            180                 185                 190

Leu Asp His Ser Thr Leu Gly Ile Thr Phe Val Tyr Gly Met Cys Lys
        195                 200                 205

Ser Asp Arg Ser Val Glu Leu Ile Leu Asp Tyr Ser Asn Ile Thr Phe
    210                 215                 220

Asn Met Ala Tyr Ile Ile Ala His Glu Met Gly His Ser Leu Gly Met
225                 230                 235                 240

Leu His Asp Thr Lys Phe Cys Thr Cys Gly Ala Lys Pro Cys Ile Met
                245                 250                 255

Phe Gly Lys Glu Ser Ile Pro Pro Lys Glu Phe Ser Ser Cys Ser
            260                 265                 270

Tyr Asp Gln Tyr Asn Lys Tyr Leu Leu Lys Tyr Asn Pro Lys Cys Ile
        275                 280                 285

Leu Asp Pro Pro His His His His His His
        290                 295

<210> SEQ ID NO 31
<211> LENGTH: 1558
<212> TYPE: DNA
<213> ORGANISM: Artificial Sequence
<220> FEATURE:
<223> OTHER INFORMATION: Construct pTAP496, alpha Fpp
      leader-Metalloprotease-Disintegrin-Cys rich-His tag

<400> SEQUENCE: 31

```
atgagatttc cttctatttt tactgctgtt ttattcgctg cttcctccgc tttagctgct      60
ccagtcaaca ctaccactga agatgaaacg gctcaaattc agctgaagc tgtcatcggt     120
tactctgatt tagaaggtga tttcgatgtt gctgttttgc catttccaa ctccaccaat     180
aacggtttat tgtttatcaa tactactatt gctagcattg ctgctaaaga agaaggtgta    240
agcttggaca agagagttcc tcctcatgaa cgaaaatttg agaaaaatt cattgagctt    300
gtcgtagttg tggaccacag tatggtcaca aaatacaaca atgattcaac tgctatccgc    360
acatggatct atgaaatgct caacactgta aatgagatct acttacccttt caatattcgt    420
gtagcactgg ttggcctaga attttggtgc aatggtgact tgattaacgt gacatccaca    480
gcagatgata ctttgcactc atttggcgaa tggcgcgcat cagatttgct gaatcgtaaa    540
cgccatgatc atgctcagtt actcacgaac gtgacactgg atcattccac tcttggtatc    600
acgttcgtat atggcatgtg caaatcagat cgttctgtag aacttattct ggattacagc    660
aacataactt ttaatatggc atatatcatt gcccatgaga tgggtcatag tctgggcatg    720
ttacatgaca caaaattctg tacttgtggg gctaaaccat gcattatgtt tggcaaagaa    780
agcattccac cgcccaaaga attcagcagt tgtagttatg accagtataa caagtatctt    840
cttaaatata acccaaaatg cattcttgat ccacctttgc gtaaagatat tgcttcacct    900
gcagtttgtg gcaatgaaat ttgggaggaa ggtgaagaat gtgattgtgg ttctcctgca    960
gattgtcgca atccatgctg tgatgctgca acatgtaaac tgaaaccagg ggcagaatgt   1020
ggcaatggtg agtgttgtga caagtgcaag attcgtaaag caggcacaga atgccggcca   1080
gcacgcgatg actgtgatgt cgctgaacac tgcactggcc aatctgctga gtgtccccgt   1140
aatgagttcc aacgcaatgg tcaaccatgc cttaacaact ctggttattg ctacaatggg   1200
gattgcccca tcatgttaaa ccaatgtatt gctctcttta gtccaagtgc aactgtggct   1260
caagattcat gttttcagcg taacttgcaa ggcagttact atggctactg cacaaaggaa   1320
attggttact atggtaaacg cttttccatgt gcaccacaag atgtaaaatg tggccgttta   1380
tactgcttag ataattcatt caaaaaaaat atgcgttgca agaacgacta ttcatacgcg   1440
gatgaaaata agggtatcgt tgaacctggt acaaaatgtg aagatggtaa ggtctgcatc   1500
aaccgcaagt gtgttgatgt gaatacagcc taccatcacc atcaccatca ctagaatt      1558
```

<210> SEQ ID NO 32
<211> LENGTH: 517
<212> TYPE: PRT
<213> ORGANISM: Artificial Sequence
<220> FEATURE:
<223> OTHER INFORMATION: Construct pTAP496, alpha Fpp
    leader-Metalloprotease-Disintegrin-Cys rich-His tag

<400> SEQUENCE: 32

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80
```

```
Ser Leu Asp Lys Arg Val Pro Pro His Glu Arg Lys Phe Glu Lys Lys
                 85                  90                  95

Phe Ile Glu Leu Val Val Val Asp His Ser Met Val Thr Lys Tyr
            100                 105                 110

Asn Asn Asp Ser Thr Ala Ile Arg Thr Trp Ile Tyr Glu Met Leu Asn
            115                 120                 125

Thr Val Asn Glu Ile Tyr Leu Pro Phe Asn Ile Arg Val Ala Leu Val
        130                 135                 140

Gly Leu Glu Phe Trp Cys Asn Gly Asp Leu Ile Asn Val Thr Ser Thr
145                 150                 155                 160

Ala Asp Asp Thr Leu His Ser Phe Gly Glu Trp Arg Ala Ser Asp Leu
                165                 170                 175

Leu Asn Arg Lys Arg His Asp His Ala Gln Leu Leu Thr Asn Val Thr
                180                 185                 190

Leu Asp His Ser Thr Leu Gly Ile Thr Phe Val Tyr Gly Met Cys Lys
            195                 200                 205

Ser Asp Arg Ser Val Glu Leu Ile Leu Asp Tyr Ser Asn Ile Thr Phe
        210                 215                 220

Asn Met Ala Tyr Ile Ile Ala His Glu Met Gly His Ser Leu Gly Met
225                 230                 235                 240

Leu His Asp Thr Lys Phe Cys Thr Cys Gly Ala Lys Pro Cys Ile Met
                245                 250                 255

Phe Gly Lys Glu Ser Ile Pro Pro Lys Glu Phe Ser Ser Cys Ser
                260                 265                 270

Tyr Asp Gln Tyr Asn Lys Tyr Leu Leu Lys Tyr Asn Pro Lys Cys Ile
        275                 280                 285

Leu Asp Pro Pro Leu Arg Lys Asp Ile Ala Ser Pro Ala Val Cys Gly
        290                 295                 300

Asn Glu Ile Trp Glu Glu Gly Glu Glu Cys Asp Cys Gly Ser Pro Ala
305                 310                 315                 320

Asp Cys Arg Asn Pro Cys Cys Asp Ala Ala Thr Cys Lys Leu Lys Pro
                325                 330                 335

Gly Ala Glu Cys Gly Asn Gly Glu Cys Cys Asp Lys Cys Lys Ile Arg
            340                 345                 350

Lys Ala Gly Thr Glu Cys Arg Pro Ala Arg Asp Asp Cys Asp Val Ala
        355                 360                 365

Glu His Cys Thr Gly Gln Ser Ala Glu Cys Pro Arg Asn Glu Phe Gln
        370                 375                 380

Arg Asn Gly Gln Pro Cys Leu Asn Asn Ser Gly Tyr Cys Tyr Asn Gly
385                 390                 395                 400

Asp Cys Pro Ile Met Leu Asn Gln Cys Ile Ala Leu Phe Ser Pro Ser
                405                 410                 415

Ala Thr Val Ala Gln Asp Ser Cys Phe Gln Arg Asn Leu Gln Gly Ser
                420                 425                 430

Tyr Tyr Gly Tyr Cys Thr Lys Glu Ile Gly Tyr Tyr Gly Lys Arg Phe
            435                 440                 445

Pro Cys Ala Pro Gln Asp Val Lys Cys Gly Arg Leu Tyr Cys Leu Asp
        450                 455                 460

Asn Ser Phe Lys Lys Asn Met Arg Cys Lys Asn Asp Tyr Ser Tyr Ala
465                 470                 475                 480

Asp Glu Asn Lys Gly Ile Val Glu Pro Gly Thr Lys Cys Glu Asp Gly
                485                 490                 495
```

Lys Val Cys Ile Asn Arg Lys Cys Val Asp Val Asn Thr Ala Tyr His
                500                 505                 510

His His His His His
        515

<210> SEQ ID NO 33
<211> LENGTH: 1950
<212> TYPE: DNA
<213> ORGANISM: Artificial Sequence
<220> FEATURE:
<223> OTHER INFORMATION: Construct pTAP523/530, beta gluconase
      leader-pre-pro-GPR-Metalloprotease-Disintegrin-Cys rich-His tag

<400> SEQUENCE: 33

```
atgaagttct cgctaagtac attgacagtt atcaccacct tactatcatt ggtctcagct    60
gcaccactca ctttgaaaaa gagaatccag attctcttgg taattatatg cttagcagtt   120
tttccatatc aaggttgctc tataatcctg ggatctggga atgttaatga ttatgaagta   180
gtgtatccac aaaaagtcac tgcattgccc aaaggagcag ttcagcagcc tgagcaaaag   240
tatgaagatg ccatgcaata tgaatttgaa gtgaagggag agccagtggt ccttcaccta   300
gaaaaaaata agaacttttt tcagaagat tacagtgaga ctcattattc gtctgatgac   360
agagaaatta caacaaaccc ttcagttgag gatcactgct attatcatgg acggatccag   420
aatgatgctg agtcaactgc aagcatcagt gcatgcaatg gtttgaaagg acatttcaag   480
cttcgagggg agacgtactt tattgaaccc ttgaagattc ccgacagtga agcccatgca   540
gtctacaaat atgaaaacat agaaaatgag gatgaagccc caaaatgtg tggggtaacc   600
caggataatt gggaatcaga tgaacccatc aaaaagactt tggggccaag agttcctcct   660
catgaacgaa aatttgagaa aaattcatt gagcttgtcg tagttgtgga ccacagtatg   720
gtcacaaaat acaacaatga ttcaactgct atccgcacat ggatctatga aatgctcaac   780
actgtaaatg agatctactt accttttcaat attcgtgtag cactggttgg cctagaattt   840
tggtgcaatg gtgacttgat taacgtgaca tccacagcag atgatacttt gcactcattt   900
ggcgaatggc gcgcatcaga tttgctgaat cgtaaacgcc atgatcatgc tcagttactc   960
acgaacgtga cactggatca ttccactctt ggtatcacgt tcgtatatgg catgtgcaaa  1020
tcagatcgtt ctgtagaact tattctggat tacagcaaca taactttta tatggcatat  1080
atcattgccc atgagatggg tcatagtctg ggcatgttac atgacacaaa attctgtact  1140
tgtggggcta accatgcat atgtttggc aaagaaagca ttccaccgcc caagaattc  1200
agcagttgta gttatgacca gtataacaag tatcttctta aatataaccc aaaatgcatt  1260
cttgatccac ctttgcgtaa agatattgct tcacctgcag tttgtggcaa tgaaatttgg  1320
gaggaaggtg aagaatgtga ttgtggttct cctgcagatt gtcgcaatcc atgctgtgat  1380
gctgcaacat gtaaactgaa accaggggca gaatgtggca atggtgagtg ttgtgacaag  1440
tgcaagattc gtaaagcagg cacagaatgc cggccagcac gcgatgactg tgatgtcgct  1500
gaacactgca ctggccaatc tgctgagtgt ccccgtaatg agttccaacg caatggtcaa  1560
ccatgcctta caactctgg ttattgctac aatggggatt gccccatcat gttaaaccaa  1620
tgtattgctc tctttagtcc aagtgcaact gtggctcaag attcatgttt tcagcgtaac  1680
ttgcaaggca gttactatgg ctactgcaca aaggaaattg ttactatgg taaacgcttt  1740
ccatgtgcac cacaagatgt aaaatgtggc cgtttatact gcttagataa ttcattcaaa  1800
aaaaatatgc gttgcaagaa cgactattca tacgcggatg aaaataaggg tatcgttgaa  1860
```

-continued

```
cctggtacaa aatgtgaaga tggtaaggtc tgcatcaacc gcaagtgtgt tgatgtgaat    1920
acagcctacc atcaccatca ccatcactag                                     1950
```

<210> SEQ ID NO 34
<211> LENGTH: 649
<212> TYPE: PRT
<213> ORGANISM: Artificial Sequence
<220> FEATURE:
<223> OTHER INFORMATION: Construct pTAP523/530, beta gluconase
      leader-pre-pro-GPR-Metalloprotease-Disintegrin-Cys rich-His tag

<400> SEQUENCE: 34

```
Met Lys Phe Ser Leu Ser Thr Leu Thr Val Ile Thr Thr Leu Leu Ser
1               5                   10                  15

Leu Val Ser Ala Ala Pro Leu Thr Leu Lys Lys Arg Ile Gln Ile Leu
            20                  25                  30

Leu Val Ile Ile Cys Leu Ala Val Phe Pro Tyr Gln Gly Cys Ser Ile
        35                  40                  45

Ile Leu Gly Ser Gly Asn Val Asn Asp Tyr Glu Val Val Tyr Pro Gln
    50                  55                  60

Lys Val Thr Ala Leu Pro Lys Gly Ala Val Gln Gln Pro Glu Gln Lys
65                  70                  75                  80

Tyr Glu Asp Ala Met Gln Tyr Glu Phe Glu Val Lys Gly Glu Pro Val
                85                  90                  95

Val Leu His Leu Glu Lys Asn Lys Glu Leu Phe Ser Glu Asp Tyr Ser
            100                 105                 110

Glu Thr His Tyr Ser Ser Asp Asp Arg Glu Ile Thr Thr Asn Pro Ser
        115                 120                 125

Val Glu Asp His Cys Tyr Tyr His Gly Arg Ile Gln Asn Asp Ala Glu
    130                 135                 140

Ser Thr Ala Ser Ile Ser Ala Cys Asn Gly Leu Lys Gly His Phe Lys
145                 150                 155                 160

Leu Arg Gly Glu Thr Tyr Phe Ile Glu Pro Leu Lys Ile Pro Asp Ser
                165                 170                 175

Glu Ala His Ala Val Tyr Lys Tyr Glu Asn Ile Glu Asn Glu Asp Glu
            180                 185                 190

Ala Pro Lys Met Cys Gly Val Thr Gln Asp Asn Trp Glu Ser Asp Glu
        195                 200                 205

Pro Ile Lys Lys Thr Leu Gly Pro Arg Val Pro Pro His Glu Arg Lys
    210                 215                 220

Phe Glu Lys Lys Phe Ile Glu Leu Val Val Val Asp His Ser Met
225                 230                 235                 240

Val Thr Lys Tyr Asn Asn Asp Ser Thr Ala Ile Arg Thr Trp Ile Tyr
                245                 250                 255

Glu Met Leu Asn Thr Val Asn Glu Ile Tyr Leu Pro Phe Asn Ile Arg
            260                 265                 270

Val Ala Leu Val Gly Leu Glu Phe Trp Cys Asn Gly Asp Leu Ile Asn
        275                 280                 285

Val Thr Ser Thr Ala Asp Asp Thr Leu His Ser Phe Gly Glu Trp Arg
    290                 295                 300

Ala Ser Asp Leu Leu Asn Arg Lys Arg His Asp His Ala Gln Leu Leu
305                 310                 315                 320

Thr Asn Val Thr Leu Asp His Ser Thr Leu Gly Ile Thr Phe Val Tyr
                325                 330                 335

Gly Met Cys Lys Ser Asp Arg Ser Val Glu Leu Ile Leu Asp Tyr Ser
```

```
                340             345             350
Asn Ile Thr Phe Asn Met Ala Tyr Ile Ile Ala His Glu Met Gly His
                355             360             365
Ser Leu Gly Met Leu His Asp Thr Lys Phe Cys Thr Cys Gly Ala Lys
        370             375             380
Pro Cys Ile Met Phe Gly Lys Glu Ser Ile Pro Pro Lys Glu Phe
385             390             395             400
Ser Ser Cys Ser Tyr Asp Gln Tyr Asn Lys Tyr Leu Leu Lys Tyr Asn
                405             410             415
Pro Lys Cys Ile Leu Asp Pro Pro Leu Arg Lys Asp Ile Ala Ser Pro
                420             425             430
Ala Val Cys Gly Asn Glu Ile Trp Glu Glu Gly Glu Glu Cys Asp Cys
                435             440             445
Gly Ser Pro Ala Asp Cys Arg Asn Pro Cys Cys Asp Ala Ala Thr Cys
        450             455             460
Lys Leu Lys Pro Gly Ala Glu Cys Gly Asn Gly Glu Cys Cys Asp Lys
465             470             475             480
Cys Lys Ile Arg Lys Ala Gly Thr Glu Cys Arg Pro Ala Arg Asp Asp
                485             490             495
Cys Asp Val Ala Glu His Cys Thr Gly Gln Ser Ala Glu Cys Pro Arg
                500             505             510
Asn Glu Phe Gln Arg Asn Gly Gln Pro Cys Leu Asn Asn Ser Gly Tyr
                515             520             525
Cys Tyr Asn Gly Asp Cys Pro Ile Met Leu Asn Gln Cys Ile Ala Leu
                530             535             540
Phe Ser Pro Ser Ala Thr Val Ala Gln Asp Ser Cys Phe Gln Arg Asn
545             550             555             560
Leu Gln Gly Ser Tyr Tyr Gly Tyr Cys Thr Lys Glu Ile Gly Tyr Tyr
                565             570             575
Gly Lys Arg Phe Pro Cys Ala Pro Gln Asp Val Lys Cys Gly Arg Leu
                580             585             590
Tyr Cys Leu Asp Asn Ser Phe Lys Lys Asn Met Arg Cys Lys Asn Asp
                595             600             605
Tyr Ser Tyr Ala Asp Glu Asn Lys Gly Ile Val Glu Pro Gly Thr Lys
                610             615             620
Cys Glu Asp Gly Lys Val Cys Ile Asn Arg Lys Cys Val Asp Val Asn
625             630             635             640
Thr Ala Tyr His His His His His
                645
```

<210> SEQ ID NO 35
<211> LENGTH: 2205
<212> TYPE: DNA
<213> ORGANISM: Artificial Sequence
<220> FEATURE:
<223> OTHER INFORMATION: Construct pTAP525, alpha Fpp
      leader-pre-pro-GPR-Metalloprotease-Disintegrin-Cys rich-His tag

<400> SEQUENCE: 35

```
atgagatttc cttctatttt tactgctgtt ttattcgctg cttcctccgc tttagctgct    60
ccagtcaaca ctaccactga agatgaaacg gctcaaattc cagctgaagc tgtcatcggt   120
tactctgatt tagaaggtga tttcgatgtt gctgttttgc cattttccaa ctccaccaat   180
aacggtttat gtttatcaa tactactatt gctagcattg ctgctaaaga agaaggtgta    240
agcttggaca agagaatgaa gttctcgcta agtacattga cagttatcac caccttacta   300
```

```
tcattggtct cagctgcacc actcactttg aaaaagagaa tccagattct cttggtaatt    360
atatgcttag cagtttttcc atatcaaggt tgctctataa tcctgggatc tgggaatgtt    420
aatgattatg aagtagtgta tccacaaaaa gtcactgcat tgcccaaagg agcagttcag    480
cagcctgagc aaaagtatga agatgccatg caatatgaat ttgaagtgaa gggagagcca    540
gtggtccttc acctagaaaa aaataaagaa cttttttcag aagattacag tgagactcat    600
tattcgtctg atgacagaga aattacaaca aacccttcag ttgaggatca ctgctattat    660
catggacgga tccagaatga tgctgagtca actgcaagca tcagtgcatg caatggtttg    720
aaaggacatt tcaagcttcg aggggagacg tactttattg aacccttgaa gattcccgac    780
agtgaagccc atgcagtcta caaatatgaa acatagaaa atgaggatga agcccccaaa    840
atgtgtgggg taacccagga taattgggaa tcagatgaac ccatcaaaaa gactttgggg    900
ccaagagttc ctcctcatga acgaaaattt gagaaaaaat tcattgagct tgtcgtagtt    960
gtggaccaca gtatggtcac aaaatacaac aatgattcaa ctgctatccg cacatggatc   1020
tatgaaatgc tcaacactgt aaatgagatc tacttacctt tcaatattcg tgtagcactg   1080
gttggcctag aattttggtg caatggtgac ttgattaacg tgacatccac agcagatgat   1140
actttgcact catttggcga atggcgcgca tcagatttgc tgaatcgtaa acgccatgat   1200
catgctcagt tactcacgaa cgtgacactg gatcattcca ctcttggtat cacgttcgta   1260
tatggcatgt gcaaatcaga tcgttctgta gaacttattc tggattacag caacataact   1320
tttaatatgg catatatcat tgcccatgag atgggtcata gtctgggcat gttacatgac   1380
acaaaattct gtacttgtgg ggctaaacca tgcattatgt ttggcaaaga aagcattcca   1440
ccgcccaaag aattcagcag ttgtagttat gaccagtata acaagtatct tcttaaatat   1500
aacccaaaat gcattcttga tccaccttg cgtaaagata ttgcttcacc tgcagtttgt   1560
ggcaatgaaa tttgggagga aggtgaagaa tgtgattgtg ttctcctgc agattgtcgc   1620
aatccatgct gtgatgctgc aacatgtaaa ctgaaaccag gggcagaatg tggcaatggt   1680
gagtgttgtg acaagtgcaa gattcgtaaa gcaggcacag aatgccggcc agcacgcgat   1740
gactgtgatg tcgctgaaca ctgcactggc caatctgctg agtgtccccg taatgagttc   1800
caacgcaatg gtcaaccatg ccttaacaac tctggttatt gctacaatgg ggattgcccc   1860
atcatgttaa accaatgtat tgctctcttt agtccaagtg caactgtggc tcaagattca   1920
tgttttcagc gtaacttgca aggcagttac tatggctact gcacaaagga aattggttac   1980
tatggtaaac gctttccatg tgcaccacaa gatgtaaaat gtggccgttt atactgctta   2040
gataattcat tcaaaaaaaa tatgcgttgc aagaacgact attcatacgc ggatgaaaat   2100
aagggtatcg ttgaacctgg tacaaaatgt gaagatggta aggtctgcat caaccgcaag   2160
tgtgttgatg tgaatacagc ctaccatcac catcaccatc actag                   2205
```

<210> SEQ ID NO 36
<211> LENGTH: 706
<212> TYPE: PRT
<213> ORGANISM: Artificial Sequence
<220> FEATURE:
<223> OTHER INFORMATION: Construct pTAP525, alpha Fpp
      leader-pre-pro-GPR-Metalloprotease-Disintegrin-Cys rich-His tag

<400> SEQUENCE: 36

```
Met Arg Phe Pro Ser Ile Phe Thr Ala Val Leu Phe Ala Ala Ser Ser
1               5                   10                  15
```

```
Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Asp Lys Arg Ile Gln Ile Leu Leu Val Ile Ile Cys Leu Ala
                 85                  90                  95

Val Phe Pro Tyr Gln Gly Cys Ser Ile Ile Leu Gly Ser Gly Asn Val
            100                 105                 110

Asn Asp Tyr Glu Val Val Tyr Pro Gln Lys Val Thr Ala Leu Pro Lys
        115                 120                 125

Gly Ala Val Gln Gln Pro Glu Gln Lys Tyr Glu Asp Ala Met Gln Tyr
    130                 135                 140

Glu Phe Glu Val Lys Gly Glu Pro Val Val Leu His Leu Glu Lys Asn
145                 150                 155                 160

Lys Glu Leu Phe Ser Glu Asp Tyr Ser Glu Thr His Tyr Ser Ser Asp
                165                 170                 175

Asp Arg Glu Ile Thr Thr Asn Pro Ser Val Glu Asp His Cys Tyr Tyr
            180                 185                 190

His Gly Arg Ile Gln Asn Asp Ala Glu Ser Thr Ala Ser Ile Ser Ala
        195                 200                 205

Cys Asn Gly Leu Lys Gly His Phe Lys Leu Arg Gly Glu Thr Tyr Phe
    210                 215                 220

Ile Glu Pro Leu Lys Ile Pro Asp Ser Glu Ala His Ala Val Tyr Lys
225                 230                 235                 240

Tyr Glu Asn Ile Glu Asn Glu Asp Glu Ala Pro Lys Met Cys Gly Val
                245                 250                 255

Thr Gln Asp Asn Trp Glu Ser Asp Glu Pro Ile Lys Lys Thr Leu Gly
            260                 265                 270

Pro Arg Val Pro Pro His Glu Arg Lys Phe Glu Lys Lys Phe Ile Glu
        275                 280                 285

Leu Val Val Val Val Asp His Ser Met Val Thr Lys Tyr Asn Asn Asp
    290                 295                 300

Ser Thr Ala Ile Arg Thr Trp Ile Tyr Glu Met Leu Asn Thr Val Asn
305                 310                 315                 320

Glu Ile Tyr Leu Pro Phe Asn Ile Arg Val Ala Leu Val Gly Leu Glu
                325                 330                 335

Phe Trp Cys Asn Gly Asp Leu Ile Asn Val Thr Ser Thr Ala Asp Asp
            340                 345                 350

Thr Leu His Ser Phe Gly Glu Trp Arg Ala Ser Asp Leu Leu Asn Arg
        355                 360                 365

Lys Arg His Asp His Ala Gln Leu Leu Thr Asn Val Thr Leu Asp His
    370                 375                 380

Ser Thr Leu Gly Ile Thr Phe Val Tyr Gly Met Cys Lys Ser Asp Arg
385                 390                 395                 400

Ser Val Glu Leu Ile Leu Asp Tyr Ser Asn Ile Thr Phe Asn Met Ala
                405                 410                 415

Tyr Ile Ile Ala His Glu Met Gly His Ser Leu Gly Met Leu His Asp
            420                 425                 430

Thr Lys Phe Cys Thr Cys Gly Ala Lys Pro Cys Ile Met Phe Gly Lys
```

```
                435                 440                 445
Glu Ser Ile Pro Pro Lys Glu Phe Ser Ser Cys Ser Tyr Asp Gln
            450                 455                 460
Tyr Asn Lys Tyr Leu Leu Lys Tyr Asn Pro Lys Cys Ile Leu Asp Pro
465                 470                 475                 480
Pro Leu Arg Lys Asp Ile Ala Ser Pro Ala Val Cys Gly Asn Glu Ile
                485                 490                 495
Trp Glu Glu Gly Glu Glu Cys Asp Cys Gly Ser Pro Ala Asp Cys Arg
            500                 505                 510
Asn Pro Cys Cys Asp Ala Ala Thr Cys Lys Leu Lys Pro Gly Ala Glu
            515                 520                 525
Cys Gly Asn Gly Glu Cys Cys Asp Lys Cys Lys Ile Arg Lys Ala Gly
            530                 535                 540
Thr Glu Cys Arg Pro Ala Arg Asp Asp Cys Asp Val Ala Glu His Cys
545                 550                 555                 560
Thr Gly Gln Ser Ala Glu Cys Pro Arg Asn Glu Phe Gln Arg Asn Gly
                565                 570                 575
Gln Pro Cys Leu Asn Asn Ser Gly Tyr Cys Tyr Asn Gly Asp Cys Pro
            580                 585                 590
Ile Met Leu Asn Gln Cys Ile Ala Leu Phe Ser Pro Ser Ala Thr Val
                595                 600                 605
Ala Gln Asp Ser Cys Phe Gln Arg Asn Leu Gln Gly Ser Tyr Tyr Gly
            610                 615                 620
Tyr Cys Thr Lys Glu Ile Gly Tyr Tyr Gly Lys Arg Phe Pro Cys Ala
625                 630                 635                 640
Pro Gln Asp Val Lys Cys Gly Arg Leu Tyr Cys Leu Asp Asn Ser Phe
                645                 650                 655
Lys Lys Asn Met Arg Cys Lys Asn Asp Tyr Ser Tyr Ala Asp Glu Asn
            660                 665                 670
Lys Gly Ile Val Glu Pro Gly Thr Lys Cys Glu Asp Gly Lys Val Cys
            675                 680                 685
Ile Asn Arg Lys Cys Val Asp Val Asn Thr Ala Tyr His His His His
            690                 695                 700
His His
705

<210> SEQ ID NO 37
<211> LENGTH: 1902
<212> TYPE: DNA
<213> ORGANISM: Artificial Sequence
<220> FEATURE:
<223> OTHER INFORMATION: Construct pTAP524, beta gluconase
      leader-pro-GPR-Metalloprotease-Disintegrin-Cys rich-His tag

<400> SEQUENCE: 37
atgaagttct cgctaagtac attgacagtt atcaccacct tactatcatt ggtctcagct      60
gcaccactca ctttgaaaaa gagaggttgc tctataatcc tgggatctgg gaatgttaat     120
gattatgaag tagtgtatcc acaaaaagtc actgcattgc ccaaaggagc agttcagcag     180
cctgagcaaa agtatgaaga tgccatgcaa tatgaatttg aagtgaaggg agagccagtg     240
gtccttcacc tagaaaaaaa taagaacttt ttttcagaag attacagtga gactcattat     300
tcgtctgatg acagagaaat tacaacaaac ccttcagttg aggatcactg ctattatcat     360
ggacggatcc agaatgatgc tgagtcaact gcaagcatca gtgcatgcaa tggtttgaaa     420
ggacatttca agcttcgagg ggagacgtac tttattgaac ccttgaagat tcccgacagt     480
```

```
gaagcccatg cagtctacaa atatgaaaac atagaaaatg aggatgaagc ccccaaaatg    540 tgtgggtaa  cccaggataa ttgggaatca gatgaaccca tcaaaaagac tttggggcca    600
agagttcctc ctcatgaacg aaaatttgag aaaaaattca ttgagcttgt cgtagttgtg    660
gaccacagta tggtcacaaa atacaacaat gattcaactg ctatccgcac atggatctat    720
gaaatgctca acactgtaaa tgagatctac ttacctttca atattcgtgt agcactggtt    780
ggcctagaat tttggtgcaa tggtgacttg attaacgtga catccacagc agatgatact    840
ttgcactcat ttggcgaatg gcgcgcatca gatttgctga atcgtaaacg ccatgatcat    900
gctcagttac tcacgaacgt gacactggat cattccactc ttggtatcac gttcgtatat    960
ggcatgtgca atcagatcg  ttctgtagaa cttattctgg attacagcaa cataactttt   1020
aatatggcat atatcattgc ccatgagatg ggtcatagtc tgggcatgtt acatgacaca   1080
aaattctgta cttgtggggc taaccatgc  attatgtttg gcaaagaaag cattccaccg   1140
cccaaagaat tcagcagttg tagttatgac cagtataaca agtatcttct taaatataac   1200
ccaaaatgca ttcttgatcc acctttgcgt aaagatattg cttcacctgc agtttgtggc   1260
aatgaaattt gggaggaagg tgaagaatgt gattgtggtt ctcctgcaga ttgtcgcaat   1320
ccatgctgtg atgctgcaac atgtaaactg aaaccagggg cagaatgtgg caatggtgag   1380
tgttgtgaca gtgcaagat  tcgtaaagca ggcacagaat gccggccagc acgcgatgac   1440
tgtgatgtcg ctgaacactg cactggccaa tctgctgagt gtccccgtaa tgagttccaa   1500
cgcaatggtc aaccatgcct taacaactct ggttattgct acaatgggga ttgccccatc   1560
atgttaaacc aatgtattgc tctctttagt ccaagtgcaa ctgtggctca agattcatgt   1620
tttcagcgta acttgcaagg cagttactat ggctactgca caaggaaat  tggttactat   1680 ggtaaacgct ttccatgtgc accacaagat gtaaaatgtg gccgtttata ctgcttagat   1740
aattcattca aaaaaaatat gcgttgcaag aacgactatt catacgcgga tgaaaataag   1800
ggtatcgttg aacctggtac aaaatgtgaa gatggtaagg tctgcatcaa ccgcaagtgt   1860
gttgatgtga atacagccta ccatcaccat caccatcact ag                      1902
```

<210> SEQ ID NO 38
<211> LENGTH: 632
<212> TYPE: PRT
<213> ORGANISM: Artificial Sequence
<220> FEATURE:
<223> OTHER INFORMATION: Construct pTAP524, beta gluconase
      leader-pro-GPR-Metalloprotease-Disintegrin-Cys rich-His tag

<400> SEQUENCE: 38

Met Lys Phe Ser Leu Ser Thr Leu Thr Val Ile Thr Thr Leu Leu Ser
1               5                   10                  15

Leu Val Ser Ala Ala Pro Leu Thr Leu Lys Lys Arg Cys Ser Ile Ile
            20                  25                  30

Leu Gly Ser Gly Asn Val Asn Asp Tyr Glu Val Val Tyr Pro Gln Lys
        35                  40                  45

Val Thr Ala Leu Pro Lys Gly Ala Val Gln Gln Pro Glu Gln Lys Tyr
    50                  55                  60

Glu Asp Ala Met Gln Tyr Glu Phe Glu Val Lys Gly Glu Pro Val Val
65                  70                  75                  80

Leu His Leu Glu Lys Asn Lys Glu Leu Phe Ser Glu Asp Tyr Ser Glu
                85                  90                  95

Thr His Tyr Ser Ser Asp Asp Arg Glu Ile Thr Thr Asn Pro Ser Val

```
            100                 105                 110
Glu Asp His Cys Tyr Tyr His Gly Arg Ile Gln Asn Asp Ala Glu Ser
            115                 120                 125

Thr Ala Ser Ile Ser Ala Cys Asn Gly Leu Lys Gly His Phe Lys Leu
130                 135                 140

Arg Gly Glu Thr Tyr Phe Ile Glu Pro Leu Lys Ile Pro Asp Ser Glu
145                 150                 155                 160

Ala His Ala Val Tyr Lys Tyr Glu Asn Ile Glu Asn Glu Asp Glu Ala
                165                 170                 175

Pro Lys Met Cys Gly Val Thr Gln Asp Asn Trp Glu Ser Asp Glu Pro
            180                 185                 190

Ile Lys Lys Thr Leu Gly Pro Arg Val Pro Pro His Glu Arg Lys Phe
        195                 200                 205

Glu Lys Lys Phe Ile Glu Leu Val Val Val Asp His Ser Met Val
    210                 215                 220

Thr Lys Tyr Asn Asn Asp Ser Thr Ala Ile Arg Thr Trp Ile Tyr Glu
225                 230                 235                 240

Met Leu Asn Thr Val Asn Glu Ile Tyr Leu Pro Phe Asn Ile Arg Val
                245                 250                 255

Ala Leu Val Gly Leu Glu Phe Trp Cys Asn Gly Asp Leu Ile Asn Val
            260                 265                 270

Thr Ser Thr Ala Asp Asp Thr Leu His Ser Phe Gly Gly Trp Arg Ala
        275                 280                 285

Ser Asp Leu Leu Asn Arg Lys Arg His Asp His Ala Gln Leu Leu Thr
    290                 295                 300

Asn Val Thr Leu Asp His Ser Thr Leu Gly Ile Thr Phe Val Tyr Gly
305                 310                 315                 320

Met Cys Lys Ser Asp Arg Ser Val Glu Leu Ile Leu Asp Tyr Ser Asn
                325                 330                 335

Ile Thr Phe Asn Met Ala Tyr Ile Ile Ala His Glu Met Gly His Ser
            340                 345                 350

Leu Gly Met Leu His Asp Thr Lys Phe Cys Thr Cys Gly Ala Lys Pro
        355                 360                 365

Cys Ile Met Phe Gly Lys Glu Ser Ile Pro Pro Lys Glu Phe Ser
    370                 375                 380

Ser Cys Ser Tyr Asp Gln Tyr Asn Lys Tyr Leu Leu Lys Tyr Asn Pro
385                 390                 395                 400

Lys Cys Ile Leu Asp Pro Pro Leu Arg Lys Asp Ile Ala Ser Pro Ala
                405                 410                 415

Val Cys Gly Asn Glu Ile Trp Glu Glu Gly Glu Cys Asp Cys Gly
            420                 425                 430

Ser Pro Ala Asp Cys Arg Asn Pro Cys Cys Asp Ala Ala Thr Cys Lys
        435                 440                 445

Leu Lys Pro Gly Ala Glu Cys Gly Asn Gly Glu Cys Cys Asp Lys Cys
    450                 455                 460

Lys Ile Arg Lys Ala Gly Thr Glu Cys Arg Pro Ala Arg Asp Cys
465                 470                 475                 480

Asp Val Ala Glu His Cys Thr Gly Gln Ser Ala Glu Cys Pro Arg Asn
                485                 490                 495

Glu Phe Gln Arg Asn Gly Gln Pro Cys Leu Asn Asn Ser Gly Tyr Cys
            500                 505                 510

Tyr Asn Gly Asp Cys Pro Ile Met Leu Asn Gln Cys Ile Ala Leu Phe
        515                 520                 525
```

```
Ser Pro Ser Ala Thr Val Ala Gln Asp Ser Cys Phe Gln Arg Asn Leu
    530                 535                 540
Gln Gly Ser Tyr Tyr Gly Tyr Cys Thr Lys Glu Ile Gly Tyr Tyr Gly
545                 550                 555                 560
Lys Arg Phe Pro Cys Ala Pro Gln Asp Val Lys Cys Gly Arg Leu Tyr
                565                 570                 575
Cys Leu Asp Asn Ser Phe Lys Lys Asn Met Arg Cys Lys Asn Asp Tyr
            580                 585                 590
Ser Tyr Ala Asp Glu Asn Lys Gly Ile Val Glu Pro Gly Thr Lys Cys
        595                 600                 605
Glu Asp Gly Lys Val Cys Ile Asn Arg Lys Cys Val Asp Val Asn Thr
    610                 615                 620
Ala Tyr His His His His His His
625                 630

<210> SEQ ID NO 39
<211> LENGTH: 2073
<212> TYPE: DNA
<213> ORGANISM: Artificial Sequence
<220> FEATURE:
<223> OTHER INFORMATION: Construct pTAP526/537, alpha Fpp
      leader-pro-GPR-Metalloprotease-Disintegrin-Cys rich-His tag

<400> SEQUENCE: 39
```

| | | |
|---|---|---|
| atgagatttc cttctatttt tactgctgtt ttattcgctg cttcctccgc tttagctgct | 60 |
| ccagtcaaca ctaccactga agatgaaacg gctcaaattc cagctgaagc tgtcatcggt | 120 |
| tactctgatt tagaaggtga tttcgatgtt gctgttttgc cattttccaa ctccaccaat | 180 |
| aacggtttat tgtttatcaa tactactatt gctagcattg ctgctaaaga agaaggtgta | 240 |
| agcttggaca agagaggttg ctctataatc ctgggatctg ggaatgttaa tgattatgaa | 300 |
| gtagtgtatc cacaaaaagt cactgcattg cccaaaggag cagttcagca gcctgagcaa | 360 |
| aagtatgaag atgccatgca atatgaattt gaagtgaagg gagagccagt ggtccttcac | 420 |
| ctagaaaaaa ataaagaact tttttcagaa gattacagtg agactcatta ttcgtctgat | 480 |
| gacagagaaa ttacaacaaa cccttcagtt gaggatcact gctattatca tggacggatc | 540 |
| cagaatgatg ctgagtcaac tgcaagcatc agtgcatgca atggtttgaa aggacatttc | 600 |
| aagcttcgag gggagacgta ctttattgaa cccttgaaga ttcccgacag tgaagcccat | 660 |
| gcagtctaca atatgaaaaa catagaaaat gaggatgaag cccccaaaat gtgtggggta | 720 |
| acccaggata ttgggaatc agatgaaccc atcaaaaaga cttgggggcc aagagttcct | 780 |
| cctcatgaac gaaaatttga gaaaaaattc attgagcttg tcgtagttgt ggaccacagt | 840 |
| atggtcacaa aatacaacaa tgattcaact gctatccgca catggataa tgaaatgctc | 900 |
| aacactgtaa atgagatcta cttacctttc aatattcgtg tagcactggt tggcctagaa | 960 |
| ttttggtgca atggtgactt gattaacgtg acatccacag cagatgatac tttgcactca | 1020 |
| tttggcgaat ggcgcgcatc agatttgctg aatcgtaaac gccatgatca tgctcagtta | 1080 |
| ctcacgaacg tgacactgga tcattccact cttggtatca cgttcgtata tggcatgtgc | 1140 |
| aaatcagatc gttctgtaga acttattctg gattacagca acataacttt taatatggca | 1200 |
| tatatcattg cccatgagat gggtcatagt ctgggcatgt acatgacac aaaattctgt | 1260 |
| acttgtgggg ctaaaccatg cattatgttt ggcaaagaaa gcattccacc gcccaaagaa | 1320 |
| ttcagcagtt gtagttatga ccagtataac aagtatcttc ttaaatataa cccaaaatgc | 1380 |

```
attcttgatc caccttttgcg taaagatatt gcttcacctg cagtttgtgg caatgaaatt      1440
tgggaggaag gtgaagaatg tgattgtggt tctcctgcag attgtcgcaa tccatgctgt      1500
gatgctgcaa catgtaaact gaaaccaggg gcagaatgtg gcaatggtga gtgttgtgac      1560
aagtgcaaga ttcgtaaagc aggcacagaa tgccggccag cacgcgatga ctgtgatgtc      1620
gctgaacact gcactggcca atctgctgag tgtccccgta atgagttcca acgcaatggt      1680
caaccatgcc ttaacaactc tggttattgc tacaatgggg attgccccat catgttaaac      1740
caatgtattg ctctctttag tccaagtgca actgtggctc aagattcatg ttttcagcgt      1800
aacttgcaag gcagttacta tggctactgc acaaaggaaa ttggttacta tggtaaacgc      1860
tttccatgtg caccacaaga tgtaaaatgt ggccgtttat actgcttaga taattcattc      1920
aaaaaaaata tgcgttgcaa gaacgactat tcatacgcgg atgaaaataa gggtatcgtt      1980
gaacctggta caaaatgtga agatggtaag gtctgcatca accgcaagtg tgttgatgtg      2040
aatacagcct accatcacca tcaccatcac tag                                   2073
```

<210> SEQ ID NO 40
<211> LENGTH: 689
<212> TYPE: PRT
<213> ORGANISM: Artificial Sequence
<220> FEATURE:
<223> OTHER INFORMATION: Construct pTAP526/537, alpha Fpp
      leader-pro-GPR-Metalloprotease-Disintegrin-Cys rich-His tag

<400> SEQUENCE: 40

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Cys Ser Ile Ile Leu Gly Ser Gly Asn Val Asn
                85                  90                  95

Asp Tyr Glu Val Val Tyr Pro Gln Lys Val Thr Ala Leu Pro Lys Gly
            100                 105                 110

Ala Val Gln Gln Pro Glu Gln Lys Tyr Glu Asp Ala Met Gln Tyr Glu
        115                 120                 125

Phe Glu Val Lys Gly Glu Pro Val Val Leu His Leu Glu Lys Asn Lys
    130                 135                 140

Glu Leu Phe Ser Glu Asp Tyr Ser Glu Thr His Tyr Ser Ser Asp Asp
145                 150                 155                 160

Arg Glu Ile Thr Thr Asn Pro Ser Val Glu Asp His Cys Tyr Tyr His
                165                 170                 175

Gly Arg Ile Gln Asn Asp Ala Glu Ser Thr Ala Ser Ile Ser Ala Cys
            180                 185                 190

Asn Gly Leu Lys Gly His Phe Lys Leu Arg Gly Glu Thr Tyr Phe Ile
        195                 200                 205

Glu Pro Leu Lys Ile Pro Asp Ser Glu Ala His Ala Val Tyr Lys Tyr
    210                 215                 220

Glu Asn Ile Glu Asn Glu Asp Glu Ala Pro Lys Met Cys Gly Val Thr
225                 230                 235                 240
```

```
Gln Asp Asn Trp Glu Ser Asp Glu Pro Ile Lys Lys Thr Leu Gly Pro
                245                 250                 255

Arg Val Pro Pro His Glu Arg Lys Phe Glu Lys Lys Phe Ile Glu Leu
            260                 265                 270

Val Val Val Val Asp His Ser Met Val Thr Lys Tyr Asn Asn Asp Ser
        275                 280                 285

Thr Ala Ile Arg Thr Trp Ile Tyr Glu Met Leu Asn Thr Val Asn Glu
    290                 295                 300

Ile Tyr Leu Pro Phe Asn Ile Arg Val Ala Leu Val Gly Leu Glu Phe
305                 310                 315                 320

Trp Cys Asn Gly Asp Leu Ile Asn Val Thr Ser Thr Ala Asp Asp Thr
                325                 330                 335

Leu His Ser Phe Gly Glu Trp Arg Ala Ser Asp Leu Leu Asn Arg Lys
            340                 345                 350

Arg His Asp His Ala Gln Leu Leu Thr Asn Val Thr Leu Asp His Ser
        355                 360                 365

Thr Leu Gly Ile Thr Phe Val Tyr Gly Met Cys Lys Ser Asp Arg Ser
    370                 375                 380

Val Glu Leu Ile Leu Asp Tyr Ser Asn Ile Thr Phe Asn Met Ala Tyr
385                 390                 395                 400

Ile Ile Ala His Glu Met Gly His Ser Leu Gly Met Leu His Asp Thr
                405                 410                 415

Lys Phe Cys Thr Cys Gly Ala Lys Pro Cys Ile Met Phe Gly Lys Glu
            420                 425                 430

Ser Ile Pro Pro Pro Lys Glu Phe Ser Ser Cys Ser Tyr Asp Gln Tyr
        435                 440                 445

Asn Lys Tyr Leu Leu Lys Tyr Asn Pro Lys Cys Ile Leu Asp Pro Pro
    450                 455                 460

Leu Arg Lys Asp Ile Ala Ser Pro Ala Val Cys Gly Asn Glu Ile Trp
465                 470                 475                 480

Glu Glu Gly Glu Glu Cys Asp Cys Gly Ser Pro Ala Asp Cys Arg Asn
                485                 490                 495

Pro Cys Cys Asp Ala Ala Thr Cys Lys Leu Lys Pro Gly Ala Glu Cys
            500                 505                 510

Gly Asn Gly Glu Cys Cys Asp Lys Cys Lys Ile Arg Lys Ala Gly Thr
        515                 520                 525

Glu Cys Arg Pro Ala Arg Asp Cys Asp Val Ala Glu His Cys Thr
    530                 535                 540

Gly Gln Ser Ala Glu Cys Pro Arg Asn Glu Phe Gln Arg Asn Gly Gln
545                 550                 555                 560

Pro Cys Leu Asn Asn Ser Gly Tyr Cys Tyr Asn Gly Asp Cys Pro Ile
                565                 570                 575

Met Leu Asn Gln Cys Ile Ala Leu Phe Ser Pro Ser Ala Thr Val Ala
            580                 585                 590

Gln Asp Ser Cys Phe Gln Arg Asn Leu Gln Gly Ser Tyr Gly Tyr
        595                 600                 605

Cys Thr Lys Glu Ile Gly Tyr Tyr Gly Lys Arg Phe Pro Cys Ala Pro
    610                 615                 620

Gln Asp Val Lys Cys Gly Arg Leu Tyr Cys Leu Asp Asn Ser Phe Lys
625                 630                 635                 640

Lys Asn Met Arg Cys Lys Asn Asp Tyr Ser Tyr Ala Asp Glu Asn Lys
                645                 650                 655
```

```
Gly Ile Val Glu Pro Gly Thr Lys Cys Glu Asp Gly Lys Val Cys Ile
            660                 665                 670

Asn Arg Lys Cys Val Asp Val Asn Thr Ala Tyr His His His His His
        675                 680                 685

His

<210> SEQ ID NO 41
<211> LENGTH: 1869
<212> TYPE: DNA
<213> ORGANISM: Artificial Sequence
<220> FEATURE:
<223> OTHER INFORMATION: Construct pTAP536/529/532,
      Pre-pro-GPR-Metalloprotease-Disintegrin-Cys rich-His tag

<400> SEQUENCE: 41
atgatccaga ttctcttggt aattatatgc ttagcagttt ttccatatca aggttgctct      60
ataatcctgg gatctgggaa tgttaatgat tatgaagtag tgtatccaca aaaagtcact     120
gcattgccca aggagcagt tcagcagcct gagcaaaagt atgaagatgc catgcaatat      180
gaatttgaag tgaagggaga gccagtggtc cttcacctag aaaaaaataa agaactttt      240 tcagaagatt acagtgagac tcattattcg tctgatgaca gagaaattac aacaaaccct     300
tcagttgagg atcactgcta ttatcatgga cggatccaga atgatgctga gtcaactgca     360
agcatcagtg catgcaatgg tttgaaagga catttcaagc ttcgagggga gacgtacttt     420
attgaaccct tgaagattcc cgacagtgaa gcccatgcag tctacaaata tgaaaacata     480
gaaaatgagg atgaagcccc caaaatgtgt ggggtaaccc aggataattg ggaatcagat     540
gaacccatca aaaagacttt ggggccaaga gttcctcctc atgaacgaaa atttgagaaa     600
aaattcattg agcttgtcgt agttgtggac cacagtatgg tcacaaaata caacaatgat     660
tcaactgcta tccgcacatg gatctatgaa atgctcaaca ctgtaaatga gatctactta     720
cctttcaata ttcgtgtagc actggttggc ctagaatttt ggtgcaatgg tgacttgatt     780
aacgtgacat ccacagcaga tgatactttg cactcatttg gcgaatggcg cgcatcagat     840
ttgctgaatc gtaaacgcca tgatcatgct cagttactca cgaacgtgac actggatcat     900
tccactcttg gtatcacgtt cgtatatggc atgtgcaaat cagatcgttc tgtagaactt     960
attctggatt acagcaacat aacttttaat atggcatata tcattgccca tgagatgggt    1020
catagtctgg gcatgttaca tgacacaaaa ttctgtactt gtgggggctaa accatgcatt    1080 atgtttggca agaaaagcat tccaccgccc aaagaattca gcagttgtag ttatgaccag    1140
tataacaagt atcttcttaa atataaccca aaatgcattc ttgatccacc tttgcgtaaa    1200
gatattgctt cacctgcagt ttgtggcaat gaaatttggg aggaaggtga agaatgtgat    1260
tgtggttctc ctgcagattg tcgcaatcca tgctgtgatg ctgcaacatg taaactgaaa    1320
ccaggggcag aatgtggcaa tggtgagtgt tgtgacaagt gcaagattcg taaagcaggc    1380
acagaatgcc ggccagcacg cgatgactgt gatgtcgctg aacactgcac tggccaatct    1440
gctgagtgtc cccgtaatga gttccaacgc aatggtcaac catgccttaa caactctggt    1500
tattgctaca tgggggattg ccccatcatg ttaaaccaat gtattgctct ctttagtcca    1560
agtgcaactg tggctcaaga ttcatgtttt cagcgtaact tgcaaggcag ttactatggc    1620
tactgcacaa aggaaattgg ttactatggt aaacgctttc catgtgcacc acaagatgta    1680
aaatgtggcc gttatactg cttagataat tcattcaaaa aaaatatgcg ttgcaagaac    1740
gactattcat acgcggatga aaataagggt atcgttgaac ctggtacaaa atgtgaagat    1800
```

-continued

```
ggtaaggtct gcatcaaccg caagtgtgtt gatgtgaata cagcctacca tcaccatcac    1860
catcactag                                                            1869
```

<210> SEQ ID NO 42
<211> LENGTH: 622
<212> TYPE: PRT
<213> ORGANISM: Artificial Sequence
<220> FEATURE:
<223> OTHER INFORMATION: Construct pTAP536/529/532,
      Pre-pro-GPR-Metalloprotease-Disintegrin-Cys rich-His tag

<400> SEQUENCE: 42

```
Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Arg Glu Ile
                85                  90                  95

Thr Thr Asn Pro Ser Val Glu Asp His Cys Tyr Tyr His Gly Arg Ile
                100                 105                 110

Gln Asn Asp Ala Glu Ser Thr Ala Ser Ile Ser Ala Cys Asn Gly Leu
            115                 120                 125

Lys Gly His Phe Lys Leu Arg Gly Glu Thr Tyr Phe Ile Glu Pro Leu
        130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Pro Arg Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
    210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
    290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
```

```
                       340                 345                 350
Thr Cys Gly Ala Lys Pro Cys Ile Met Phe Lys Glu Ser Ile Pro
        355                 360                 365
Pro Pro Lys Glu Phe Ser Ser Cys Ser Tyr Asp Gln Tyr Asn Lys Tyr
    370                 375                 380
Leu Leu Lys Tyr Asn Pro Lys Cys Ile Leu Asp Pro Pro Leu Arg Lys
385                 390                 395                 400
Asp Ile Ala Ser Pro Ala Val Cys Gly Asn Glu Ile Trp Glu Glu Gly
                405                 410                 415
Glu Glu Cys Asp Cys Gly Ser Pro Ala Asp Cys Arg Asn Pro Cys Cys
                420                 425                 430
Asp Ala Ala Thr Cys Lys Leu Lys Pro Gly Ala Glu Cys Gly Asn Gly
                435                 440                 445
Glu Cys Cys Asp Lys Cys Lys Ile Arg Lys Ala Gly Thr Glu Cys Arg
        450                 455                 460
Pro Ala Arg Asp Asp Cys Asp Val Ala Glu His Cys Thr Gly Gln Ser
465                 470                 475                 480
Ala Glu Cys Pro Arg Asn Glu Phe Gln Arg Asn Gly Gln Pro Cys Leu
                485                 490                 495
Asn Asn Ser Gly Tyr Cys Tyr Asn Gly Asp Cys Pro Ile Met Leu Asn
                500                 505                 510
Gln Cys Ile Ala Leu Phe Ser Pro Ser Ala Thr Val Ala Gln Asp Ser
        515                 520                 525
Cys Phe Gln Arg Asn Leu Gln Gly Ser Tyr Tyr Gly Tyr Cys Thr Lys
        530                 535                 540
Glu Ile Gly Tyr Tyr Gly Lys Arg Phe Pro Cys Ala Pro Gln Asp Val
545                 550                 555                 560
Lys Cys Gly Arg Leu Tyr Cys Leu Asp Asn Ser Phe Lys Lys Asn Met
                565                 570                 575
Arg Cys Lys Asn Asp Tyr Ser Tyr Ala Asp Glu Asn Lys Gly Ile Val
                580                 585                 590
Glu Pro Gly Thr Lys Cys Glu Asp Gly Lys Val Cys Ile Asn Arg Lys
                595                 600                 605
Cys Val Asp Val Asn Thr Ala Tyr His His His His His
        610                 615                 620

<210> SEQ ID NO 43
<211> LENGTH: 1353
<212> TYPE: DNA
<213> ORGANISM: Artificial Sequence
<220> FEATURE:
<223> OTHER INFORMATION: Construct pTAP544, Gal1-aga2
      leader-Metalloprotease-Disintegrin-Cys rich-His tag

<400> SEQUENCE: 43
atgcagttac ttcgctgttt ttcaatattt tctgttattg cttcagtttt agcagttcct      60
cctcatgaac gaaatttga gaaaaaattc attgagcttg tcgtagttgt ggaccacagt     120
atggtcacaa atacaacaa tgattcaact gctatccgca catggatcta tgaaatgctc     180
aacactgtaa atgagatcta cttacctttc aatattcgtg tagcactggt tggcctagaa     240
ttttggtgca atggtgactt gattaacgtg acatccacag cagatgatac tttgcactca     300
tttggcgaat ggcgcgcatc agatttgctg aatcgtaaac gccatgatca tgctcagtta     360
ctcacgaacg tgacactgga tcattccact cttggtatca cgttcgtata tggcatgtgc     420
aaatcagatc gttctgtaga acttattctg gattacagca acataacttt taatatggca     480
```

```
tatatcattg cccatgagat gggtcatagt ctgggcatgt tacatgacac aaaattctgt    540
acttgtgggg ctaaaccatg cattatgttt ggcaaagaaa gcattccacc gcccaaagaa    600
ttcagcagtt gtagttatga ccagtataac aagtatcttc ttaaatataa cccaaaatgc    660
attcttgatc cacctttgcg taaagatatt gcttcacctg cagtttgtgg caatgaaatt    720
tgggaggaag gtgaagaatg tgattgtggt tctcctgcag attgtcgcaa tccatgctgt    780
gatgctgcaa catgtaaact gaaaccaggg gcagaatgtg gcaatggtga gtgttgtgac    840
aagtgcaaga ttcgtaaagc aggcacagaa tgccggccag cacgcgatga ctgtgatgtc    900
gctgaacact gcactggcca atctgctgag tgtccccgta atgagttcca acgcaatggt    960
caaccatgcc ttaacaactc tggttattgc tacaatgggg attgccccat catgttaaac    1020
caatgtattg ctctctttag tccaagtgca actgtggctc aagattcatg ttttcagcgt    1080
aacttgcaag gcagttacta tggctactgc acaaaggaaa ttggttacta tggtaaacgc    1140
tttccatgtg caccacaaga tgtaaaatgt ggccgtttat actgcttaga taattcattc    1200
aaaaaaaata tgcgttgcaa gaacgactat tcatacgcgg atgaaaataa gggtatcgtt    1260
gaacctggta caaaatgtga agatggtaag gtctgcatca accgcaagtg tgttgatgtg    1320
aatacagcct accatcacca tcaccatcac tag                                1353
```

<210> SEQ ID NO 44
<211> LENGTH: 450
<212> TYPE: PRT
<213> ORGANISM: Artificial Sequence
<220> FEATURE:
<223> OTHER INFORMATION: Construct pTAP544, Gal1-aga2
      leader-Metalloprotease-Disintegrin-Cys rich-His tag

<400> SEQUENCE: 44

```
Met Gln Leu Leu Arg Cys Phe Ser Ile Phe Ser Val Ile Ala Ser Val
1               5                   10                  15

Leu Ala Val Pro Pro His Glu Arg Lys Phe Glu Lys Lys Phe Ile Glu
            20                  25                  30

Leu Val Val Val Val Asp His Ser Met Val Thr Lys Tyr Asn Asn Asp
        35                  40                  45

Ser Thr Ala Ile Arg Thr Trp Ile Tyr Glu Met Leu Asn Thr Val Asn
    50                  55                  60

Glu Ile Tyr Leu Pro Phe Asn Ile Arg Val Ala Leu Val Gly Leu Glu
65                  70                  75                  80

Phe Trp Cys Asn Gly Asp Leu Ile Asn Val Thr Ser Thr Ala Asp Asp
                85                  90                  95

Thr Leu His Ser Phe Gly Glu Trp Arg Ala Ser Asp Leu Leu Asn Arg
            100                 105                 110

Lys Arg His Asp His Ala Gln Leu Leu Thr Asn Val Thr Leu Asp His
        115                 120                 125

Ser Thr Leu Gly Ile Thr Phe Val Tyr Gly Met Cys Lys Ser Asp Arg
    130                 135                 140

Ser Val Glu Leu Ile Leu Asp Tyr Ser Asn Ile Thr Phe Asn Met Ala
145                 150                 155                 160

Tyr Ile Ile Ala His Glu Met Gly His Ser Leu Gly Met Leu His Asp
                165                 170                 175

Thr Lys Phe Cys Thr Cys Gly Ala Lys Pro Cys Ile Met Phe Gly Lys
            180                 185                 190

Glu Ser Ile Pro Pro Pro Lys Glu Phe Ser Ser Cys Ser Tyr Asp Gln
```

195                 200                 205
Tyr Asn Lys Tyr Leu Leu Lys Tyr Asn Pro Lys Cys Ile Leu Asp Pro
    210                 215                 220

Pro Leu Arg Lys Asp Ile Ala Ser Pro Ala Val Cys Gly Asn Glu Ile
225                 230                 235                 240

Trp Glu Glu Gly Glu Cys Asp Cys Gly Ser Pro Ala Asp Cys Arg
                245                 250                 255

Asn Pro Cys Cys Asp Ala Ala Thr Cys Lys Leu Lys Pro Gly Ala Glu
            260                 265                 270

Cys Gly Asn Gly Glu Cys Cys Asp Lys Cys Lys Ile Arg Lys Ala Gly
            275                 280                 285

Thr Glu Cys Arg Pro Ala Arg Asp Asp Cys Asp Val Ala Glu His Cys
            290                 295                 300

Thr Gly Gln Ser Ala Glu Cys Pro Arg Asn Glu Phe Gln Arg Asn Gly
305                 310                 315                 320

Gln Pro Cys Leu Asn Asn Ser Gly Tyr Cys Tyr Asn Gly Asp Cys Pro
                325                 330                 335

Ile Met Leu Asn Gln Cys Ile Ala Leu Phe Ser Pro Ser Ala Thr Val
            340                 345                 350

Ala Gln Asp Ser Cys Phe Gln Arg Asn Leu Gln Gly Ser Tyr Tyr Gly
            355                 360                 365

Tyr Cys Thr Lys Glu Ile Gly Tyr Tyr Gly Lys Arg Phe Pro Cys Ala
            370                 375                 380

Pro Gln Asp Val Lys Cys Gly Arg Leu Tyr Cys Leu Asp Asn Ser Phe
385                 390                 395                 400

Lys Lys Asn Met Arg Cys Lys Asn Asp Tyr Ser Tyr Ala Asp Glu Asn
                405                 410                 415

Lys Gly Ile Val Glu Pro Gly Thr Lys Cys Glu Asp Gly Lys Val Cys
            420                 425                 430

Ile Asn Arg Lys Cys Val Asp Val Asn Thr Ala Tyr His His His His
            435                 440                 445

His His
    450

<210> SEQ ID NO 45
<211> LENGTH: 711
<212> TYPE: DNA
<213> ORGANISM: Artificial Sequence
<220> FEATURE:
<223> OTHER INFORMATION: Construct pTAP490, STII leader-Metalloprotease-
      His tag

<400> SEQUENCE: 45
atgaagaaaa acatcgcttt tcttcttgca tctatgttcg ttttttctat tgctacaaac      60
gcgtatgcag ttcctcctca tgaacgaaaa tttgagaaaa aattcattga gcttgtcgta     120
gttgtggacc acagtatggt cacaaaatac aacaatgatt caactgctat ccgcacatgg     180
atctatgaaa tgctcaacac tgtaaatgag atctacttac ctttcaatat tcgtgtagca     240
ctggttggcc tagaattttg tgcaatggt gacttgatta acgtgacatc cacagcagat     300
gatactttgc actcatttgg cgaatggcgc gcatcagatt tgctgaatcg taaacgccat     360
gatcatgctc agttactcac gaacgtgaca ctggatcatt ccactcttgg tatcacgttc     420
gtatatggca tgtgcaaatc agatcgttct gtagaactta ttctggatta cagcaacata     480
acttttaata tggcatatat cattgcccat gagatgggtc atagtctggg catgttacat     540

-continued

```
gacacaaaat tctgtacttg tggggctaaa ccatgcatta tgtttggcaa agaaagcatt    600
ccaccgccca agaattcag cagttgtagt tatgaccagt ataacaagta tcttcttaaa    660
tataacccaa aatgcattct tgatccacct catcaccatc accatcacta a            711
```

<210> SEQ ID NO 46
<211> LENGTH: 236
<212> TYPE: PRT
<213> ORGANISM: Artificial Sequence
<220> FEATURE:
<223> OTHER INFORMATION: Construct pTAP490, STII leader-Metalloprotease-
    His tag

<400> SEQUENCE: 46

```
Met Lys Lys Asn Ile Ala Phe Leu Leu Ala Ser Met Phe Val Phe Ser
1               5                   10                  15

Ile Ala Thr Asn Ala Tyr Ala Val Pro Pro His Glu Arg Lys Phe Glu
            20                  25                  30

Lys Lys Phe Ile Glu Leu Val Val Val Asp His Ser Met Val Thr
        35                  40                  45

Lys Tyr Asn Asn Asp Ser Thr Ala Ile Arg Thr Trp Ile Tyr Glu Met
    50                  55                  60

Leu Asn Thr Val Asn Glu Ile Tyr Leu Pro Phe Asn Ile Arg Val Ala
65                  70                  75                  80

Leu Val Gly Leu Glu Phe Trp Cys Asn Gly Asp Leu Ile Asn Val Thr
                85                  90                  95

Ser Thr Ala Asp Asp Thr Leu His Ser Phe Gly Glu Trp Arg Ala Ser
            100                 105                 110

Asp Leu Leu Asn Arg Lys Arg His Asp His Ala Gln Leu Leu Thr Asn
        115                 120                 125

Val Thr Leu Asp His Ser Thr Leu Gly Ile Thr Phe Val Tyr Gly Met
    130                 135                 140

Cys Lys Ser Asp Arg Ser Val Glu Leu Ile Leu Asp Tyr Ser Asn Ile
145                 150                 155                 160

Thr Phe Asn Met Ala Tyr Ile Ile Ala His Glu Met Gly His Ser Leu
                165                 170                 175

Gly Met Leu His Asp Thr Lys Phe Cys Thr Cys Gly Ala Lys Pro Cys
            180                 185                 190

Ile Met Phe Gly Lys Glu Ser Ile Pro Pro Lys Glu Phe Ser Ser
        195                 200                 205

Cys Ser Tyr Asp Gln Tyr Asn Lys Tyr Leu Leu Lys Tyr Asn Pro Lys
    210                 215                 220

Cys Ile Leu Asp Pro Pro His His His His His His
225                 230                 235
```

<210> SEQ ID NO 47
<211> LENGTH: 1869
<212> TYPE: DNA
<213> ORGANISM: Artificial Sequence
<220> FEATURE:
<223> OTHER INFORMATION: Construct pTAP529/532/536,
    met-pre-pro-GPR-Metalloprotease-Disintegrin-Cys rich-His tag

<400> SEQUENCE: 47

```
atgatccaga ttctcttggt aattatatgc ttagcagttt ttccatatca aggttgctct    60
ataatcctgg gatctgggaa tgttaatgat tatgaagtag tgtatccaca aaaagtcact   120
gcattgccca aggagcagt tcagcagcct gagcaaaagt atgaagatgc catgcaatat   180
```

```
gaatttgaag tgaagggaga gccagtggtc cttcacctag aaaaaaataa agaactttt     240 tcagaagatt acagtgagac tcattattcg tctgatgaca gagaaattac aacaaaccct    300
tcagttgagg atcactgcta ttatcatgga cggatccaga atgatgctga gtcaactgca    360
agcatcagtg catgcaatgg tttgaaagga catttcaagc ttcgagggga gacgtacttt    420
attgaaccct tgaagattcc cgacagtgaa gcccatgcag tctacaaata tgaaaacata    480
gaaaatgagg atgaagcccc caaaatgtgt ggggtaaccc aggataattg ggaatcagat    540
gaacccatca aaagactttg gggccaagaa gttcctcctc atgaacgaaa atttgagaaa    600
aaattcattg agcttgtcgt agttgtggac cacagtatgg tcacaaaata caacaatgat    660
tcaactgcta tccgcacatg gatctatgaa atgctcaaca ctgtaaatga gatctactta    720
cctttcaata ttcgtgtagc actggttggc ctagaatttt ggtgcaatgg tgacttgatt    780
aacgtgacat ccacagcaga tgatactttg cactcatttg gcgaatggcg cgcatcagat    840
ttgctgaatc gtaaacgcca tgatcatgct cagttactca cgaacgtgac actggatcat    900
tccactcttg gtatcacgtt cgtatatggc atgtgcaaat cagatcgttc tgtagaactt    960
attctggatt acagcaacat aacttttaat atggcatata tcattgccca tgagatgggt   1020
catagtctgg gcatgttaca tgacacaaaa ttctgtactt gtggggctaa accatgcatt   1080
atgtttggca agaaaagcat tccaccgccc aaagaattca gcagttgtag ttatgaccag   1140
tataacaagt atcttcttaa atataaccca aaatgcattc ttgatccacc tttgcgtaaa   1200
gatattgctt cacctgcagt ttgtggcaat gaaatttggg aggaaggtga agaatgtgat   1260
tgtggttctc ctgcagattg tcgcaatcca tgctgtgatg ctgcaacatg taaactgaaa   1320
ccaggggcag aatgtggcaa tggtgagtgt tgtgacaagt gcaagattcg taaagcaggc   1380
acagaatgcc ggccagcacg cgatgactgt gatgtcgctg aacactgcac tggccaatct   1440
gctgagtgtc cccgtaatga gttccaacgc aatggtcaac catgccttaa caactctggt   1500
tattgctaca tggggattg ccccatcatg ttaaaccaat gtattgctct ctttagtcca   1560
agtgcaactg tggctcaaga ttcatgtttt cagcgtaact tgcaaggcag ttactatggc   1620
tactgcacaa aggaaattgg ttactatggt aaacgctttc catgtgcacc acaagatgta   1680
aaatgtggcc gtttatactg cttagataat tcattcaaaa aaaatatgcg ttgcaagaac   1740
gactattcat acgcggatga aaataagggg atcgttgaac ctggtacaaa atgtgaagat   1800
ggtaaggtct gcatcaaccg caagtgtgtt gatgtgaata cagcctacca tcaccatcac   1860
catcactag                                                            1869
```

<210> SEQ ID NO 48
<211> LENGTH: 622
<212> TYPE: PRT
<213> ORGANISM: Artificial Sequence
<220> FEATURE:
<223> OTHER INFORMATION: Construct pTAP529/532/536,
      met-pre-pro-GPR-Metalloprotease-Disintegrin-Cys rich-His tag

<400> SEQUENCE: 48

```
Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
```

```
            50                  55                  60
Lys Gly Glu Pro Val Val Leu His Leu Glu Lys Asn Lys Glu Leu Phe
 65                  70                  75                  80

Ser Glu Asp Tyr Ser Glu Thr His Tyr Ser Ser Asp Arg Glu Ile
                     85                  90                  95

Thr Thr Asn Pro Ser Val Glu Asp His Cys Tyr Tyr His Gly Arg Ile
                100                 105                 110

Gln Asn Asp Ala Glu Ser Thr Ala Ser Ile Ser Ala Cys Asn Gly Leu
                115                 120                 125

Lys Gly His Phe Lys Leu Arg Gly Glu Thr Tyr Phe Ile Glu Pro Leu
130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Pro Arg Val Pro
                180                 185                 190

Pro His Glu Arg Lys Phe Glu Lys Lys Phe Ile Glu Leu Val Val Val
                195                 200                 205

Val Asp His Ser Met Val Thr Lys Tyr Asn Asn Asp Ser Thr Ala Ile
210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
                260                 265                 270

Phe Gly Glu Trp Arg Ala Ser Asp Leu Leu Asn Arg Lys Arg His Asp
                275                 280                 285

His Ala Gln Leu Leu Thr Asn Val Thr Leu Asp His Ser Thr Leu Gly
                290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
                340                 345                 350

Thr Cys Gly Ala Lys Pro Cys Ile Met Phe Gly Lys Glu Ser Ile Pro
                355                 360                 365

Pro Pro Lys Glu Phe Ser Ser Cys Ser Tyr Asp Gln Tyr Asn Lys Tyr
                370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
                405                 410                 415

Glu Glu Cys Asp Cys Gly Ser Pro Ala Asp Cys Arg Asn Pro Cys Cys
                420                 425                 430

Asp Ala Ala Thr Cys Lys Leu Lys Pro Gly Ala Glu Cys Gly Asn Gly
                435                 440                 445

Glu Cys Cys Asp Lys Cys Lys Ile Arg Lys Ala Gly Thr Glu Cys Arg
                450                 455                 460

Pro Ala Arg Asp Asp Cys Asp Val Ala Glu His Cys Thr Gly Gln Ser
465                 470                 475                 480
```

```
Ala Glu Cys Pro Arg Asn Glu Phe Gln Arg Asn Gly Gln Pro Cys Leu
            485                 490                 495

Asn Asn Ser Gly Tyr Cys Tyr Asn Gly Asp Cys Pro Ile Met Leu Asn
        500                 505                 510

Gln Cys Ile Ala Leu Phe Ser Pro Ser Ala Thr Val Ala Gln Asp Ser
        515                 520                 525

Cys Phe Gln Arg Asn Leu Gln Gly Ser Tyr Gly Tyr Cys Thr Lys
        530                 535                 540

Glu Ile Gly Tyr Tyr Gly Lys Arg Phe Pro Cys Ala Pro Gln Asp Val
545                 550                 555                 560

Lys Cys Gly Arg Leu Tyr Cys Leu Asp Asn Ser Phe Lys Lys Asn Met
                565                 570                 575

Arg Cys Lys Asn Asp Tyr Ser Tyr Ala Asp Glu Asn Lys Gly Ile Val
            580                 585                 590

Glu Pro Gly Thr Lys Cys Glu Asp Gly Lys Val Cys Ile Asn Arg Lys
        595                 600                 605

Cys Val Asp Val Asn Thr Ala Tyr His His His His His
        610                 615                 620

<210> SEQ ID NO 49
<211> LENGTH: 2073
<212> TYPE: DNA
<213> ORGANISM: Artificial Sequence
<220> FEATURE:
<223> OTHER INFORMATION: Construct pTAP537/526, alpha Fpp
      leader-pro-GPR-Metalloprotease-Disintegrin-Cys rich-His tag

<400> SEQUENCE: 49
atgagatttc cttctatttt tactgctgtt ttattcgctg cttcctccgc tttagctgct     60
ccagtcaaca ctaccactga agatgaaacg gctcaaattc cagctgaagc tgtcatcggt    120
tactctgatt tagaaggtga tttcgatgtt gctgttttgc cattttccaa ctccaccaat    180
aacggtttat tgtttatcaa tactactatt gctagcattg ctgctaaaga agaaggtgta    240
agcttggaca gagaggttg ctctataatc ctgggatctg ggaatgttaa tgattatgaa     300
gtagtgtatc cacaaaaagt cactgcattg cccaaaggag cagttcagca gcctgagcaa    360
aagtatgaag atgccatgca atatgaattt gaagtgaagg gagagccagt ggtccttcac    420
ctagaaaaaa ataaagaact ttttcagaa gattacagtg agactcatta ttcgtctgat     480
gacagagaaa ttcaacaaa cccttcagtt gaggatcact gctattatca tggacggatc    540
cagaatgatg ctgagtcaac tgcaagcatc agtgcatgca atggtttgaa aggacatttc    600
aagcttcgag gggagacgta ctttattgaa cccttgaaga ttcccgacag tgaagcccat    660
gcagtctaca aatatgaaaa catagaaaat gaggatgaag cccccaaaat gtgtgggta    720 acccaggata attgggaatc agatgaaccc atcaaaaaga ctttggggcc aagagttcct    780
cctcatgaac gaaatttga gaaaaaattc attgagcttg tcgtagttgt ggaccacagt    840
atggtcacaa atacaacaa tgattcaact gctatccgca catggatcta tgaaatgctc    900
aacactgtaa atgagatcta cttacctttc aatattcgtg tagcactggt tggcctagaa    960
ttttggtgca atggtgactt gattaacgtg acatccacag cagatgatac tttgcactca   1020 tttgcgaat ggcgcgcatc agatttgctg aatcgtaaac gccatgatca tgctcagtta   1080
ctcacgaacg tgacactgga tcattccact cttggtatca cgttcgtata tggcatgtgc   1140
aaatcagatc gttctgtaga acttattctg gattacagca cataaccttt taatatggca   1200
```

-continued

```
tatatcattg cccatgagat gggtcatagt ctgggcatgt tacatgacac aaaattctgt    1260
acttgtgggg ctaaaccatg cattatgttt ggcaaagaaa gcattccacc gcccaaagaa    1320
ttcagcagtt gtagttatga ccagtataac aagtatcttc ttaaatataa cccaaaatgc    1380
attcttgatc cacctttgcg taaagatatt gcttcacctg cagtttgtgg caatgaaatt    1440
tgggaggaag gtgaagaatg tgattgtggt tctcctgcag attgtcgcaa tccatgctgt    1500
gatgctgcaa catgtaaact gaaaccaggg gcagaatgtg gcaatggtga gtgttgtgac    1560
aagtgcaaga ttcgtaaagc aggcacagaa tgccggccag cacgcgatga ctgtgatgtc    1620
gctgaacact gcactggcca atctgctgag tgtccccgta atgagttcca acgcaatggt    1680
caaccatgcc ttaacaactc tggttattgc tacaatgggg attgccccat catgttaaac    1740
caatgtattg ctctctttag tccaagtgca actgtggctc aagattcatg ttttcagcgt    1800
aacttgcaag gcagttacta tggctactgc acaaaggaaa ttggttacta tggtaaacgc    1860
tttccatgtg caccacaaga tgtaaaatgt ggccgtttat actgcttaga taattcattc    1920
aaaaaaaata tgcgttgcaa gaacgactat tcatacgcgg atgaaaataa gggtatcgtt    1980
gaacctggta caaaatgtga agatggtaag gtctgcatca accgcaagtg tgttgatgtg    2040
aatacagcct accatcacca tcaccatcac tag                                 2073
```

<210> SEQ ID NO 50
<211> LENGTH: 689
<212> TYPE: PRT
<213> ORGANISM: Artificial Sequence
<220> FEATURE:
<223> OTHER INFORMATION: Construct pTAP537/526, alpha Fpp
      leader-pro-GPR-Metalloprotease-Disintegrin-Cys rich-His tag

<400> SEQUENCE: 50

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Cys Ser Ile Ile Leu Gly Ser Gly Asn Val Asn
                85                  90                  95

Asp Tyr Glu Val Val Tyr Pro Gln Lys Val Thr Ala Leu Pro Lys Gly
            100                 105                 110

Ala Val Gln Gln Pro Glu Gln Lys Tyr Glu Asp Ala Met Gln Tyr Glu
        115                 120                 125

Phe Glu Val Lys Gly Glu Pro Val Val Leu His Leu Glu Lys Asn Lys
    130                 135                 140

Glu Leu Phe Ser Glu Asp Tyr Ser Glu Thr His Tyr Ser Ser Asp Asp
145                 150                 155                 160

Arg Glu Ile Thr Thr Asn Pro Ser Val Glu Asp His Cys Tyr Tyr His
                165                 170                 175

Gly Arg Ile Gln Asn Asp Ala Glu Ser Thr Ala Ser Ile Ser Ala Cys
            180                 185                 190

Asn Gly Leu Lys Gly His Phe Lys Leu Arg Gly Glu Thr Tyr Phe Ile
        195                 200                 205
```

```
Glu Pro Leu Lys Ile Pro Asp Ser Glu Ala His Ala Val Tyr Lys Tyr
    210                 215                 220
Glu Asn Ile Glu Asn Glu Asp Glu Ala Pro Lys Met Cys Gly Val Thr
225                 230                 235                 240
Gln Asp Asn Trp Glu Ser Asp Glu Pro Ile Lys Lys Thr Leu Gly Pro
                245                 250                 255
Arg Val Pro Pro His Glu Arg Lys Phe Glu Lys Lys Phe Ile Glu Leu
            260                 265                 270
Val Val Val Val Asp His Ser Met Val Thr Lys Tyr Asn Asn Asp Ser
        275                 280                 285
Thr Ala Ile Arg Thr Trp Ile Tyr Glu Met Leu Asn Thr Val Asn Glu
    290                 295                 300
Ile Tyr Leu Pro Phe Asn Ile Arg Val Ala Leu Val Gly Leu Glu Phe
305                 310                 315                 320
Trp Cys Asn Gly Asp Leu Ile Asn Val Thr Ser Thr Ala Asp Asp Thr
                325                 330                 335
Leu His Ser Phe Gly Glu Trp Arg Ala Ser Asp Leu Leu Asn Arg Lys
            340                 345                 350
Arg His Asp His Ala Gln Leu Leu Thr Asn Val Thr Leu Asp His Ser
        355                 360                 365
Thr Leu Gly Ile Thr Phe Val Tyr Gly Met Cys Lys Ser Asp Arg Ser
    370                 375                 380
Val Glu Leu Ile Leu Asp Tyr Ser Asn Ile Thr Phe Asn Met Ala Tyr
385                 390                 395                 400
Ile Ile Ala His Glu Met Gly His Ser Leu Gly Met Leu His Asp Thr
                405                 410                 415
Lys Phe Cys Thr Cys Gly Ala Lys Pro Cys Ile Met Phe Gly Lys Glu
            420                 425                 430
Ser Ile Pro Pro Lys Glu Phe Ser Ser Cys Ser Tyr Asp Gln Tyr
        435                 440                 445
Asn Lys Tyr Leu Leu Lys Tyr Asn Pro Lys Cys Ile Leu Asp Pro Pro
450                 455                 460
Leu Arg Lys Asp Ile Ala Ser Pro Ala Val Cys Gly Asn Glu Ile Trp
465                 470                 475                 480
Glu Glu Gly Glu Glu Cys Asp Cys Gly Ser Pro Ala Asp Cys Arg Asn
                485                 490                 495
Pro Cys Cys Asp Ala Ala Thr Cys Lys Leu Lys Pro Gly Ala Glu Cys
            500                 505                 510
Gly Asn Gly Glu Cys Cys Asp Lys Cys Lys Ile Arg Lys Ala Gly Thr
        515                 520                 525
Glu Cys Arg Pro Ala Arg Asp Asp Cys Asp Val Ala Glu His Cys Thr
    530                 535                 540
Gly Gln Ser Ala Glu Cys Pro Arg Asn Glu Phe Gln Arg Asn Gly Gln
545                 550                 555                 560
Pro Cys Leu Asn Asn Ser Gly Tyr Cys Tyr Asn Gly Asp Cys Pro Ile
                565                 570                 575
Met Leu Asn Gln Cys Ile Ala Leu Phe Ser Pro Ser Ala Thr Val Ala
            580                 585                 590
Gln Asp Ser Cys Phe Gln Arg Asn Leu Gln Gly Ser Tyr Tyr Gly Tyr
        595                 600                 605
Cys Thr Lys Glu Ile Gly Tyr Tyr Gly Lys Arg Phe Pro Cys Ala Pro
    610                 615                 620
```

```
Gln Asp Val Lys Cys Gly Arg Leu Tyr Cys Leu Asp Asn Ser Phe Lys
625                 630                 635                 640

Lys Asn Met Arg Cys Lys Asn Asp Tyr Ser Tyr Ala Asp Glu Asn Lys
            645                 650                 655

Gly Ile Val Glu Pro Gly Thr Lys Cys Glu Asp Gly Lys Val Cys Ile
        660                 665                 670

Asn Arg Lys Cys Val Asp Val Asn Thr Ala Tyr His His His His His
        675                 680                 685

His
```

<210> SEQ ID NO 51
<211> LENGTH: 1317
<212> TYPE: DNA
<213> ORGANISM: Artificial Sequence
<220> FEATURE:
<223> OTHER INFORMATION: Construct pTAP538, met-TLGLI-Metalloprotease-
      Disintegrin-Cys rich-His tag

<400> SEQUENCE: 51

```
atgactttgg ggttaattgt tcctcctcat gaacgaaaat ttgagaaaaa attcattgag      60
cttgtcgtag ttgtggacca cagtatggtc acaaaataca acaatgattc aactgctatc     120
cgcacatgga tctatgaaat gctcaacact gtaaatgaga tctacttacc tttcaatatt     180
cgtgtagcac tggttggcct agaattttgg tgcaatggtg acttgattaa cgtgacatcc     240
acagcagatg atactttgca ctcatttggc gaatggcgcg catcagattt gctgaatcgt     300
aaacgccatg atcatgctca gttactcacg aacgtgacac tggatcattc cactcttggt     360
atcacgttcg tatatggcat gtgcaaatca gatcgttctg tagaacttat tctggattac     420
agcaacataa ctttttaatat ggcatatatc attgcccatg agatgggtca tagtctgggc     480
atgttacatg acacaaaatt ctgtacttgt ggggctaaac catgcattat gtttggcaaa     540
gaaagcattc accgcccaa gaattcagc agttgtagtt atgaccagta taacaagtat      600
cttcttaaat ataacccaaa atgcattctt gatccacctt gcgtaaaga tattgcttca     660
cctgcagttt gtggcaatga aatttgggag gaaggtgaag aatgtgattg tggttctcct     720
gcagattgtc gcaatccatg ctgtgatgct gcaacatgta aactgaaacc aggggcagaa     780
tgtggcaatg gtgagtgttg tgacaagtgc aagattcgta agcaggcac agaatgccgg     840
ccagcacgcg atgactgtga tgtcgctgaa cactgcactg gccaatctgc tgagtgtccc     900
cgtaatgagt tccaacgcaa tggtcaacca tgccttaaca actctggtta ttgctacaat     960
ggggattgcc ccatcatgtt aaaccaatgt attgctctct ttagtccaag tgcaactgtg    1020
gctcaagatt catgttttca gcgtaacttg caaggcagtt actatggcta ctgcacaaag    1080
gaaattggtt actatggtaa acgcttcca tgtgcaccac aagatgtaaa atgtggccgt    1140
ttatactgct tagataattc attcaaaaaa aatatgcgtt gcaagaacga ctattcatac    1200
gcggatgaaa ataagggtat cgttgaacct ggtacaaaat gtgaagatgg taaggtctgc    1260
atcaaccgca agtgtgttga tgtgaataca gcctaccatc accatcacca tcactaa      1317
```

<210> SEQ ID NO 52
<211> LENGTH: 438
<212> TYPE: PRT
<213> ORGANISM: Artificial Sequence
<220> FEATURE:
<223> OTHER INFORMATION: Construct pTAP538, met-TLGLI-Metalloprotease-
      Disintegrin-Cys rich-His tag

<400> SEQUENCE: 52

```
Met Thr Leu Gly Leu Ile Val Pro Pro His Glu Arg Lys Phe Glu Lys
1               5                   10                  15

Lys Phe Ile Glu Leu Val Val Val Asp His Ser Met Val Thr Lys
            20                  25                  30

Tyr Asn Asn Asp Ser Thr Ala Ile Arg Thr Trp Ile Tyr Glu Met Leu
        35                  40                  45

Asn Thr Val Asn Glu Ile Tyr Leu Pro Phe Asn Ile Arg Val Ala Leu
    50                  55                  60

Val Gly Leu Glu Phe Trp Cys Asn Gly Asp Leu Ile Asn Val Thr Ser
65                  70                  75                  80

Thr Ala Asp Asp Thr Leu His Ser Phe Gly Gly Trp Arg Ala Ser Asp
                85                  90                  95

Leu Leu Asn Arg Lys Arg His Asp His Ala Gln Leu Leu Thr Asn Val
            100                 105                 110

Thr Leu Asp His Ser Thr Leu Gly Ile Thr Phe Val Tyr Gly Met Cys
        115                 120                 125

Lys Ser Asp Arg Ser Val Glu Leu Ile Leu Asp Tyr Ser Asn Ile Thr
    130                 135                 140

Phe Asn Met Ala Tyr Ile Ile Ala His Glu Met Gly His Ser Leu Gly
145                 150                 155                 160

Met Leu His Asp Thr Lys Phe Cys Thr Cys Gly Ala Lys Pro Cys Ile
                165                 170                 175

Met Phe Gly Lys Glu Ser Ile Pro Pro Lys Glu Phe Ser Ser Cys
            180                 185                 190

Ser Tyr Asp Gln Tyr Asn Lys Tyr Leu Leu Lys Tyr Asn Pro Lys Cys
    195                 200                 205

Ile Leu Asp Pro Pro Leu Arg Lys Asp Ile Ala Ser Pro Ala Val Cys
    210                 215                 220

Gly Asn Glu Ile Trp Glu Gly Gly Glu Cys Asp Cys Gly Ser Pro
225                 230                 235                 240

Ala Asp Cys Arg Asn Pro Cys Cys Asp Ala Ala Thr Cys Lys Leu Lys
            245                 250                 255

Pro Gly Ala Glu Cys Gly Asn Gly Glu Cys Cys Asp Lys Cys Lys Ile
            260                 265                 270

Arg Lys Ala Gly Thr Glu Cys Arg Pro Ala Arg Asp Asp Cys Asp Val
    275                 280                 285

Ala Glu His Cys Thr Gly Gln Ser Ala Glu Cys Pro Arg Asn Glu Phe
    290                 295                 300

Gln Arg Asn Gly Gln Pro Cys Leu Asn Asn Ser Gly Tyr Cys Tyr Asn
305                 310                 315                 320

Gly Asp Cys Pro Ile Met Leu Asn Gln Cys Ile Ala Leu Phe Ser Pro
            325                 330                 335

Ser Ala Thr Val Ala Gln Asp Ser Cys Phe Gln Arg Asn Leu Gln Gly
            340                 345                 350

Ser Tyr Tyr Gly Tyr Cys Thr Lys Glu Ile Gly Tyr Tyr Gly Lys Arg
    355                 360                 365

Phe Pro Cys Ala Pro Gln Asp Val Lys Cys Gly Arg Leu Tyr Cys Leu
    370                 375                 380

Asp Asn Ser Phe Lys Lys Asn Met Arg Cys Lys Asn Asp Tyr Ser Tyr
385                 390                 395                 400

Ala Asp Glu Asn Lys Gly Ile Val Glu Pro Gly Thr Lys Cys Glu Asp
                405                 410                 415
```

-continued

Gly Lys Val Cys Ile Asn Arg Lys Cys Val Asp Val Asn Thr Ala Tyr
            420                 425                 430

His His His His His His
        435

<210> SEQ ID NO 53
<211> LENGTH: 1302
<212> TYPE: DNA
<213> ORGANISM: Artificial Sequence
<220> FEATURE:
<223> OTHER INFORMATION: Construct pTAP539, met-Metalloprotease-
      Disintegrin-Cys rich-His tag

<400> SEQUENCE: 53

```
atggttcctc ctcatgaacg aaaatttgag aaaaaattca ttgagcttgt cgtagttgtg      60
gaccacagta tggtcacaaa atacaacaat gattcaactg ctatccgcac atggatctat     120
gaaatgctca cactgtaaa tgagatctac ttacctttca atattcgtgt agcactggtt      180
ggcctagaat tttggtgcaa tggtgacttg attaacgtga catccacagc agatgatact     240
ttgcactcat ttggcgaatg gcgcgcatca gatttgctga atcgtaaacg ccatgatcat     300
gctcagttac tcacgaacgt gacactggat cattccactc ttggtatcac gttcgtatat     360
ggcatgtgca atcagatcg ttctgtagaa cttattctgg attacagcaa cataactttt      420
aatatggcat atatcattgc ccatgagatg ggtcatagtc tgggcatgtt acatgacaca     480
aaattctgta cttgtggggc taaccatgc attatgtttg gcaaagaaag cattccaccg      540
cccaaagaat tcagcagttg tagttatgac cagtataaca agtatcttct taaatataac     600
ccaaaatgca ttcttgatcc accttttgcgt aaagatattg cttcacctgc agtttgtggc    660
aatgaaattt gggaggaagg tgaagaatgt gattgtggtt ctcctgcaga ttgtcgcaat     720
ccatgctgtg atgctgcaac atgtaaactg aaaccagggg cagaatgtgg caatggtgag     780
tgttgtgaca gtgcaagat cgtaaagca ggcacagaat gccggccagc acgcgatgac       840
tgtgatgtcg ctgaacactg cactggccaa tctgctgagt gtccccgtaa tgagttccaa     900
cgcaatggtc aaccatgcct taacaactct ggttattgct acaatgggga ttgccccatc     960
atgttaaacc aatgtattgc tctctttagt ccaagtgcaa ctgtggctca agattcatgt    1020
tttcagcgta acttgcaagg cagttactat ggctactgca caaaggaaat tggttactat    1080
ggtaaacgct tccatgtgc accacaagat gtaaaatgtg ccgtttata ctgcttagat      1140
aattcattca aaaaaatat gcgttgcaag aacgactatt catacgcgga tgaaaataag    1200
ggtatcgttg aacctggtac aaaatgtgaa gatggtaagg tctgcatcaa ccgcaagtgt    1260
gttgatgtga atacagccta ccatcaccat caccatcact aa                       1302
```

<210> SEQ ID NO 54
<211> LENGTH: 433
<212> TYPE: PRT
<213> ORGANISM: Artificial Sequence
<220> FEATURE:
<223> OTHER INFORMATION: Construct pTAP539, met-Metalloprotease-
      Disintegrin-Cys rich-His tag

<400> SEQUENCE: 54

Met Val Pro Pro His Glu Arg Lys Phe Glu Lys Phe Ile Glu Leu
1               5                   10                  15

Val Val Val Asp His Ser Met Val Thr Lys Tyr Asn Asn Asp Ser
            20                  25                  30

Thr Ala Ile Arg Thr Trp Ile Tyr Glu Met Leu Asn Thr Val Asn Glu

```
            35                  40                  45
Ile Tyr Leu Pro Phe Asn Ile Arg Val Ala Leu Val Gly Leu Glu Phe
 50                  55                  60

Trp Cys Asn Gly Asp Leu Ile Asn Val Thr Ser Thr Ala Asp Asp Thr
 65                  70                  75                  80

Leu His Ser Phe Gly Glu Trp Arg Ala Ser Asp Leu Leu Asn Arg Lys
                 85                  90                  95

Arg His Asp His Ala Gln Leu Leu Thr Asn Val Thr Leu Asp His Ser
            100                 105                 110

Thr Leu Gly Ile Thr Phe Val Tyr Gly Met Cys Lys Ser Asp Arg Ser
        115                 120                 125

Val Glu Leu Ile Leu Asp Tyr Ser Asn Ile Thr Phe Asn Met Ala Tyr
    130                 135                 140

Ile Ile Ala His Glu Met Gly His Ser Leu Gly Met Leu His Asp Thr
145                 150                 155                 160

Lys Phe Cys Thr Cys Gly Ala Lys Pro Cys Ile Met Phe Gly Lys Glu
                165                 170                 175

Ser Ile Pro Pro Lys Glu Phe Ser Ser Cys Ser Tyr Asp Gln Tyr
            180                 185                 190

Asn Lys Tyr Leu Leu Lys Tyr Asn Pro Lys Cys Ile Leu Asp Pro Pro
        195                 200                 205

Leu Arg Lys Asp Ile Ala Ser Pro Ala Val Cys Gly Asn Glu Ile Trp
    210                 215                 220

Glu Glu Gly Glu Glu Cys Asp Cys Gly Ser Pro Ala Asp Cys Arg Asn
225                 230                 235                 240

Pro Cys Cys Asp Ala Ala Thr Cys Lys Leu Lys Pro Gly Ala Glu Cys
                245                 250                 255

Gly Asn Gly Glu Cys Cys Asp Lys Cys Lys Ile Arg Lys Ala Gly Thr
            260                 265                 270

Glu Cys Arg Pro Ala Arg Asp Asp Cys Asp Val Ala Glu His Cys Thr
        275                 280                 285

Gly Gln Ser Ala Glu Cys Pro Arg Asn Glu Phe Gln Arg Asn Gly Gln
    290                 295                 300

Pro Cys Leu Asn Asn Ser Gly Tyr Cys Tyr Asn Gly Asp Cys Pro Ile
305                 310                 315                 320

Met Leu Asn Gln Cys Ile Ala Leu Phe Ser Pro Ser Ala Thr Val Ala
                325                 330                 335

Gln Asp Ser Cys Phe Gln Arg Asn Leu Gln Gly Ser Tyr Tyr Gly Tyr
            340                 345                 350

Cys Thr Lys Glu Ile Gly Tyr Tyr Gly Lys Arg Phe Pro Cys Ala Pro
        355                 360                 365

Gln Asp Val Lys Cys Gly Arg Leu Tyr Cys Leu Asp Asn Ser Phe Lys
    370                 375                 380

Lys Asn Met Arg Cys Lys Asn Asp Tyr Ser Tyr Ala Asp Glu Asn Lys
385                 390                 395                 400

Gly Ile Val Glu Pro Gly Thr Lys Cys Glu Asp Gly Lys Val Cys Ile
                405                 410                 415

Asn Arg Lys Cys Val Asp Val Asn Thr Ala Tyr His His His His
            420                 425                 430

His

<210> SEQ ID NO 55
<211> LENGTH: 1455
```

<210> SEQ ID NO 55
<211> LENGTH: 1455
<212> TYPE: DNA
<213> ORGANISM: Artificial Sequence
<220> FEATURE:
<223> OTHER INFORMATION: Construct pTAP553, met-pro-Metalloprotease-Disintegrin-His tag

<400> SEQUENCE: 55

```
atgggttgct ctataatcct gggatctggg aatgttaatg attatgaagt agtgtatcca      60
caaaaagtca ctgcattgcc caaaggagca gttcagcagc tgagcaaaa gtatgaagat     120
gccatgcaat atgaatttga agtgaaggga gagccagtgg tccttcacct agaaaaaaat     180
aaagaacttt tttcagaaga ttacagtgag actcattatt cgtctgatga cagagaaatt     240
acaacaaacc cttcagttga ggatcactgc tattatcatg gacggatcca gaatgatgct     300
gagtcaactg caagcatcag tgcatgcaat ggtttgaaag acatttcaa gcttcgaggg     360
gagacgtact ttattgaacc cttgaagatt cccgacagtg aagcccatgc agtctacaaa     420
tatgaaaaca tagaaaatga ggatgaagcc cccaaaatgt gtgggtaac ccaggataat     480
tgggaatcag atgaacccat caaaaagact ttggggccaa gagttcctcc tcatgaacga     540
aaatttgaga aaaaattcat tgagcttgtc gtagttgtgg accacagtat ggtcacaaaa     600
tacaacaatg attcaactgc tatccgcaca tggatctatg aaatgctcaa cactgtaaat     660
gagatctact acctttcaa tattcgtgta gcactggttg cctagaatt ttggtgcaat     720
ggtgacttga ttaacgtgac atccacagca gatgatactt tgcactcatt tggcgaatgg     780
cgcgcatcag atttgctgaa tcgtaaacgc catgatcatg ctcagttact cacgaacgtg     840
acactggatc attccactct tggtatcacg ttcgtatatg catgtgcaa atcagatcgt     900
tctgtagaac ttattctgga ttacagcaac ataactttta atatggcata tcattgcc     960
catgagatgg gtcatagtct gggcatgtta catgacacaa aattctgtac ttgtgggct    1020
aaaccatgca ttatgtttgg caagaaagc attccaccgc ccaagaatt cagcagttgt    1080
agttatgacc agtataacaa gtatcttctt aaatataacc aaaatgcat tcttgatcca    1140
cctttgcgta agatattgc ttcacctgca gtttgtggca atgaaatttg ggaggaaggt    1200
gaagaatgtg attgtggttc tcctgcagat tgtcgcaatc catgctgtga tgctgcaaca    1260
tgtaaactga accaggggc agaatgtggc aatggtgagt gttgtgacaa gtgcaagatt    1320
cgtaaagcag gcacagaatg ccggccagca cgcgatgact gtgatgtcgc tgaacactgc    1380
actggccaat ctgctgagtg tccccgtaat gagttccaac gcaatggtca accacatcac    1440
catcaccatc actag                                                    1455
```

<210> SEQ ID NO 56
<211> LENGTH: 483
<212> TYPE: PRT
<213> ORGANISM: Artificial Sequence
<220> FEATURE:
<223> OTHER INFORMATION: Construct pTAP553, met-pro-Metalloprotease-Disintegrin-His tag
<220> FEATURE:
<221> NAME/KEY: PROPEP
<222> LOCATION: (1)..(483)

<400> SEQUENCE: 56

Met Cys Ser Ile Ile Leu Gly Ser Gly Asn Val Asn Asp Tyr Glu Val
1               5                   10                  15

Val Tyr Pro Gln Lys Val Thr Ala Leu Pro Lys Gly Ala Val Gln Gln
            20                  25                  30

Pro Glu Gln Lys Tyr Glu Asp Ala Met Gln Tyr Glu Phe Glu Val Lys

```
                35                  40                  45
Gly Glu Pro Val Val Leu His Leu Glu Lys Asn Lys Glu Leu Phe Ser
 50                  55                  60

Glu Asp Tyr Ser Glu Thr His Tyr Ser Ser Asp Arg Glu Ile Thr
 65                  70                  75                  80

Thr Asn Pro Ser Val Glu Asp His Cys Tyr Tyr His Gly Arg Ile Gln
                 85                  90                  95

Asn Asp Ala Glu Ser Thr Ala Ser Ile Ser Ala Cys Asn Gly Leu Lys
                100                 105                 110

Gly His Phe Lys Leu Arg Gly Glu Thr Tyr Phe Ile Glu Pro Leu Lys
            115                 120                 125

Ile Pro Asp Ser Glu Ala His Ala Val Tyr Lys Tyr Glu Asn Ile Glu
        130                 135                 140

Asn Glu Asp Glu Ala Pro Lys Met Cys Gly Val Thr Gln Asp Asn Trp
145                 150                 155                 160

Glu Ser Asp Glu Pro Ile Lys Lys Thr Leu Gly Pro Arg Val Pro Pro
                165                 170                 175

His Glu Arg Lys Phe Glu Lys Lys Phe Ile Glu Leu Val Val Val Val
            180                 185                 190

Asp His Ser Met Val Thr Lys Tyr Asn Asn Asp Ser Thr Ala Ile Arg
        195                 200                 205

Thr Trp Ile Tyr Glu Met Leu Asn Thr Val Asn Glu Ile Tyr Leu Pro
210                 215                 220

Phe Asn Ile Arg Val Ala Leu Val Gly Leu Glu Phe Trp Cys Asn Gly
225                 230                 235                 240

Asp Leu Ile Asn Val Thr Ser Thr Ala Asp Asp Thr Leu His Ser Phe
                245                 250                 255

Gly Glu Trp Arg Ala Ser Asp Leu Leu Asn Arg Lys Arg His Asp His
            260                 265                 270

Ala Gln Leu Leu Thr Asn Val Thr Leu Asp His Ser Thr Leu Gly Ile
        275                 280                 285

Thr Phe Val Tyr Gly Met Cys Lys Ser Asp Arg Ser Val Glu Leu Ile
290                 295                 300

Leu Asp Tyr Ser Asn Ile Thr Phe Asn Met Ala Tyr Ile Ile Ala His
305                 310                 315                 320

Glu Met Gly His Ser Leu Gly Met Leu His Asp Thr Lys Phe Cys Thr
                325                 330                 335

Cys Gly Ala Lys Pro Cys Ile Met Phe Gly Lys Glu Ser Ile Pro Pro
            340                 345                 350

Pro Lys Glu Phe Ser Ser Cys Ser Tyr Asp Gln Tyr Asn Lys Tyr Leu
        355                 360                 365

Leu Lys Tyr Asn Pro Lys Cys Ile Leu Asp Pro Leu Arg Lys Asp
            370                 375                 380

Ile Ala Ser Pro Ala Val Cys Gly Asn Glu Ile Trp Glu Glu Gly Glu
385                 390                 395                 400

Glu Cys Asp Cys Gly Ser Pro Ala Asp Cys Arg Asn Pro Cys Cys Asp
                405                 410                 415

Ala Ala Thr Cys Lys Leu Lys Pro Gly Ala Glu Cys Gly Asn Gly Glu
            420                 425                 430

Cys Cys Asp Lys Cys Lys Ile Arg Lys Ala Gly Thr Glu Cys Arg Pro
        435                 440                 445

Ala Arg Asp Asp Cys Asp Val Ala Glu His Cys Thr Gly Gln Ser Ala
450                 455                 460
```

```
Glu Cys Pro Arg Asn Glu Phe Gln Arg Asn Gly Gln Pro His His His
465                 470                 475                 480

His His His
```

<210> SEQ ID NO 57
<211> LENGTH: 60
<212> TYPE: DNA
<213> ORGANISM: Artificial Sequence
<220> FEATURE:
<223> OTHER INFORMATION: Oligo number ZC56902, Oligonucleotide Primer

<400> SEQUENCE: 57

```
tctatgttcg tttttctat tgctacaaac gcgtatgcag ttcctcctca tgaacgaaaa        60
```

<210> SEQ ID NO 58
<211> LENGTH: 61
<212> TYPE: DNA
<213> ORGANISM: Artificial Sequence
<220> FEATURE:
<223> OTHER INFORMATION: Oligo number ZC57098, Oligonucleotide Primer
      Member

<400> SEQUENCE: 58

```
caggaaatcc atgccgagtt gagacgcttc cgtagatcta ctttggggtt aattgttcct        60
c                                                                        61
```

<210> SEQ ID NO 59
<211> LENGTH: 59
<212> TYPE: DNA
<213> ORGANISM: Artificial Sequence
<220> FEATURE:
<223> OTHER INFORMATION: Oligo number ZC57099, Oligonucleotide Primer
      Member (3')

<400> SEQUENCE: 59

```
acaaccccag agctgtttta aggcgcgcct ctagattagt aggctgtatt cacatcaac         59
```

<210> SEQ ID NO 60
<211> LENGTH: 70
<212> TYPE: DNA
<213> ORGANISM: Artificial Sequence
<220> FEATURE:
<223> OTHER INFORMATION: Oligo number ZC56869, oligonucleotide primer

<400> SEQUENCE: 60

```
actttggggt taattgttcc tcctcatgaa cgaaatttg agaaaaaatt cattgagctt        60
gtcgtagttg                                                                70
```

<210> SEQ ID NO 61
<211> LENGTH: 83
<212> TYPE: DNA
<213> ORGANISM: Artificial Sequence
<220> FEATURE:
<223> OTHER INFORMATION: Oligo number ZC56870, oligonucleotide primer

<400> SEQUENCE: 61

```
caatgattca actgctatcc gcacatggat ctatgaaatg ctcaacactg taaatgagat        60
ctacttacct ttcaatattc gtg                                                83
```

<210> SEQ ID NO 62
<211> LENGTH: 75
<212> TYPE: DNA
<213> ORGANISM: Artificial Sequence

```
<220> FEATURE:
<223> OTHER INFORMATION: Oligo number ZC56871, oligonucleotide primer

<400> SEQUENCE: 62
gattaacgtg acatccacag cagatgatac tttgcactca tttggcgaat ggcgcgcatc     60
agatttgctg aatcg                                                     75

<210> SEQ ID NO 63
<211> LENGTH: 73
<212> TYPE: DNA
<213> ORGANISM: Artificial Sequence
<220> FEATURE:
<223> OTHER INFORMATION: Oligo number ZC56872, oligonucleotide primer

<400> SEQUENCE: 63
aacgtgacac tggatcattc cactcttggt atcacgttcg tatatggcat gtgcaaatca     60
gatcgttctg tag                                                       73

<210> SEQ ID NO 64
<211> LENGTH: 78
<212> TYPE: DNA
<213> ORGANISM: Artificial Sequence
<220> FEATURE:
<223> OTHER INFORMATION: Oligo number ZC56873, oligonucleotide primer

<400> SEQUENCE: 64
catatatcat tgcccatgag atgggtcata gtctgggcat gttacatgac acaaaattct     60
gtacttgtgg ggctaaac                                                  78

<210> SEQ ID NO 65
<211> LENGTH: 90
<212> TYPE: DNA
<213> ORGANISM: Artificial Sequence
<220> FEATURE:
<223> OTHER INFORMATION: Oligo number ZC56874, oligonucleotide primer

<400> SEQUENCE: 65
cagcagttgt agttatgacc agtataacaa gtatcttctt aaatataacc caaaatgcat     60
tcttgatcca cctttgcgta aagatattgc                                     90

<210> SEQ ID NO 66
<211> LENGTH: 79
<212> TYPE: DNA
<213> ORGANISM: Artificial Sequence
<220> FEATURE:
<223> OTHER INFORMATION: Oligo number ZC56875, oligonucleotide primer

<400> SEQUENCE: 66
ggaggaaggt gaagaatgtg attgtggttc tcctgcagat tgtcgcaatc catgctgtga     60
tgctgcaaca tgtaaactg                                                 79

<210> SEQ ID NO 67
<211> LENGTH: 75
<212> TYPE: DNA
<213> ORGANISM: Artificial Sequence
<220> FEATURE:
<223> OTHER INFORMATION: Oligo number ZC56876, oligonucleotide primer

<400> SEQUENCE: 67
gtgcaagatt cgtaaagcag gcacagaatg ccggccagca cgcgatgact gtgatgtcgc     60
tgaacactgc actgg                                                     75
```

<210> SEQ ID NO 68
<211> LENGTH: 82
<212> TYPE: DNA
<213> ORGANISM: Artificial Sequence
<220> FEATURE:
<223> OTHER INFORMATION: Oligo number ZC56883, oligonucleotide primer

<400> SEQUENCE: 68
gtcaaccatg ccttaacaac tctggttatt gctacaatgg ggattgcccc atcatgttaa    60
accaatgtat tgctctcttt ag    82

<210> SEQ ID NO 69
<211> LENGTH: 85
<212> TYPE: DNA
<213> ORGANISM: Artificial Sequence
<220> FEATURE:
<223> OTHER INFORMATION: Oligo number ZC56884, oligonucleotide primer

<400> SEQUENCE: 69
cagcgtaact tgcaaggcag ttactatggc tactgcacaa aggaaattgg ttactatggt    60
aaacgctttc catgtgcacc acaag    85

<210> SEQ ID NO 70
<211> LENGTH: 88
<212> TYPE: DNA
<213> ORGANISM: Artificial Sequence
<220> FEATURE:
<223> OTHER INFORMATION: Oligo number ZC56885, oligonucleotide primer

<400> SEQUENCE: 70
gcaagaacga ctattcatac gcggatgaaa ataagggtat cgttgaacct ggtacaaaat    60
gtgaagatgg taaggtctgc atcaaccg    88

<210> SEQ ID NO 71
<211> LENGTH: 51
<212> TYPE: DNA
<213> ORGANISM: Artificial Sequence
<220> FEATURE:
<223> OTHER INFORMATION: Oligo number ZC56886, oligonucleotide primer

<400> SEQUENCE: 71
ttagtaggct gtattcacat caacacactt gcggttgatg cagaccttac c    51

<210> SEQ ID NO 72
<211> LENGTH: 98
<212> TYPE: DNA
<213> ORGANISM: Artificial Sequence
<220> FEATURE:
<223> OTHER INFORMATION: Oligo number ZC56887, oligonucleotide primer

<400> SEQUENCE: 72
cgtatgaata gtcgttcttg caacgcatat ttttttgaa tgaattatct aagcagtata    60
aacggccaca ttttacatct tgtggtgcac atggaaag    98

<210> SEQ ID NO 73
<211> LENGTH: 75
<212> TYPE: DNA
<213> ORGANISM: Artificial Sequence
<220> FEATURE:
<223> OTHER INFORMATION: Oligo number ZC56888, oligonucleotide primer

<400> SEQUENCE: 73
ctgccttgca agttacgctg aaaacatgaa tcttgagcca cagttgcact tggactaaag    60
agagcaatac attgg 75

<210> SEQ ID NO 74
<211> LENGTH: 80
<212> TYPE: DNA
<213> ORGANISM: Artificial Sequence
<220> FEATURE:
<223> OTHER INFORMATION: Oligo number ZC56889, oligonucleotide primer

<400> SEQUENCE: 74
gttgttaagg catggttgac cattgcgttg gaactcatta cggggacact cagcagattg 60
gccagtgcag tgttcagcga 80

<210> SEQ ID NO 75
<211> LENGTH: 82
<212> TYPE: DNA
<213> ORGANISM: Artificial Sequence
<220> FEATURE:
<223> OTHER INFORMATION: Oligo number ZC56890, oligonucleotide primer

<400> SEQUENCE: 75
ctgctttacg aatcttgcac ttgtcacaac actcaccatt gccacattct gcccctggtt 60
tcagtttaca tgttgcagca tc 82

<210> SEQ ID NO 76
<211> LENGTH: 74
<212> TYPE: DNA
<213> ORGANISM: Artificial Sequence
<220> FEATURE:
<223> OTHER INFORMATION: Oligo number ZC56891, oligonucleotide primer

<400> SEQUENCE: 76
caatcacatt cttcacctt ctcccaaatt tcattgccac aaactgcagg tgaagcaata 60
tctttacgca aagg 74

<210> SEQ ID NO 77
<211> LENGTH: 86
<212> TYPE: DNA
<213> ORGANISM: Artificial Sequence
<220> FEATURE:
<223> OTHER INFORMATION: Oligo number ZC56892, oligonucleotide primer

<400> SEQUENCE: 77
ggtcataact acaactgctg aattctttgg gcggtggaat gctttctttg ccaaacataa 60
tgcatggttt agccccacaa gtacag 86

<210> SEQ ID NO 78
<211> LENGTH: 80
<212> TYPE: DNA
<213> ORGANISM: Artificial Sequence
<220> FEATURE:
<223> OTHER INFORMATION: Oligo number ZC56893, oligonucleotide primer

<400> SEQUENCE: 78
ctcatgggca atgatatatg ccatattaaa agttatgttg ctgtaatcca gaataagttc 60
tacagaacga tctgatttgc 80

<210> SEQ ID NO 79
<211> LENGTH: 78
<212> TYPE: DNA
<213> ORGANISM: Artificial Sequence
<220> FEATURE:

-continued

<223> OTHER INFORMATION: Oligo number ZC56894, oligonucleotide primer

<400> SEQUENCE: 79
gaatgatcca gtgtcacgtt cgtgagtaac tgagcatgat catggcgttt acgattcagc    60
aaatctgatg cgcgccat    78

<210> SEQ ID NO 80
<211> LENGTH: 80
<212> TYPE: DNA
<213> ORGANISM: Artificial Sequence
<220> FEATURE:
<223> OTHER INFORMATION: Oligo number ZC56895, oligonucleotide primer

<400> SEQUENCE: 80
ctgtggatgt cacgttaatc aagtcaccat tgcaccaaaa ttctaggcca accagtgcta    60
cacgaatatt gaaaggtaag    80

<210> SEQ ID NO 81
<211> LENGTH: 68
<212> TYPE: DNA
<213> ORGANISM: Artificial Sequence
<220> FEATURE:
<223> OTHER INFORMATION: Oligo number ZC56896, oligonucleotide primer

<400> SEQUENCE: 81
ggatagcagt tgaatcattg ttgtattttg tgaccatact gtggtccaca actacgacaa    60
gctcaatg    68

<210> SEQ ID NO 82
<211> LENGTH: 57
<212> TYPE: DNA
<213> ORGANISM: Artificial Sequence
<220> FEATURE:
<223> OTHER INFORMATION: Oligo number ZC57640, oligonucleotide primer

<400> SEQUENCE: 82
aggcgcgcct ctagattagt gatggtgatg gtgatggtag gctgtattca catcaac    57

<210> SEQ ID NO 83
<211> LENGTH: 61
<212> TYPE: DNA
<213> ORGANISM: Artificial Sequence
<220> FEATURE:
<223> OTHER INFORMATION: Oligo number ZC57641, oligonucleotide primer

<400> SEQUENCE: 83
tgggtacaac cccagagctg ttttaaggcg cgcctctaga ttagtgatgg tgatggtgat    60
g    61

<210> SEQ ID NO 84
<211> LENGTH: 60
<212> TYPE: DNA
<213> ORGANISM: Artificial Sequence
<220> FEATURE:
<223> OTHER INFORMATION: Oligo number ZC58220, oligonucleotide primers

<400> SEQUENCE: 84
gcttagcagt ttttccatat caaggttgct ctataatcct gggatctggg aatgttaatg    60

<210> SEQ ID NO 85
<211> LENGTH: 52
<212> TYPE: DNA
<213> ORGANISM: Artificial Sequence

```
<220> FEATURE:
<223> OTHER INFORMATION: Oligo number ZC58221, oligonucleotide primer

<400> SEQUENCE: 85
gtatccacaa aaagtcactg cattgcccaa aggagcagtt cagcagcctg ag          52

<210> SEQ ID NO 86
<211> LENGTH: 79
<212> TYPE: DNA
<213> ORGANISM: Artificial Sequence
<220> FEATURE:
<223> OTHER INFORMATION: Oligo number ZC58222, oligonucleotide primer

<400> SEQUENCE: 86
gaagggagag ccagtggtcc ttcacctaga aaaaaataaa gaactttttt cagaagatta   60
cagtgagact cattattcg                                                79

<210> SEQ ID NO 87
<211> LENGTH: 73
<212> TYPE: DNA
<213> ORGANISM: Artificial Sequence
<220> FEATURE:
<223> OTHER INFORMATION: Oligo number ZC58223, oligonucleotide primer

<400> SEQUENCE: 87
gagaaattac aacaaaccct tcagttgagg atcactgcta ttatcatgga cggatccaga   60
atgatgctga gtc                                                      73

<210> SEQ ID NO 88
<211> LENGTH: 68
<212> TYPE: DNA
<213> ORGANISM: Artificial Sequence
<220> FEATURE:
<223> OTHER INFORMATION: Oligo number ZC58224, oligonucleotide primer

<400> SEQUENCE: 88
gaaaggacat ttcaagcttc gagggagac gtactttatt gaacccttga agattcccga    60
cagtgaag                                                            68

<210> SEQ ID NO 89
<211> LENGTH: 73
<212> TYPE: DNA
<213> ORGANISM: Artificial Sequence
<220> FEATURE:
<223> OTHER INFORMATION: Oligo number ZC58225, oligonucleotide primer

<400> SEQUENCE: 89
gatgaagccc ccaaaatgtg tggggtaacc caggataatt gggaatcaga tgaacccatc   60
aaaaagactt tgg                                                      73

<210> SEQ ID NO 90
<211> LENGTH: 76
<212> TYPE: DNA
<213> ORGANISM: Artificial Sequence
<220> FEATURE:
<223> OTHER INFORMATION: Oligo number ZC58226, oligonucleotide primer

<400> SEQUENCE: 90
gatatggaaa aactgctaag catataatta ccaagagaat ctggatcatt ttggaggctg   60
aatttggctt gaagac                                                   76

<210> SEQ ID NO 91
```

```
<211> LENGTH: 56
<212> TYPE: DNA
<213> ORGANISM: Artificial Sequence
<220> FEATURE:
<223> OTHER INFORMATION: Oligo number ZC58227, oligonucleotide primer

<400> SEQUENCE: 91
gcagtgactt tttgtggata cactacttca taatcattaa cattcccaga tcccag        56

<210> SEQ ID NO 92
<211> LENGTH: 78
<212> TYPE: DNA
<213> ORGANISM: Artificial Sequence
<220> FEATURE:
<223> OTHER INFORMATION: Oligo number ZC58228, oligonucleotide primer

<400> SEQUENCE: 92
ggaccactgg ctctcccttc acttcaaatt catattgcat ggcatcttca tactttgct     60 caggctgctg aactgctc                                                  78

<210> SEQ ID NO 93
<211> LENGTH: 58
<212> TYPE: DNA
<213> ORGANISM: Artificial Sequence
<220> FEATURE:
<223> OTHER INFORMATION: Oligo number ZC58229, oligonucleotide primer

<400> SEQUENCE: 93
ctgaagggtt tgttgtaatt tctctgtcat cagacgaata atgagtctca ctgtaatc      58

<210> SEQ ID NO 94
<211> LENGTH: 72
<212> TYPE: DNA
<213> ORGANISM: Artificial Sequence
<220> FEATURE:
<223> OTHER INFORMATION: Oligo number ZC58242, oligonucleotide primer

<400> SEQUENCE: 94
gaagcttgaa atgtcctttc aaaccattgc atgcactgat gcttgcagtt gactcagcat    60
cattctggat cc                                                        72

<210> SEQ ID NO 95
<211> LENGTH: 78
<212> TYPE: DNA
<213> ORGANISM: Artificial Sequence
<220> FEATURE:
<223> OTHER INFORMATION: Oligo number ZC58243, oligonucleotide primer

<400> SEQUENCE: 95
cacattttgg gggcttcatc ctcattttct atgttttcat atttgtagac tgcatgggct    60
tcactgtcgg gaatcttc                                                  78

<210> SEQ ID NO 96
<211> LENGTH: 66
<212> TYPE: DNA
<213> ORGANISM: Artificial Sequence
<220> FEATURE:
<223> OTHER INFORMATION: Oligo number ZC58244, oligonucleotide primer

<400> SEQUENCE: 96 gaatttttc tcaaattttc gttcatgagg aggaacaatt aaccccaaag tcttttgat      60 gggttc                                                               66
```

```
<210> SEQ ID NO 97
<211> LENGTH: 60
<212> TYPE: DNA
<213> ORGANISM: Artificial Sequence
<220> FEATURE:
<223> OTHER INFORMATION: Oligo number ZC58327, oligonucleotide primer

<400> SEQUENCE: 97 tttttctca aatttcgtt catgaggagg aactcttggc cccaaagtct ttttgatggg    60

<210> SEQ ID NO 98
<211> LENGTH: 59
<212> TYPE: DNA
<213> ORGANISM: Artificial Sequence
<220> FEATURE:
<223> OTHER INFORMATION: Oligo number , oligonucleotide primer

<400> SEQUENCE: 98
tccacaggtg tccagggaat tcatataggc cggccaccat gatccagatt ctcttggta    59

<210> SEQ ID NO 99
<211> LENGTH: 1848
<212> TYPE: DNA
<213> ORGANISM: Echis carinatus

<400> SEQUENCE: 99
atgatccaga ttctcttggt aattatatgc ttagcagttt ttccatatca aggttgctct      60
ataatcctgg gatctgggaa tgttaatgat tatgaagtag tgtatccaca aaaagtcact     120
gcattgccca aggagcagt tcagcagcct gagcaaaagt atgaagatgc catgcaatat     180
gaatttgaag tgaagggaga gccagtggtc cttcacctag aaaaaaataa agaactttt     240 tcagaagatt acagtgagac tcattattcg tctgatgaca gagaaattac aacaaaccct    300
tcagttgagg atcactgcta ttatcatgga cggatccaga tgatgctga gtcaactgca     360 agcatcagtg catgcaatgg tttgaaagga catttcaagc ttcgagggga gacgtacttt    420
attgaaccct tgaagattcc cgacagtgaa gcccatgcag tctacaaata tgaaaacata    480
gaaaatgagg atgaagcccc caaaatgtgt ggggtaaccc aggataattg gaatcagat     540 gaaccatca aaaagacttt ggggttaatt gttcctcctc atgaacgaaa atttgagaaa     600
aaattcattg agcttgtcgt agttgtggac acagtatgg tcacaaaata caacaatgat     660
tcaactgcta taagaacatg gatatatgaa atgctcaaca ctgtaaatga gatatactta    720
cctttcaata ttcgtgtagc actggttggc ctagaattt ggtgcaatgg agacttgatt     780
aacgtgacat ccacagcaga tgatactttg cactcattg gagaatggag agcatcagat    840
ttgctgaatc gaaaaagaca tgatcatgct cagttactca cgaacgtgac actggatcat    900
tccactcttg gaatcacgtt cgtatatggc atgtgcaaat cagatcgttc gtagaactt    960 attctggatt acagcaacat aactttaat atggcatata taatagccca tgagatggt     1020 catagtctgg gcatgttaca tgacacaaaa ttctgtactt gtgggctaa accatgcatt     1080 atgtttggca agaaaagcat tccaccgccc aaagaattca gcagttgtag ttatgaccag    1140
tataacaagt atcttcttaa atataaccca aaatgcattc ttgatccacc tttgagaaaa    1200
gatattgctt cacctgcagt ttgtggaaat gaaatttggg aggaaggaga agaatgtgat    1260
tgtggttctc ctgcagattg tcgaaatcca tgctgtgatg ctgcaacatg taaactgaaa    1320
ccaggggcag aatgtggaaa tggagagtgt tgtgacaagt gcaagattag gaaagcagga    1380
acagaatgcc ggccagcaag ggatgactgt gatgtcgctg aacactgcac tggccaatct    1440
```

-continued

```
gctgagtgtc ccagaaatga gttccaaagg aatggacaac catgccttaa caactcgggt   1500
tattgctaca atggggattg ccccatcatg ttaaaccaat gtattgctct ctttagtcca   1560
agtgcaactg tggctcaaga ttcatgtttt cagaggaact tgcaaggcag ttactatggc   1620
tactgcacaa aggaaattgg ttactatggt aaaaggtttc catgtgcacc acaagatgta   1680
aaatgtggca gattatactg cttagataat tcattcaaaa aaaatatgcg ttgcaagaac   1740
gactattcat acgcggatga aaataaggga atagttgaac ctggaacaaa atgtgaagat   1800
ggaaaggtct gcatcaacag gaagtgtgtt gatgtgaata cagcctac                 1848
```

```

<210> SEQ ID NO 100
<211> LENGTH: 616
<212> TYPE: PRT
<213> ORGANISM: Echis carinatus

<400> SEQUENCE: 100

Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Asp Arg Glu Ile
                85                  90                  95

Thr Thr Asn Pro Ser Val Glu Asp His Cys Tyr Tyr His Gly Arg Ile
            100                 105                 110

Gln Asn Asp Ala Glu Ser Thr Ala Ser Ile Ser Ala Cys Asn Gly Leu
        115                 120                 125

Lys Gly His Phe Lys Leu Arg Gly Glu Thr Tyr Phe Ile Glu Pro Leu
    130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Leu Ile Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
    210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
        275                 280                 285

His Ala Gln Leu Leu Thr Asn Val Thr Leu Asp His Ser Thr Leu Gly
    290                 295                 300
```

```
Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
            325                 330                 335

His Glu Met Gly His Ser Leu Gly Met Leu His Asp Thr Lys Phe Cys
        340                 345                 350

Thr Cys Gly Ala Lys Pro Cys Ile Met Phe Gly Lys Glu Ser Ile Pro
    355                 360                 365

Pro Pro Lys Glu Phe Ser Ser Cys Ser Tyr Asp Gln Tyr Asn Lys Tyr
370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
                405                 410                 415

Glu Glu Cys Asp Cys Gly Ser Pro Ala Asp Cys Arg Asn Pro Cys Cys
            420                 425                 430

Asp Ala Ala Thr Cys Lys Leu Lys Pro Gly Ala Glu Cys Gly Asn Gly
        435                 440                 445

Glu Cys Cys Asp Lys Cys Lys Ile Arg Lys Ala Gly Thr Glu Cys Arg
    450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro Cys Leu
                485                 490                 495

Asn Asn Ser Gly Tyr Cys Tyr Asn Gly Asp Cys Pro Ile Met Leu Asn
            500                 505                 510

Gln Cys Ile Ala Leu Phe Ser Pro Ser Ala Thr Val Ala Gln Asp Ser
        515                 520                 525

Cys Phe Gln Arg Asn Leu Gln Gly Ser Tyr Tyr Gly Tyr Cys Thr Lys
    530                 535                 540

Glu Ile Gly Tyr Tyr Gly Lys Arg Phe Pro Cys Ala Pro Gln Asp Val
545                 550                 555                 560

Lys Cys Gly Arg Leu Tyr Cys Leu Asp Asn Ser Phe Lys Lys Asn Met
                565                 570                 575

Arg Cys Lys Asn Asp Tyr Ser Tyr Ala Asp Glu Asn Lys Gly Ile Val
            580                 585                 590

Glu Pro Gly Thr Lys Cys Glu Asp Gly Lys Val Cys Ile Asn Arg Lys
        595                 600                 605

Cys Val Asp Val Asn Thr Ala Tyr
    610                 615

<210> SEQ ID NO 101
<211> LENGTH: 62
<212> TYPE: DNA
<213> ORGANISM: Artificial Sequence
<220> FEATURE:
<223> OTHER INFORMATION: Oligo number ZC58325, Oligonucleotide

<400> SEQUENCE: 101
caatgaattt tttctcaaat tttcgttcat gaggaggaac aattaacccc aaagtctttt    60
tg                                                                  62

<210> SEQ ID NO 102
<211> LENGTH: 13
<212> TYPE: PRT
<213> ORGANISM: Artificial Sequence
```

```
<220> FEATURE:
<223> OTHER INFORMATION: Ecarin zinc metalloprotease zinc-binding active
      site. For example, in certain embodiments, the zinc
      metalloprotease comprises the zinc-binding active site containing
      the motif represented by SEQ ID NO:103.
<220> FEATURE:
<221> NAME/KEY: METAL
<222> LOCATION: (1)..(13)
<223> OTHER INFORMATION: Xaa may be any amino acid.

<400> SEQUENCE: 102

Xaa His Glu Xaa Xaa His Xaa Xaa Gly Xaa Xaa His Xaa
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Ecarin zinc metalloprotease zinc-binding active
      site. For example, in certain embodiments, the zinc
      metalloprotease comprises the zinc-binding active site containing
      the motif represented by SEQ ID NO:103.
<220> FEATURE:
<221> NAME/KEY: METAL
<222> LOCATION: (1)..(11)
<223> OTHER INFORMATION: Xaa may be any amino acid

<400> SEQUENCE: 103

Ala His Glu Xaa Gly His Xaa Xaa Gly Xaa Xaa His Asp
1               5                   10

<210> SEQ ID NO 104
<211> LENGTH: 6
<212> TYPE: PRT
<213> ORGANISM: Artificial Sequence
<220> FEATURE:
<223> OTHER INFORMATION: The ecarin proprotein cysteine switch motif,
      similar to that involved in the activation of other matrix
      metalloproteinase zymogens.
<220> FEATURE:
<221> NAME/KEY: ACT_SITE
<222> LOCATION: (1)..(6)

<400> SEQUENCE: 104

Pro Lys Met Cys Gly Val
1               5

<210> SEQ ID NO 105
<211> LENGTH: 11
<212> TYPE: PRT
<213> ORGANISM: Artificial Sequence
<220> FEATURE:
<223> OTHER INFORMATION: Another typical zinc-chelating sequence, as
      found in crayfish astacin.
<220> FEATURE:
<221> NAME/KEY: METAL
<222> LOCATION: (1)..(10)
<223> OTHER INFORMATION: Xaa may be any amino acid

<400> SEQUENCE: 105

His Glu Xaa Xaa His Xaa Xaa Gly Xaa Xaa His
1               5                   10
```

We claim:

1. A recombinant metalloprotease pre-pro-activator comprising, from an amino-terminal position to a carboxyl-terminal position, a pre-pro leader that shares at least 60% sequence identity with the pre-pro leader from *Echis carinatus* ecarin wild-type metalloprotease pre-pro-activator; a thrombin cleavage site consisting of a glycine, a proline, and an arginine; and a mature activator that shares at least 60% sequence identity with the mature activator from the *Echis carinatus* ecarin wild-type metalloprotease pre-pro-activator.

2. The recombinant metalloprotease pre-pro-activator of claim 1, wherein the pre-pro leader shares at least 60% sequence identity with amino acid residues 1-187 of SEQ ID NO:100; and wherein the mature activator shares at least 60% sequence identity with amino acid residues 191-616 of SEQ ID NO:100.

3. The recombinant metalloprotease pre-pro-activator of claim 1, wherein said pre-pro-activator shares at least 90% sequence identity with the amino acid sequence of residues 1-616 of SEQ ID NO:2.

4. The recombinant metalloprotease pre-pro-activator of claim 1, wherein said pre-pro-activator shares at least 99% sequence identity with the amino acid sequence of residues 1-616 of SEQ ID NO:2.

5. The recombinant metalloprotease pre-pro-activator as in claim 1, further comprising an affinity tag positioned carboxyl-terminal to the mature activator.

6. The recombinant metalloprotease pre-pro-activator of claim 5, wherein said affinity tag is a histidine tag.

7. The recombinant metalloprotease pre-pro-activator as in claim 1, wherein said pre-pro-activator consists essentially of the pre-pro leader, the thrombin cleavage site, and the mature activator.

8. The recombinant metalloprotease pre-pro-activator as in claim 1, wherein said pre-pro leader comprises at least thirty-five contiguous amino acid residues from amino acid residues 1-187 of SEQ ID NO:100.

9. The recombinant metalloprotease pre-pro-activator as in claim 1, wherein said pre-pro leader comprises amino acid residues 153-187 of SEQ ID NO:100.

10. The recombinant metalloprotease pre-pro-activator as in claim 1, wherein said pre-pro leader comprises amino acid residues 1-187 of SEQ ID NO:100.

11. A recombinant metalloprotease pre-pro-activator comprising the amino acid sequence of residues 1-616 of SEQ ID NO:2.

12. An isolated pre-pro-activator polypeptide produced by transfecting a host cell with an expression vector comprising a polynucleotide sequence encoding a pre-pro-activator as in claim 1; and expressing the encoded pre-pro-activator from said expression vector.

13. The recombinant metalloprotease pre-pro-activator of claim 1, wherein said mature activator comprises amino acid residues 188-616 of SEQ ID NO:2, 189-616 of SEQ ID NO:2, 190-616 of SEQ ID NO:2, or 191-616 of SEQ ID NO:2.

* * * * *

UNITED STATES PATENT AND TRADEMARK OFFICE
CERTIFICATE OF CORRECTION

PATENT NO. : 8,759,066 B2
APPLICATION NO. : 12/935235
DATED : June 24, 2014
INVENTOR(S) : Paul D. Bishop et al.

It is certified that error appears in the above-identified patent and that said Letters Patent is hereby corrected as shown below:

On the Title Page, Item (56)

Line 4, please replace "co1." with --col.--

Line 6, please replace "matix" with --matrix--

Line 9, please replace "cloining" with --cloning--

Signed and Sealed this
Twelfth Day of May, 2015

Michelle K. Lee
*Director of the United States Patent and Trademark Office*